(12) United States Patent
Chou et al.

(10) Patent No.: US 11,885,952 B2
(45) Date of Patent: Jan. 30, 2024

(54) OPTICS, DEVICE, AND SYSTEM FOR ASSAYING AND IMAGING

(71) Applicant: Essenlix Corporation, Monmouth Junction, NJ (US)

(72) Inventors: Stephen Y. Chou, Princeton, NJ (US); Wei Ding, East Windsor, NJ (US); Ji Qi, Hillsborough, NJ (US); Yuecheng Zhang, Yardley, PA (US); Wu Chou, Basking Ridge, NJ (US); Mingquan Wu, Princeton Junction, NJ (US); Xing Li, Metuchen, NJ (US); Jun Tian, Belle Mead, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 902 days.

(21) Appl. No.: 16/526,864

(22) Filed: Jul. 30, 2019

(65) Prior Publication Data

US 2020/0033579 A1  Jan. 30, 2020

Related U.S. Application Data

(60) Provisional application No. 62/716,911, filed on Aug. 9, 2018, provisional application No. 62/716,353, filed (Continued)

(51) Int. Cl.
*G02B 21/34* (2006.01)
*G01N 33/543* (2006.01)
*G01N 33/50* (2006.01)

(52) U.S. Cl.
CPC ....... *G02B 21/34* (2013.01); *G01N 33/54386* (2013.01); *G01N 33/5094* (2013.01); *G01N 2496/05* (2013.01)

(58) Field of Classification Search
CPC .. G02B 21/34; G02B 27/32; G01N 33/54386; G01N 33/5094; G01N 2496/05;
(Continued)

(56) References Cited

U.S. PATENT DOCUMENTS 3,368,872 A   2/1968  Natelson
3,447,863 A   6/1969  Patterson
(Continued)

FOREIGN PATENT DOCUMENTS

AU   198813789 A   9/1988
AU      619459 B   1/1992
(Continued)

OTHER PUBLICATIONS

Van Vliet, Dillys et al., Prediction of asthma exacerbations in children by innovative exhaled inflammatory markers: Results of a longitudinal study, PLOS One, Mar. 23, 2015, vol. 10. No. 3, e0119434.
(Continued)

*Primary Examiner* — Dennis White

(57) ABSTRACT

A method of assaying an analyte in a sample is disclosed. The method includes having a sample holder with a sample contact area for contacting a sample with an analyte, having a plurality of calibration structures on the sample contact area of the sample holder, imaging a part of the sample contact area that has the calibration structures, and using an algorithm that includes an image, calibration structures in the image, and artificial intelligence and/or machine learning to identify the analyte and/or determine the analyte concentration.

32 Claims, 12 Drawing Sheets

Related U.S. Application Data on Aug. 8, 2018, provisional application No. 62/716,338, filed on Aug. 8, 2018, provisional application No. 62/712,204, filed on Jul. 30, 2018.

(58) Field of Classification Search
CPC .... G01N 21/76; G01N 21/6456; G01N 21/78; G01N 2201/0221; A61B 5/00; A61B 5/1455; A61B 5/1495
See application file for complete search history.

(56) References Cited

U.S. PATENT DOCUMENTS

| | | |
|---|---|---|
| 3,895,661 A | 7/1975 | Praglin et al. |
| 3,925,166 A | 12/1975 | Blume |
| 3,992,158 A | 11/1976 | Przybylowicz et al. |
| 4,022,521 A | 5/1977 | Hall et al. |
| 4,066,412 A | 1/1978 | Johnson et al. |
| 4,088,448 A | 5/1978 | Lilja et al. |
| 4,171,866 A | 10/1979 | Tolles |
| 4,233,029 A | 11/1980 | Columbus |
| 4,255,384 A | 3/1981 | Kitajima et al. |
| 4,258,001 A | 3/1981 | Pierce et al. |
| 4,329,054 A | 5/1982 | Bachalo |
| 4,402,614 A | 9/1983 | Porath |
| 4,427,294 A | 1/1984 | Pietro |
| 4,430,436 A | 2/1984 | Koyama et al. |
| 4,596,695 A | 6/1986 | Cottingham |
| 4,745,075 A | 5/1988 | Hadfield et al. |
| 4,806,311 A | 2/1989 | Greenquist |
| 4,883,642 A | 11/1989 | Bisconte |
| 4,906,439 A | 3/1990 | Grenner |
| 4,911,782 A | 3/1990 | Brown |
| 4,950,455 A | 8/1990 | Smith |
| 5,002,736 A | 3/1991 | Babbitt et al. |
| 5,039,487 A | 8/1991 | Smith |
| 5,096,836 A | 3/1992 | Macho et al. |
| 5,122,284 A | 6/1992 | Braynin et al. |
| 5,132,097 A | 7/1992 | Van Deusen et al. |
| 5,169,601 A | 12/1992 | Ohta et al. |
| 5,188,968 A | 2/1993 | Kano et al. |
| 5,223,219 A | 6/1993 | Subramanian et al. |
| 5,281,540 A | 1/1994 | Merkh et al. |
| 5,306,467 A | 4/1994 | Douglas-Hamilton et al. |
| 5,321,975 A | 6/1994 | Wardlaw |
| 5,362,648 A | 11/1994 | Koreyasu et al. |
| 5,413,732 A | 5/1995 | Buhl et al. |
| 5,427,959 A | 6/1995 | Nishimura et al. |
| 5,431,880 A | 7/1995 | Kramer |
| 5,591,403 A | 1/1997 | Gavin et al. |
| 5,623,415 A | 4/1997 | O'Bryan et al. |
| 5,753,456 A | 5/1998 | Naqui et al. |
| 5,768,407 A | 6/1998 | Shen et al. |
| 5,858,648 A | 1/1999 | Steel et al. |
| 5,879,628 A | 3/1999 | Ridgeway et al. |
| 5,888,834 A | 3/1999 | Ishikawa et al. |
| 5,939,326 A | 8/1999 | Chupp et al. |
| 5,948,686 A | 9/1999 | Wardlaw |
| 6,004,821 A | 12/1999 | Levine et al. |
| 6,016,367 A | 1/2000 | Benedetti et al. |
| 6,017,767 A | 1/2000 | Chandler |
| 6,022,734 A | 2/2000 | Wardlaw |
| 6,106,778 A | 8/2000 | Oku et al. |
| 6,180,314 B1 | 1/2001 | Berndt |
| 6,235,536 B1 | 5/2001 | Wardlaw |
| 6,350,613 B1 | 2/2002 | Wardlaw et al. |
| 6,358,475 B1 | 3/2002 | Berndt |
| 6,429,027 B1 | 8/2002 | Chee et al. |
| 6,503,760 B2 | 1/2003 | Malmqvist et al. |
| 6,551,554 B1 | 4/2003 | Vermeiden et al. |
| 6,623,701 B1 | 9/2003 | Eichele et al. |
| 6,632,652 B1 | 10/2003 | Austin et al. |
| 6,714,287 B2 | 3/2004 | Berndt |
| 6,723,290 B1 | 4/2004 | Wardlaw |
| 6,844,201 B2 | 1/2005 | Malmqvist et al. |
| 6,866,823 B2 | 3/2005 | Wardlaw |
| 6,869,570 B2 | 3/2005 | Wardlaw |
| 6,893,850 B2 | 5/2005 | Ostuni et al. |
| 6,921,514 B1 | 7/2005 | Vetter et al. |
| 6,929,953 B1 | 8/2005 | Wardlaw |
| 6,939,032 B2 | 9/2005 | Cosby et al. |
| 7,101,341 B2 | 9/2006 | Tsukashima et al. |
| 7,179,423 B2 | 2/2007 | Bohm et al. |
| 7,282,367 B2 | 10/2007 | Kawamura |
| 7,393,658 B2 | 7/2008 | Carbonell et al. |
| 7,410,617 B2 | 8/2008 | Sakamoto |
| 7,410,807 B2 | 8/2008 | D'Aurora |
| 7,468,160 B2 | 12/2008 | Thompson et al. |
| 7,510,841 B2 | 3/2009 | Stuelpnagel et al. |
| 7,510,848 B2 | 3/2009 | Hammond et al. |
| 7,547,424 B2 | 6/2009 | Haab et al. |
| 7,731,901 B2 | 6/2010 | Wardlaw |
| 7,738,094 B2 | 6/2010 | Goldberg |
| 7,850,916 B2 | 12/2010 | Wardlaw |
| 7,862,773 B2 | 1/2011 | Ibrahim |
| 7,863,411 B2 | 1/2011 | Hammond et al. |
| 7,897,376 B2 | 3/2011 | Porter et al. |
| 7,901,897 B2 | 3/2011 | Stuelpnagel et al. |
| 7,903,241 B2 | 3/2011 | Wardlaw et al. |
| 7,929,121 B2 | 4/2011 | Wardlaw et al. |
| 7,929,122 B2 | 4/2011 | Wardlaw et al. |
| 7,943,093 B2 | 5/2011 | Adrien et al. |
| 7,951,599 B2 | 5/2011 | Levine et al. |
| 7,995,194 B2 | 8/2011 | Wardlaw et al. |
| 8,045,165 B2 | 10/2011 | Wardlaw et al. |
| 8,058,073 B2 | 11/2011 | Chiapperi et al. |
| 8,077,296 B2 | 12/2011 | Wardlaw et al. |
| 8,081,303 B2 | 12/2011 | Levine et al. |
| 8,133,738 B2 | 3/2012 | Levine et al. |
| 8,158,434 B2 | 4/2012 | Wardlaw |
| 8,221,985 B2 | 7/2012 | Wardlaw et al. |
| 8,241,572 B2 | 8/2012 | Wardlaw |
| 8,269,954 B2 | 9/2012 | Levine et al. |
| 8,284,384 B2 | 10/2012 | Levine et al. |
| 8,287,820 B2 | 10/2012 | Williams et al. |
| 8,310,658 B2 | 11/2012 | Wardlaw et al. |
| 8,310,659 B2 | 11/2012 | Wardlaw et al. |
| 8,319,954 B2 | 11/2012 | Wardlaw et al. |
| 8,326,008 B2 | 12/2012 | Lalpuria et al. |
| 8,338,579 B2 | 12/2012 | Adams et al. |
| 8,361,799 B2 | 1/2013 | Levine et al. |
| 8,367,012 B2 | 2/2013 | Wardlaw |
| 8,462,332 B2 | 6/2013 | Pugia et al. |
| 8,467,063 B2 | 6/2013 | Wardlaw et al. |
| 8,472,693 B2 | 6/2013 | Davis et al. |
| 8,481,282 B2 | 7/2013 | Levine et al. |
| 8,502,963 B2 | 8/2013 | Levine et al. |
| 8,513,032 B2 | 8/2013 | Jablonski et al. |
| 8,569,076 B2 | 10/2013 | Wardlaw et al. |
| 8,594,768 B2 | 11/2013 | Phillips et al. |
| 8,604,161 B2 | 12/2013 | Hammond et al. |
| 8,628,952 B2 | 1/2014 | Stuelpnagel et al. |
| 8,633,013 B2 | 1/2014 | Kaiser et al. |
| 8,638,427 B2 | 1/2014 | Wardlaw et al. |
| 8,717,673 B2 | 5/2014 | Selvin et al. |
| 8,741,630 B2 | 6/2014 | Dickinson et al. |
| 8,750,966 B2 | 6/2014 | Phillips et al. |
| 8,778,687 B2 | 7/2014 | Levine et al. |
| 8,781,203 B2 | 7/2014 | Davis et al. |
| 8,796,186 B2 | 8/2014 | Shirazi |
| 8,797,527 B2 | 8/2014 | Hukari et al. |
| 8,835,186 B2 | 9/2014 | Jablonski et al. |
| 8,837,803 B2 | 9/2014 | Wang et al. |
| 8,842,264 B2 | 9/2014 | Wardlaw et al. |
| 8,885,154 B2 | 11/2014 | Wardlaw et al. |
| 8,906,700 B2 | 12/2014 | Lim et al. |
| 8,911,815 B2 | 12/2014 | Kram et al. |
| 8,974,732 B2 | 3/2015 | Lalpuria et al. |
| 8,994,930 B2 | 3/2015 | Levine et al. |
| 9,023,641 B2 | 5/2015 | Rodriguez et al. |
| 9,044,268 B2 | 6/2015 | Phillips et al. |
| 9,046,473 B2 | 6/2015 | Levine et al. |
| 9,084,995 B2 | 7/2015 | Wardlaw |
| 9,086,408 B2 | 7/2015 | Egan et al. |
| 9,097,640 B2 | 8/2015 | Goldberg et al. |

(56) References Cited

U.S. PATENT DOCUMENTS

| | | |
|---|---|---|
| 9,199,233 B2 | 12/2015 | Wardlaw |
| 9,274,094 B2 | 3/2016 | Wardlaw et al. |
| 9,291,617 B2 | 3/2016 | Levine et al. |
| 9,322,835 B2 | 4/2016 | Wardlaw |
| 9,347,962 B2 | 5/2016 | Salsman |
| 9,354,159 B2 | 5/2016 | Vaartstra |
| 9,395,365 B2 | 7/2016 | Levine et al. |
| 9,469,871 B2 | 10/2016 | Bearinger et al. |
| 9,523,670 B2 | 12/2016 | Mueller et al. |
| 9,696,252 B2 | 7/2017 | Wardlaw |
| 2001/0055882 A1 | 12/2001 | Ostuni |
| 2003/0068614 A1 | 4/2003 | Cima et al. |
| 2003/0107946 A1 | 6/2003 | Cosby et al. |
| 2003/0109059 A1 | 6/2003 | Adrien et al. |
| 2004/0131345 A1 | 7/2004 | Kylberg et al. |
| 2004/0156755 A1 | 8/2004 | Levine |
| 2004/0214310 A1 | 10/2004 | Parker et al. |
| 2004/0259162 A1 | 12/2004 | Kappel et al. |
| 2005/0026161 A1 | 2/2005 | Jablonski et al. |
| 2005/0032138 A1 | 2/2005 | Lathrop et al. |
| 2005/0036667 A1 | 2/2005 | So et al. |
| 2005/0158880 A1 | 7/2005 | Ostuni et al. |
| 2005/0254995 A1 | 11/2005 | Sostek et al. |
| 2006/0011860 A1 | 1/2006 | Hect et al. |
| 2006/0015157 A1 | 1/2006 | Leong |
| 2006/0051253 A1 | 3/2006 | Gousepohl |
| 2006/0062440 A1 | 3/2006 | Hollars et al. |
| 2006/0062695 A1 | 3/2006 | Haab et al. |
| 2006/0090658 A1 | 5/2006 | Phillips |
| 2006/0160134 A1 | 7/2006 | Melker et al. |
| 2007/0087442 A1 | 4/2007 | Wardlaw |
| 2007/0243117 A1 | 10/2007 | Wardlaw |
| 2008/0028962 A1 | 2/2008 | Phillips et al. |
| 2008/0214947 A1 | 9/2008 | Hunt et al. |
| 2008/0274564 A1 | 11/2008 | D'Aurora |
| 2008/0286152 A1 | 11/2008 | Schmidt et al. |
| 2009/0079978 A1 | 3/2009 | Kimura |
| 2009/0211344 A1 | 8/2009 | Wang |
| 2009/0227472 A1 | 9/2009 | Stuelpnagel et al. |
| 2009/0233329 A1 | 9/2009 | Rodriguez et al. |
| 2009/0246781 A1 | 10/2009 | Klem et al. |
| 2009/0258371 A1 | 10/2009 | Wardlaw et al. |
| 2009/0298716 A1 | 12/2009 | Stuelpnagel et al. |
| 2010/0081583 A1 | 4/2010 | Shirazi |
| 2010/0085067 A1 | 4/2010 | Gabriel et al. |
| 2010/0151593 A1 | 6/2010 | D'Aurora |
| 2010/0216248 A1 | 8/2010 | Wardlaw |
| 2010/0255605 A1 | 10/2010 | Wardlaw |
| 2010/0272345 A1 | 10/2010 | Wardlaw |
| 2010/0273244 A1 | 10/2010 | Wardlaw |
| 2010/0291562 A1 | 11/2010 | Adler |
| 2011/0009163 A1 | 1/2011 | Fletcher et al. |
| 2011/0009297 A1 | 1/2011 | Jones et al. |
| 2011/0206557 A1 | 8/2011 | Phan et al. |
| 2011/0294198 A1 | 12/2011 | Wardlaw |
| 2012/0034647 A1 | 2/2012 | Herzog et al. |
| 2012/0107799 A1 | 5/2012 | Daum |
| 2012/0108787 A1 | 5/2012 | Lue |
| 2012/0157160 A1 | 6/2012 | Ozcan et al. |
| 2012/0157332 A1 | 6/2012 | Kumar et al. |
| 2012/0300293 A1 | 11/2012 | Selvin et al. |
| 2013/0065788 A1 | 3/2013 | Glezer et al. |
| 2013/0102018 A1 | 4/2013 | Schentag et al. |
| 2013/0157288 A1 | 6/2013 | Kilfeather et al. |
| 2013/0209332 A1 | 8/2013 | Wardlaw |
| 2013/0265054 A1 | 10/2013 | Lowery et al. |
| 2013/0300919 A1 | 11/2013 | Fletcher et al. |
| 2013/0309679 A1 | 11/2013 | Ismagilov et al. |
| 2014/0315242 A1 | 10/2014 | Rodriguez et al. |
| 2014/0368631 A1 | 12/2014 | Wardlaw et al. |
| 2015/0036131 A1 | 2/2015 | Salsman |
| 2015/0253321 A1 | 9/2015 | Chou et al. |
| 2015/0317506 A1 | 11/2015 | Xie et al. |
| 2015/0323519 A1 | 11/2015 | Wardlaw |
| 2016/0004057 A1 | 1/2016 | Lin et al. |
| 2016/0025637 A1 | 1/2016 | Halverson et al. |
| 2016/0033496 A1 | 2/2016 | Chou et al. |
| 2016/0245797 A1 | 8/2016 | Ahmad et al. |
| 2016/0266091 A1 | 9/2016 | Levine et al. |
| 2017/0021356 A1 | 1/2017 | Dority et al. |
| 2017/0038401 A1 | 2/2017 | Holmes et al. |
| 2017/0045504 A1 | 2/2017 | Bloom |

FOREIGN PATENT DOCUMENTS

| | | |
|---|---|---|
| CN | 1299466 | 6/2001 |
| CN | 1302229 | 7/2001 |
| CN | 1166950 | 9/2004 |
| CN | 1188217 | 2/2005 |
| CN | 102027369 | 4/2011 |
| EP | 261667 A2 | 3/1988 |
| EP | 291153 A1 | 11/1988 |
| EP | 261667 A3 | 5/1989 |
| EP | 291153 B1 | 6/1992 |
| EP | 261667 B1 | 2/1993 |
| EP | 0961110 | 12/1999 |
| EP | 1949310 A2 | 7/2008 |
| EP | 2290100 | 3/2011 |
| EP | 1949310 A4 | 11/2011 |
| EP | 2439515 | 4/2012 |
| EP | 2554987 | 2/2013 |
| EP | 3026433 | 6/2016 |
| EP | 1949310 B1 | 2/2019 |
| WO | 1991000009 | 12/1991 |
| WO | 1999044743 | 9/1999 |
| WO | 1999045385 | 9/1999 |
| WO | 2003062920 | 7/2003 |
| WO | 2005114145 | 12/2005 |
| WO | 2005100539 | 1/2006 |
| WO | 2007112332 | 10/2007 |
| WO | 2009117652 | 9/2009 |
| WO | 2009117664 | 9/2009 |
| WO | 2009117678 | 9/2009 |
| WO | 2009117682 | 9/2009 |
| WO | 2009124186 | 10/2009 |
| WO | 2009124190 | 10/2009 |
| WO | 2009126800 | 10/2009 |
| WO | 2010115026 | 10/2010 |
| WO | 2014055559 | 4/2014 |
| WO | 2014089468 | 6/2014 |
| WO | 2014183049 | 11/2014 |
| WO | 2014205576 | 12/2014 |
| WO | 2017048871 | 3/2017 |
| WO | WO-2017048871 A1 * | 3/2017 ............ B01L 3/5055 |

OTHER PUBLICATIONS

Written Opinion for PCT/US2018/017713 established by ISA/KR, dated Jun. 20, 2018.

* cited by examiner

OPTICS, DEVICE, AND SYSTEM FOR ASSAYING AND IMAGING

CROSS-REFERENCE TO RELATED APPLICATIONS

This application claims the benefit of priority under 35 U.S.C. § 119 to U.S. Provisional Patent Application No. 62/712,204, filed on Jul. 30, 2018, U.S. Provisional Patent Application No. 62/716,353, filed on Aug. 8, 2018, U.S. Provisional Patent Application No. 62/716,338, filed on Aug. 8, 2018, and U.S. Provisional Patent Application No. 62/716,911, filed on Aug. 9, 2018, the contents of which is relied upon and incorporated herein by reference in their entirety. The entire disclosure of any publication or patent document mentioned herein is entirely incorporated by reference.

FIELD

Among other things, the present invention is related to devices, systems, and methods for imaging analytes in a sample, determining or identifying the analyte, and/or determining an analyte concentration.

BACKGROUND

In biological and chemical assays (e.g. diagnostic testing), often it needs to simple, fast, and sensitive assaying, including imaging. The present invention provides, among other thing, devices and methods for simple, fast, and sensitive assaying, including imaging.

SUMMARY OF INVENTION

The following brief summary is not intended to include all features and aspects of the present invention, nor does it imply that the invention must include all features and aspects discussed in this summary.

The present disclosure provides a method of assaying an analyte in a sample including having a sample holder with a sample contact area for contacting a sample with an analyte, having a plurality of calibration structures on the sample contact area of the sample holder, wherein the calibration structures have predetermined inter-distance between two neighboring calibration structures, and each of the calibration structures has an average lateral dimension of 100 um or less, imaging a part of the sample contact area that has the calibration structures; and using an algorithm that includes an image of the part of the sample contact area that has calibration structures, the calibration structures in the image, and artificial intelligence and/or machine learning to identify the analyte, and/or determine the analyte concentration.

In some embodiments, the present invention includes a system of assaying an analyte in a sample. The system includes a sample holder with a sample contact area for contacting a sample with an analyte, a plurality of calibration structures on the sample contact area of the sample holder, wherein the calibration structures have predetermined inter-distance between two neighboring calibration structures and each of the calibration structures has a lateral dimension of an average 100 um or less, an imager that images a part of the sample contact area that has the calibration structures, and an algorithm that includes an image of a part of the sample contact area that has the calibration structures, the calibration structures in the image, and artificial intelligence and/or machine learning to identify the analyte and/or determine the analyte concentration.

In some embodiments, the present invention includes an optical adaptor for assaying an analyte in a sample. The optical adaptor includes a sample holder frame and an imager, wherein the sample holder frame has a sample holder and at least one plate with a sample contact area for contacting a sample with an analyte; and the sample holder on the sample contact area has a plurality of calibration structures that have a predetermined and known inter-distance between two neighboring calibration structures, and wherein the optical calibration structures are imaged by an imager and are used by an algorithm that comprises the images from the imager, the calibration structures in the image, and artificial intelligence and/or machine learning to identify the analyte, and/or determine the analyte concentration.

BRIEF DESCRIPTION OF THE DRAWINGS

The skilled artisan will understand that the drawings, described below, are for illustration purposes only. The drawings are not intended to limit the scope of the present teachings in any way. The drawings not are not entirely in scale. In the figures that present experimental data points, the lines that connect the data points are for guiding a viewing of the data only and have no other means.

DETAILED DESCRIPTION OF THE PRESENT INVENTION

The following detailed description illustrates some embodiments of the invention by way of example and not by way of limitation. The section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

I. Device and System that Use Sample Cards (e.g., a QMAX Card), Markers, Adaptors, Camera, and Phone The terms "calibration mark", "monitoring mark", and "reference mark" are used interchangeably throughout the disclosure.

Assay Using a Single Plate.

Figure 1:
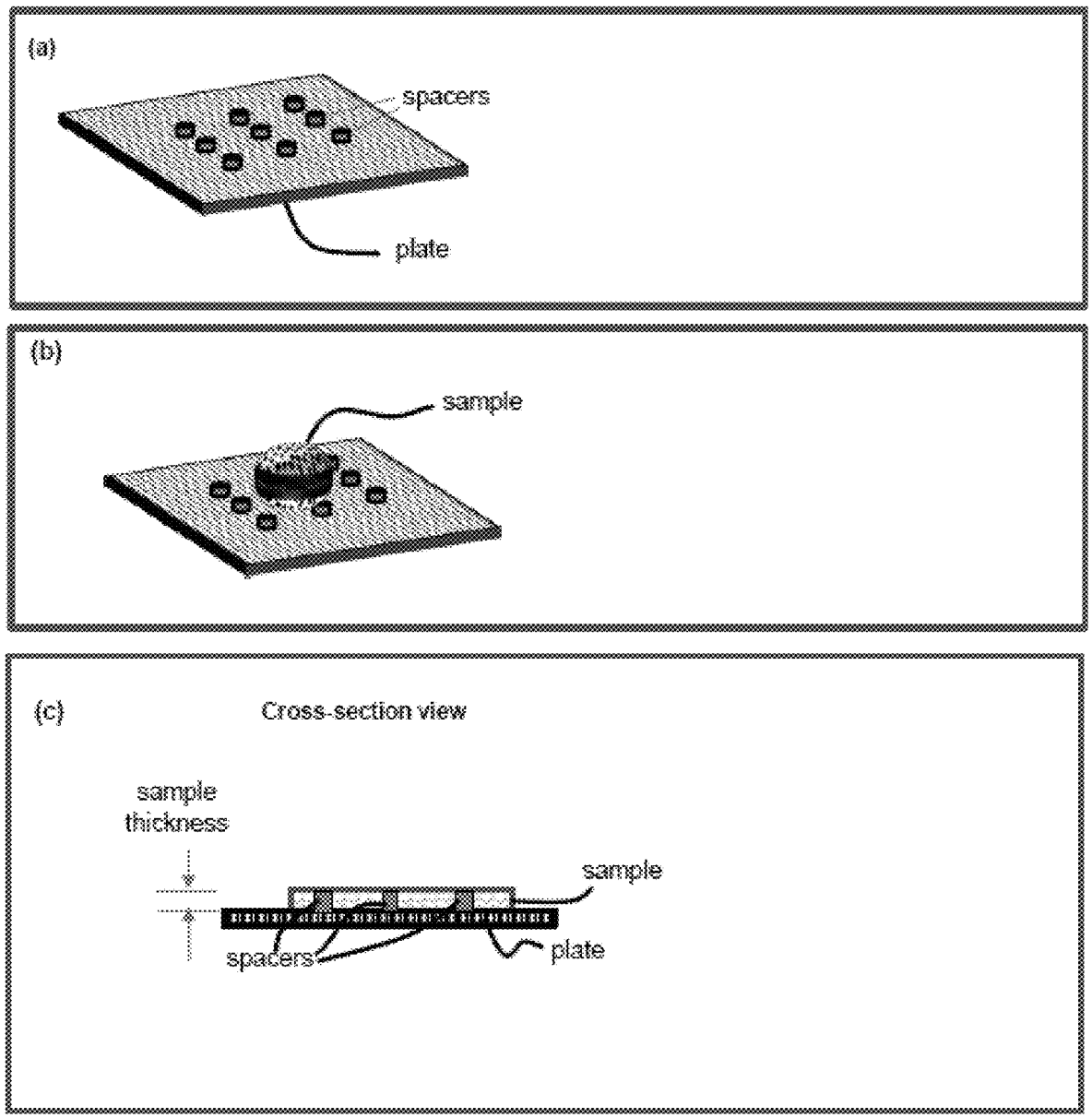
FIG. 1 is an illustration of spacers (i.e., optical calibration marks) on a plate that holds a sample with analyte. The sample can be imaged by an imager (not shown).

As illustrated in FIG. 1, the disclosure provides a method of imaging an analyte in a sample comprising:
  i. having a sample holder with a sample contact area, and is in contact with a sample with an analyte;
  ii. having micro/nano optical calibration structures on the sample contact area of the sample holder, wherein the micro/nano optical calibration structures have predetermined and known inter-distance between two neighboring calibration structures;
  iii. imaging a part of the sample contact area having the micro/nano optical calibration structures to provide images; and
  iv. using an algorithm including:
    (a) the images provided in iii;
    (b) the calibration structures in the image; and
    (c) artificial intelligence, machine learning, or both,
  to (1) identify the analyte, (2) determine the analyte concentration, or both (1) and (2).

Figure 2:
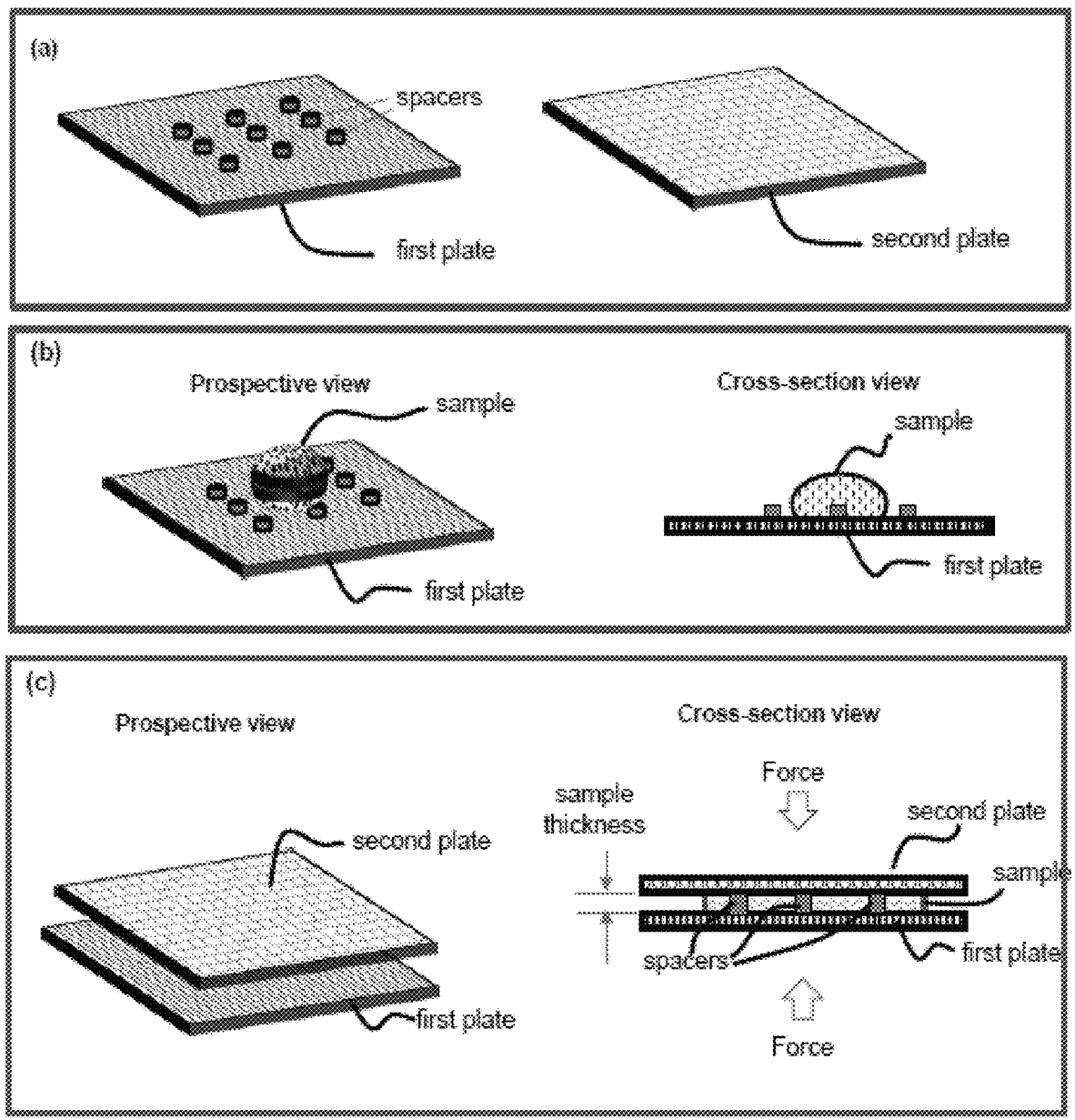
FIG. 2 is an illustration of spacers (i.e., optical calibration marks) on a plate that holds a sample with analyte. The sample is sandwiched between two plates which are separated by spacers. The spacers control the final distance between the plates and serve as an optical calibrator for imaging. The sample can be imaged by an imager (not shown).

As illustrated in FIG. 2, the disclosure provides a system for imaging an analyte in a sample comprising:
  i. a sample holder with a sample contact area, and in contact with a sample with an analyte;
  ii. micro/nano optical calibration structures on the sample contact area of the sample holder, wherein the micro/nano optical calibration structures have predetermined and known inter-distance between two neighboring calibration structures;
  iii. an imager that images a part of the sample contact area that has micro/nano optical calibration structures to provide images; and
  iv. an algorithm including
    (a) the images provided in iii,
    (b) the calibration structures in the image, and
    (c) artificial intelligence, machine learning, or both,
  to (1) identify the analyte, (2) determine the analyte concentration, or both (1) and (2).

NN-3 A sample holder for imaging an analyte in a sample, comprising a sample holder and an imager, wherein:
  (1) the sample holder comprises:
    i. a sample holder with a sample contact area, that is in contact with a sample containing an analyte to be analyzed;
    ii. micro/nano optical calibration structures on the sample contact area of the sample holder, wherein the micro/nano optical calibration structures have predetermined and known inter-distance patterns between two neighboring calibration structures;
  wherein the micro/nano optical calibration structures are imaged by an imager and used by an algorithm that comprises
    (a) the images in iii,
    (b) the calibration structures in the image, and
    (c) artificial intelligence and/or machine learning,
      to (1) identify the analyte, or (2) determine the analyte concentration or both (1) and (2), including the morphological structure of the detected analytes (e.g., shape, size, contour).

In some embodiment, images of the samples for assaying are collected and labeled to form a training database. However, departing from the known methods, the training database in the present disclosure takes into account the micro/nano optical calibration structures.

In some embodiment, the micro/nano optical structures can be applied to the labeling in the training data, to make the analytes form a single layer in the image by controlling the gap of the sample holding device. Otherwise, the analytes cannot be properly imaged, labeled, or detected.

In some embodiment, the micro/nano structures can be applied to determine the filed-of-view of the analytes in the image, and can be used to find the true dimension or size of the analytes in the image, for example, mapping them from pixels in image to their actual physical dimensions (e.g., micrometers).

In some embodiment, the micro/nano structures can be used to enable machine learning for analyte detection. A machine learning model can be built from the labeled training database using the micro/nano structure embraced in the images of the sample taken over the device. The machine learning model of the disclosure can be applied to detect the analytes in the image of the sample for assaying, to segment the detected analytes from others, to determine their shape, count their occurrences, determine their concentration, and like determinations, all from the micro/nano structures described herein.

In some embodiment, the machine learning model for analyte detection can be based on Fast RCNN which is trained on the training database described herein.

In some embodiment, the analyte detection and characterization can be based on a combined approach of image processing and machine learning, where image processing methods are applied to do a rough detection and a machine learning model, e.g., DenseNet, can be trained and applied to do verification and filtering of false alarms.

In some embodiment, the analyte detection and characterization can be based on image transformation using, for example, GAN (Generative and Adversarial Network) based machine learning model, combined with post image processing.

Assaying Using Two Plates.

NN-4. A device for imaging analyte in a sample, comprising a sample card (e.g., QMAX device) and an imager, wherein:
(1) the sample card comprises:
a first plate, a second plate, and spacers, wherein:
   i. the plates are movable relative to each other into different configurations;
   ii. one or both plates are flexible;
   iii. each of the plates has, on its respective inner surface, a sample contact area for contacting a deformable sample;
   iv. one or both of the plates comprise the spacers that are fixed with a respective plate;
   v. the spacers have a predetermined substantially uniform height and a predetermined inter-spacer-distance; and
   vi. at least one of the spacers is inside the sample contact area;
      wherein in an open configuration the two plates are separated apart, the spacing between the plates is not regulated by the spacers, and the sample is deposited on one or both of the plates; and
      wherein in a closed configuration, configured after the sample deposition in the open configuration, at least part of the sample is compressed by the two plates into a layer of uniform thickness, and the uniform thickness of the layer is confined by the inner surfaces of the two plates and is regulated by the plates and the spacers; and
(2) the imager is configured to capture an image of signals emanating from at least part of the layer of uniform thickness.

NN-5. A system for tomography, comprising a sample card (e.g., QMAX device), an imager, a holder, and a control device, wherein:
(1) the sample card (e.g., QMAX device) device comprises: a first plate, a second plate, and spacers, as described in section NN-4 above; and
(2) the imager comprises an image sensor and a lens, wherein:
   i. the lens is configured to focus signals emanating from at least part of the layer of uniform thickness and project the focused signals to the image sensor, and
   ii. the image sensor is configured to capture images of said focused signals;
(3) the holder is configured to adjust relative position between the sample card and the imager; and
(4) the control device comprises hardware and software for controlling, deducing the position adjustment made by the holder, and receiving and reconstructing the images into a three-dimensional volume.

In some embodiments, the calibration marks can additionally have definite and predetermined (i.e., known in advance) geometry (i.e., size and shape). In some embodiments, the calibration marks can additionally have predetermined optical properties. In some embodiments, the calibration marks can be periodic. In some embodiments, the calibration marks can be periodic and cover a significant area or an entire area of the sample contact area. In some embodiments, the calibration marks can be periodic and have a period of, for example, 20 um or less, 50 um, 100 um, 150 um, 200 um, 400 um, including intermediate values or ranges. In some preferred embodiments, the calibration marks can be periodic and have a period of, for example, 200 um or less. In another preferred embodiments, the calibration marks can be periodic and have a period of, for example, 150 um or less. A periodic array of calibration marks does not require or reduce the requirements of the position precision.

The analyte can include, for example, cells, viruses, bacteria, nanoparticles, and molecules.

II. Optical Adaptor for Colorimetric Reader Attachment to Smartphone (Fiber-Ring Illumination)

Colorimetric assay is a very powerful technique having wide applications in health monitoring, disease diagnostic, chemical analysis, and like applications. The significant factor for getting an accurate colorimetric assay result is to accurately quantify the color change. Conventionally, the color change of a colorimetric test strip is analyzed by comparing the color change with a standard color card. But this comparison is accomplished by human's eye and can be easily influenced by the environment light condition, which limits the accuracy of quantifying the color change.

The disclosure addresses this problem and provides a solution with a system comprising an optical adaptor and a smartphone. The optical adaptor device fits over a smartphone and converts the combination into a colorimetric reader which can provide a consistent and uniform illumination to illuminate the front surface of the colorimetric test card and capture the image of the sample to analyze the color change. This system can be operated conveniently and reliably by a common person at any location. The optical adaptor takes advantage of the existing resources of the smartphone, including camera, light source, processor and display screen, and provides a low-cost solution to accurately quantify the color change of a colorimetric assay.

The disclosure provides an optical adaptor device comprising a holder frame fitting over the upper part of the smartphone and an optical box attached to the holder having a sample receptacle slot and illumination optics. In reports by others for the attachment of an adaptor to a smartphone, their adaptor design was a whole piece including clip-on mechanical parts to fit over the smartphone and the functional elements. Such a design was limited by having to redesign the whole-piece adaptor for each specific model of smartphone. In the present disclosure, the optical adaptor can be separated into a holder frame only for fitting a smartphone and a universal optical box containing all the functional parts. For the smartphones with different dimensions, as long as the relative positions of the camera and the light source are the same, only the holder frame need to be redesigned, which can save costs of design and manufacture.

In some embodiments, the optical box of the optical adaptor can comprise: a slotted receptacle having a slot that receives and positions the colorimetric sample in the field of view and focal range of the smartphone camera; and an illumination and imaging optics to create uniform and consistent illumination on the sample independently of any external conditions and to capture the sample image.

To capture the sample image to accurately represent the color change, it is desirable that the sample area under the camera is uniformly illuminated. But for all common smartphones, the light source is always a point source and mounted next to the camera with some distance, which means the light source is not central symmetric relative to the camera. This causes the problem that, when the sample is placed very close to the camera of smartphone, without the help of additional illumination optics, the illumination pattern on the front surface of a sample in the field of view of the camera will have a gradient intensity change in a linear direction. Hence, it is desirable to create a light source with large emitting area and central symmetric to the camera. To achieve this purpose a plastic side-emitting fiber ring is put around the smartphone camera to make the fiber ring central symmetric relative to the camera. The two end faces of the fiber ring are mounted towards the light source of the smartphone. This converts the original single point light source to an infinite number of small light sources having nearly equal luminous intensity distributed on a circle with equal distance from the smartphone camera. The light emitted from the side wall of the fiber ring passes through a diffusive film to increase the emitting area and make the illumination more even. The sample area beneath the camera is uniformly front-illuminated by the designed illumination optics based on side-emitting fiber ring. In some embodiments, the light is fed into a fiber illuminator from both ends of the fiber. In some embodiments, the light is fed from only one end of the fiber. In some embodiments, light fed from two ends can improve the light emitting uniformity from the side of the fiber. In some embodiments, the light source for the fiber illuminator can be from the flash light of a smart phone. In some embodiments, the light source for the fiber ring illuminator can be from a light source other than that of a smartphone.

The fiber ring can use a side-emitting fiber. Unlike a conventional fiber which has light entering from one end of the fiber, exiting from the other end, and having little leaking out from the side of the fiber, a side-emitting fiber can have a significant amount of light leaking out from the side of the fiber, that can provide excellent illumination.

How the color of a colorimetric sample is represented can greatly depend on the illumination condition, it can be important to control the illumination in the optical box to be independent of any external light conditions. To solve this problem, the light source and the sample can be situated in the sample enclosed adaptor (i.e., chamber or cavity) that prevents or greatly reduces the effects of ambient light outside the chamber on the measurements. Furthermore, in some embodiments, the slotted receptacle can have a door (e.g., made of rubber) attached to it to fully cover the slot to prevent ambient light from entering the optical box and distorting the results the illumination condition.

Typically, the optical box can also comprise a lens mounted in the box and aligned with the camera of the smartphone, which places the sample within the focal range of the camera. The images captured by the camera can be further processed by the processor of smartphone to analyze the color change, and output the analysis result to the screen of smartphone.

A sample slider can be mounted inside the receptacle slot to receive the sample card (e.g., QMAX device) and position the sample in the sample card in the field of view and focal range of the smartphone camera.

The sample slider can include a fixed track frame and a moveable arm. The frame track is fixedly mounted in the receptacle slot of the optical box. The track frame can have a sliding track slot that fits the width and thickness of the sample card so that the sample card can slide along the track. The width and height of the track slot can be carefully configured to make the sample card shift less than 0.5 mm in the direction perpendicular to the sliding direction in the sliding plane and shift less than less than 0.2 mm along the thickness direction of the sample card.

The frame track can have an open window under the field of view of the camera of smartphone to allow the light to back-illuminate the sample.

A moveable arm can be built into the sliding track slot of the track frame and move together with the sample card to guide the movement of sample card in the track frame.

The moveable arm (also called "lever") equipped with a stopping mechanism with two pre-defined stop positions. For one position, the arm will make the sample card stop at the position where a fixed sample area on the sample card is directly under the camera of smartphone. For the other position, the arm will make the sample card stop at the position where the sample area on sample card is out of the field of view of the smartphone and the sample card can be easily taken out of the track slot.

The moveable arm switches between the two stop positions by a pressing the sample card and the moveable arm together to the end of the track slot and then releasing.

The moveable arm can indicate if the sample card can be inserted in correct direction. The shape of one corner of the sample card can be configured to be different from the other three right angle corners. The shape of the moveable arm can match the shape of the corner with the special shape so that the sample card only in correct direction can slide to correct position in the track slot.

Figure 3:
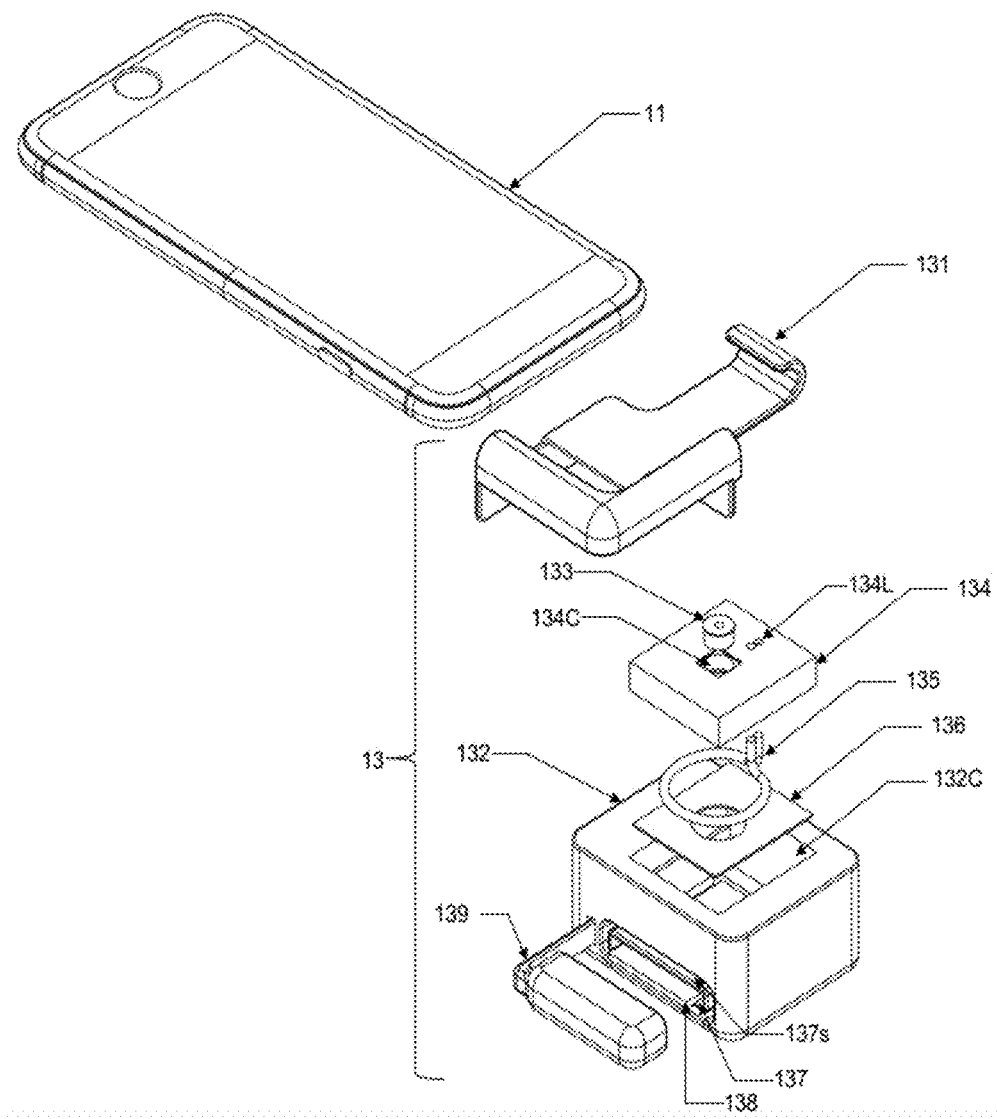
FIG. 3 shows an exploded view of the optical adaptor device according to one embodiment of the present invention.

FIG. 3 is an exploded view of the optical adaptor device. The device comprises a holder case 131 fitting over the upper part of smartphone 1; an optical box 132 attached to case 131 including a receptacle slot 137, an optics chamber 132C and a resilient (e.g., rubber) door 139 inserted into trench 137s to cover receptacle slot 137. An optics insert 134 is fitted into the top of optics chamber 132C with an exit aperture 134L and an entrance aperture 134C in it aligning with light source and camera in smartphone. A lens 133 is mounted in entrance aperture 134C in optics insert 134 and configured so that the sample area on colorimetric sample card 138 inserted into receptacle slot 137 is located within the working distance of the smartphone camera. A side-emitting optical fiber ring 135 is mounted in optics insert 134 configured to make the camera 1C in the center of the fiber ring 135. Both end faces of optical fiber ring 135 are mounted in exit aperture 134L facing the light source 1L. A light diffuser film 136 is put under the optical fiber ring 135 and has a hole opened for the aperture of lens. Optical fiber ring 135 whose operation as the illumination optics in the optical adaptor is described below in FIG. 3.

Figure 4A:
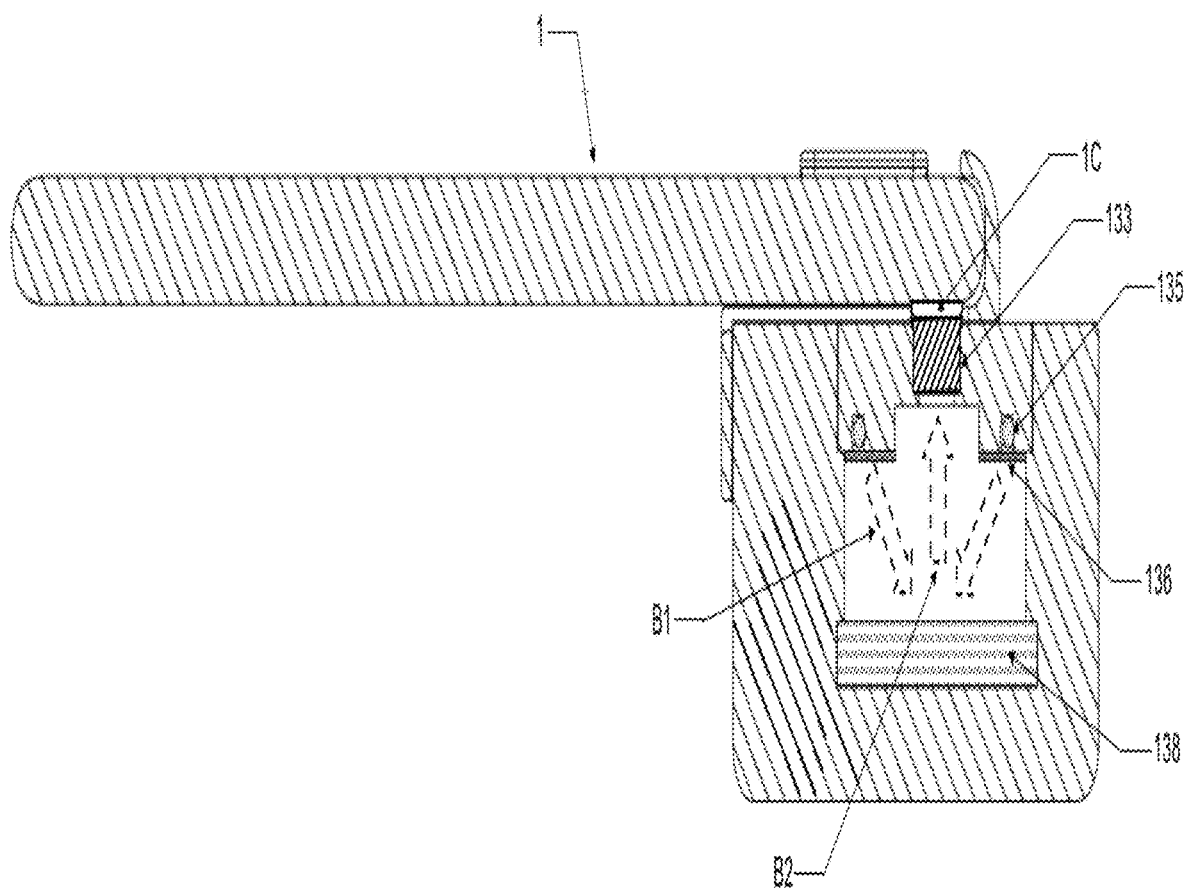
FIG. 4A shows a cross sectional view of the optical adaptor device according to one embodiment of the present invention.
Figure 4B:
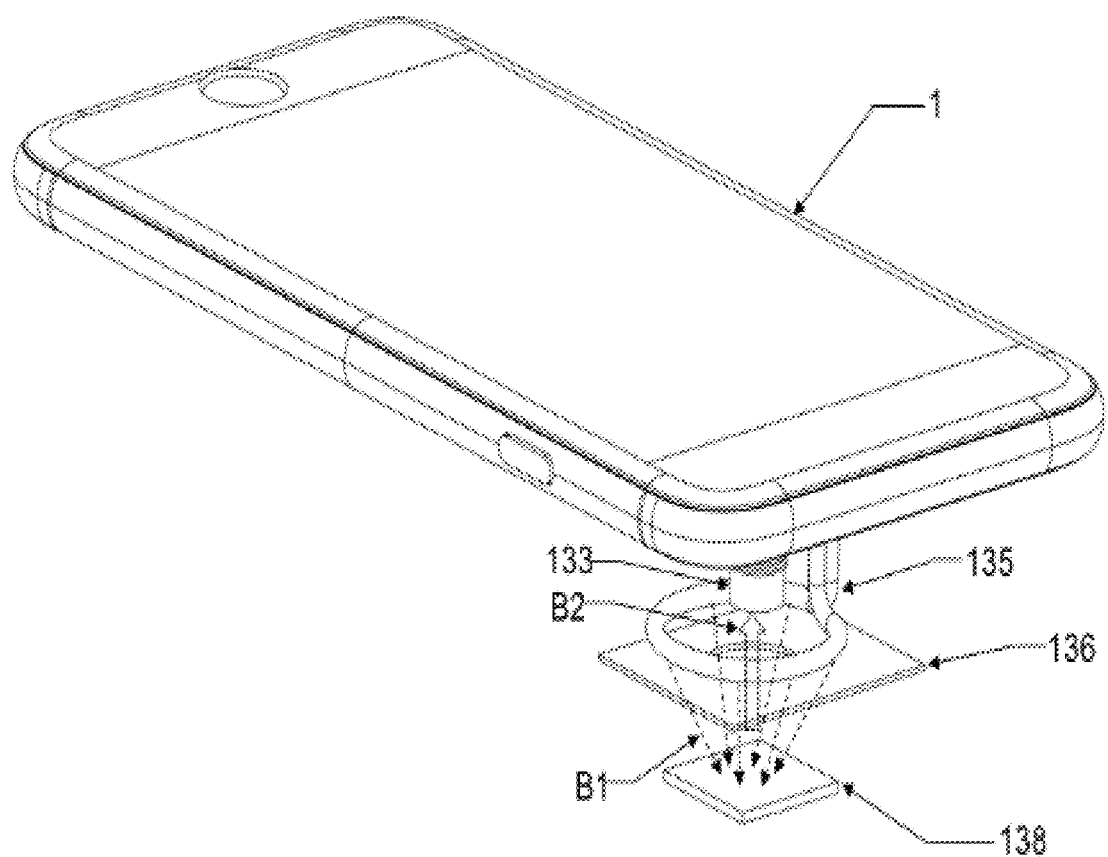
FIG. 4B shows a schematic view of the optical adaptor device according to one embodiment of the present invention.
Figure 4C:
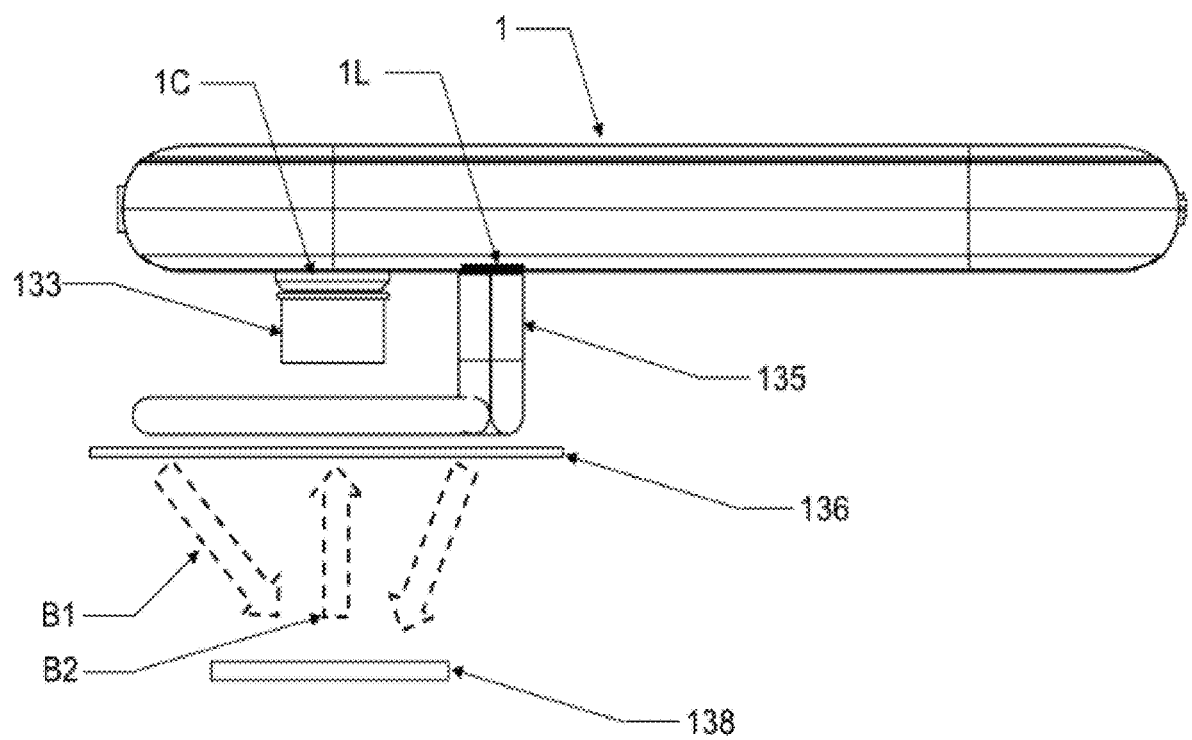
FIG. 4C shows a schematic view of the optical adaptor device according to one embodiment of the present invention.

FIGS. 4A, 4B and 4C are the schematic views showing details of the optical adaptor reading a colorimetric card. FIG. 4A is the sectional view showing details of the optical adaptor. And FIG. 4B and FIG. 4C are the schematic views only showing the configuration of the optics elements in the adaptor. These figures illustrate the functionality of the elements that were described above with reference to FIG. 2. The light emitted from light source 1L is coupled into side-emitting optical fiber ring 135 from the two end faces of fiber ring 135 and travels inside along the ring. Beam B1 is emitted out from the side wall of fiber ring and go through the diffuser film 136. Beam B1 illuminates the sample area of colorimetric sample card 138 right under the camera 1C from front side to create uniform illumination. The illuminated sample area absorbs part of beam B1 and reflects the beam B1 to beam B2. Beam B2 is collected by lens 133 and gets into camera 1C Lens 133 creates an image of the sample area on the image sensor plane of camera 1C. Smartphone 1 captures and processes the image to analyze the color information in the image to quantify the color change of the colorimetric assay.

The optical enclosure encloses the imager, lens and illumination light source. The optical enclosure has an opening that can be pressed against skin. The opening has an orifice. The orifice of the open is configured, so that skin and the orifice can form an optical seal, reducing or eliminating ambient light enter to optical enclosure.

The materials of the orifice are selected from polystyrene, PMMA, PC, COC, COP, or another plastic.

The opening has a lateral dimension of 1 mm, 2 mm, 5 mm, 8 mm, 10 mm, 12 mm, 15 mm, 20 mm, including intermediate values and ranges.

Some Examples

1. Fiber Ring-Illuminator
   In some embodiments of optical assembly:
   a. the radius of the side illumining ring fiber can be 10 mm;
   b. the diameter of ring fiber can be at least 5 mm, 10 mm, 15 mm, 20 mm, 25 mm, 30 mm, 40 mm, 50 mm, 60 mm, 80 mm, or 100 mm, including intermediate values and ranges;
   c. the diameter of the cross-section of the ring fiber can be at least 0.5 mm, 1.0 mm, 1.5 mm, 2.0 mm, 2.5 mm, 3 mm, 4 mm, 5 mm, 6 mm, 8 mm, or 10 mm, including intermediate values and ranges;
   d. the side-emitting fiber can be a plastic optical fiber;
   e. the shape of the fiber ring can be a rotational symmetric closed contour, such as a circle, square, regular hexagon, etc.
   In some embodiments of optical assembly:
   f. the external imager lens can have a diameter of 6 mm;
   g. the diameter of the imager lens can be at least 2 mm, 3 mm, 4 mm, 5 mm, 10 mm, 15 mm, 20 mm, 25 mm, 30 mm, 40 mm, or 50 mm, including intermediate values and ranges.

In some embodiments of optical assembly, the fiber ring can be used in combination with a micro-lens array or be replaced by a micro-lens array.

In some embodiments of optical assembly, the optical assembly can include a light diffuser plate between the sample and the fiber ring, and the light diffusive plate can have an aperture configured to be aligned with the camera.

In some embodiments of optical assembly, the length of one side of the diffusive plate can be at least 5 mm, 10 mm, 15 mm, 20 mm, 25 mm, 30 mm, 40 mm, 50 mm, 100 mm, 150 mm, or 200 mm, or in a range between any of the two values, wherein the thickness of the diffusive plate can be at least 2 mm, 3 mm, 4 mm, 5 mm, 10 mm, 15 mm, or 20 mm, including intermediate values and ranges.

In some embodiments of optical assembly, the distance between the diffusive plate and fiber ring can be, for example, at least 1 mm, 10 mm, 15 mm, 20 mm, 25 mm, 30 mm, 40 mm, 50 mm, 100 mm, including intermediate values and ranges.

The optical assembly of claim 2, wherein the distance between the sample and fiber ring can be, for example, at least 2 mm, 10 mm, 15 mm, 20 mm, 25 mm, 30 mm, 40 mm, 50 mm, 100 mm, 150 mm, 200 mm, including intermediate values and ranges.

III. Skin Imager Using Fiber Ring as Illuminator

The optical system for skin inspection can inspect an area of skin by high-resolution image or video which reveal the fine details of the features on skin. The optical system for skin inspection comprises a digital imager and an optical adaptor. The optical adaptor further comprises a lens, an illumination light source and an optical enclosure.

The optical enclosure (also termed "adaptor") encloses the imager, lens, and the illumination light source. The optical enclosure has an opening that can be pressed against skin. The opening is configured to allow a portion of the skin to be examined to be illuminated by the illuminator inside of the adaptor enclosure and to be viewed by the imager that attached to the adaptor. The orifice of the opening is configured, so that skin and the orifice can form an optical seal, reducing or eliminating ambient light entering the optical enclosure.

In one embodiment, the illuminator an comprise a side-illumination of a ring-shape fiber which is connected to the flashlight of a smartphone.

In another embodiment, the light source and the imager are provided by a smartphone, and the adaptor does not consume any electrical power.

In another embodiment, the digital imager together with the lens in the optical adaptor forms an imaging system to generate a magnified high-resolution digital image of the area of interest on the skin.

In another embodiment, the area of interest of skin was inspected inside the enclosure of the optical adaptor under the illumination of the light source. To capture the skin image to accurately represent the true details of the skin, it is desirable that the skin under the imager is uniformly illuminated. Because a small area's magnified view of skin is the interest of this inspection system, the skin will be very close to the imager. But the conventional point light source placed next to the imager cannot generate a central symmetric illumination relative to the imager. This causes the problem that, when the skin can be placed very close to the imager, the illumination pattern on the skin in the field of view of the imager will have a gradient intensity change in a linear direction. Hence, it is desirable to create a light source with large emitting area and central symmetric to the camera to produce a uniform illumination light pattern on the skin sample. To achieve this purpose, the illumination light source comprises an optical fiber ring and a point light source. A plastic side-emitting fiber ring is put around the imager lens to make the fiber ring central symmetric relative to the imager. And the two end faces of the fiber ring are mounted towards a point light source. The light coupled into the fiber from the end faces will emit out from the side walls. This will convert the original single point light source to infinite number of small light sources having nearly equal luminous intensity distributed on a circle with equal distance from the imager. The light emitted from the side wall of the fiber ring further goes through a diffusive film to increase the emitting area and make the illumination more even. The skin sample area directly under the imager can be uniformly illuminated by the designed illumination optics based on side-emitting fiber ring.

In another embodiment, the fiber ring can use a side-emitting fiber. An optical fiber has a high-refractive-index core and a low-refractive-index cladding layer. For a conventional end-emitting fiber, the light propagates in the core and is trapped by the total internal reflection at the core/cladding boundary. And the boundary is very efficient and total internal reflectivity is close to 100%. So, light can only come out of the fiber from the end surfaces. However, for a side-emitting fiber, the core/cladding boundary is inefficient and rough. At the boundary, a small percentage of light is scattered into the cladding layer and then into the air.

FIG. 3 shows details of an optical system for inspecting a skin area. The light emitted from light source 1L is coupled into side-emitting optical fiber ring 135 from the two end faces of fiber ring 135 and travels inside along the ring. Beam B1 is emitted out from the side wall of fiber ring and go through the diffuser film 136. Beam B1 illuminates the sample area of skin 138 right under the imager 1C from front side to create uniform illumination. The illuminated sample area absorbs part of beam B1 and reflects the beam B1 to beam B2. Beam B2 is collected by lens 133 and gets into imager 1C. Lens 133 creates an image of the sample area on the imager 1C.

In some embodiments, the illumination optics can include, for example:
- both end faces of the side-emitting fiber can face towards the point light source;
- the light coupled into the side-emitting fiber can partially emit out of the fiber from the side wall when propagating along the fiber;
- the side-emitting fiber forms a ring shape central symmetric around the imager;
- the side-emitting fiber can be made of a plastic optical fiber;
- the side-emitting fiber can be made of plastic optical fiber;
- the side-emitting fiber can be made in size from 0.1 mm to 20 mm in diameter;
- a preferred diameter of side-emitting fiber can be half of the diameter of the point light source aperture;
- a preferred radius of fiber ring can be the distance between the light source aperture and the imager;
- the shape of the fiber ring can be a rotational symmetric closed contour, and can be, for example, a circle, square, regular hexagon, and like geometries;
- the radius of fiber ring can be 3 mm, 5 mm, 10 mm, 20 mm, 50 mm, 100 mm, including intermediate values and ranges; or
- a light diffuser can be placed between the skin sample and illumination fiber ring.

Methods for Taking 3D Image

Figure 5:
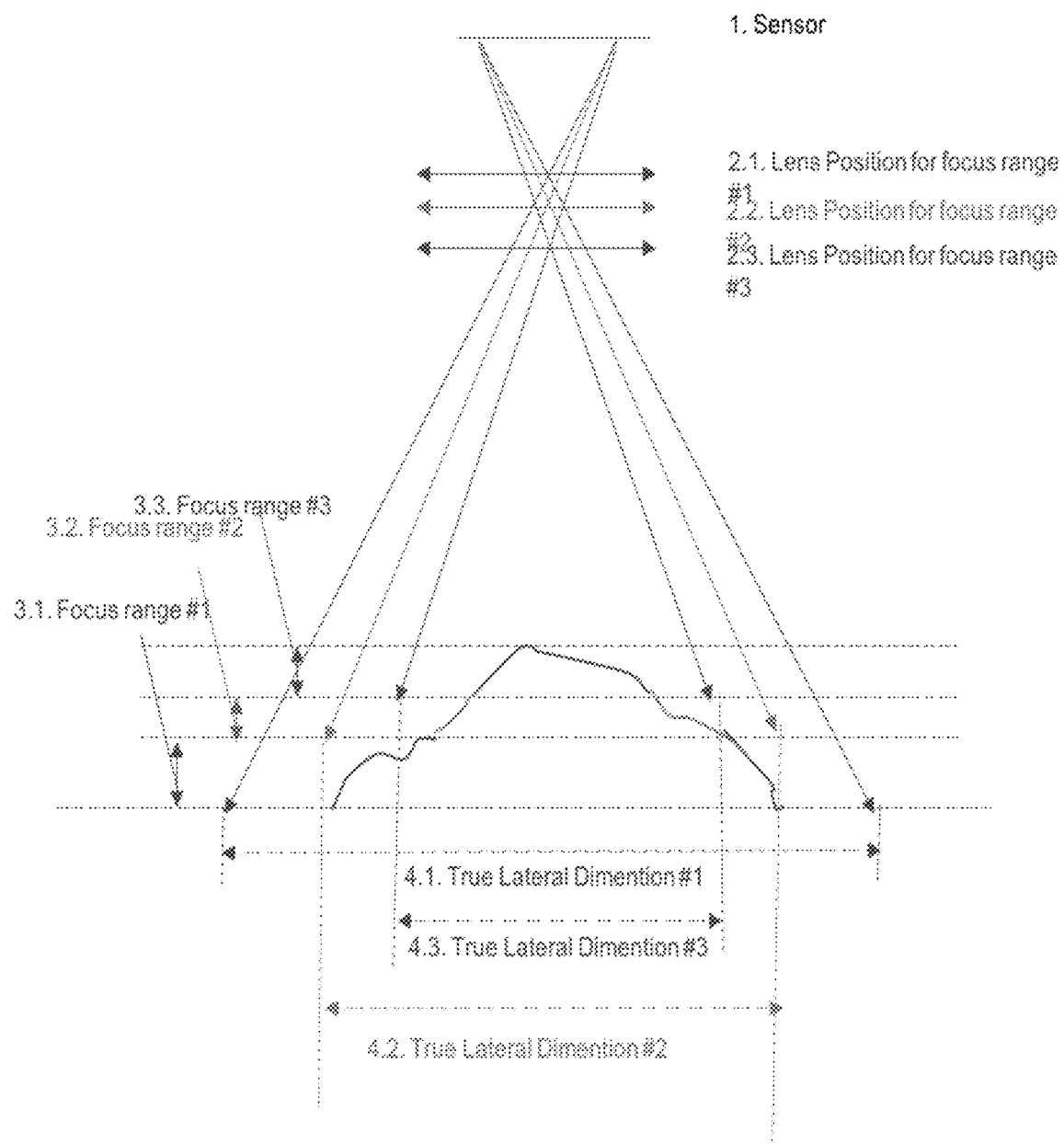
FIG. 5 shows a schematic view of a method for taking a 3D image according to one embodiment of the present invention.
Figure 6:
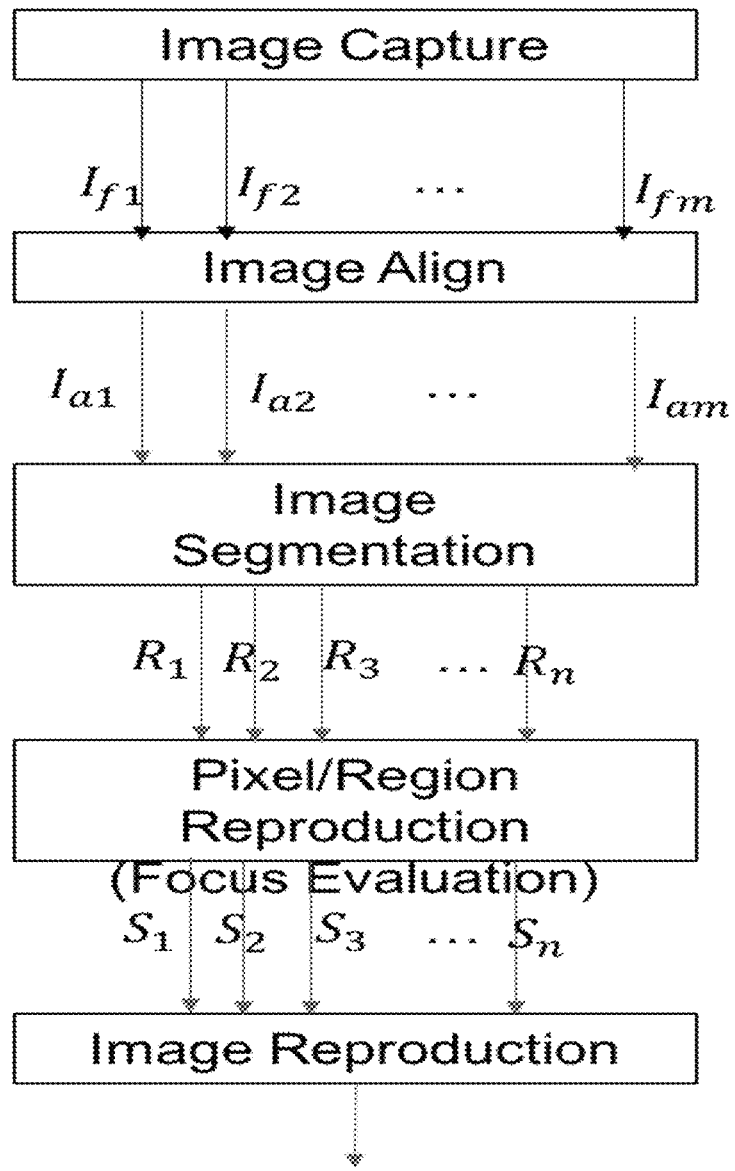
FIG. 6 shows an algorithm for forming a 3D image according to one embodiment of the present invention.

When the pressing the image adaptor opening against the skin, because of the elasticity of the skin, the skin will form a semi-cylindrical hill shape inside the opening. As shown in FIG. 5, for a given imager/lens system, due to the limited optical capability of lens, focus can only be achieved within certain range of object-lens distance (focus range). In some embodiments, the system takes multiple images with different focus to cover a much deeper object observation distance than any single focus range to inspect entire surface of the semi-cylindrical-hill-shape skin. In some embodiments, the image alignment algorithm (FIG. 6) will align the previously mentioned multiple images to at least pixel-level accuracy. Using that algorithm a group of images with matching pixels is created. In some embodiments, in the present invention, the focus evaluation algorithm (FIG. 6) will generate a numerical reading to represent the focus condition of any pixel/region in an image. In some embodiments, the pixel selection algorithm (FIG. 6) chooses the pixel/region with the best focus evaluation value to represent the pixel/region among the image group in reproduction of a super-focused image.

In some embodiments, a lever for switching light from an optical path of light from one path to another or for changing a property of light, wherein the lever is inside of a frame (in some embodiments, the frame is an enclosure) comprises:
- (a) one or two planes, wherein all planes move together with the lever; and
- (b) at least two optical elements on each plane, wherein an optical path goes through at least two optical elements that are on at least one plane;
- wherein the lever is capable of moving into at least two positions, and wherein, for the same incident light, the lever at one position will modify a property of the light different from that when the lever is at another position.

In some embodiments, in the present invention, a lever for switching light from an optical path of light from one path to another or for changing a property of light, wherein the lever is inside of an frame comprises:
- (a) at least two planes, wherein all planes move together with the lever; and
- (b) at least two optical elements on each plane;
- wherein the lever is capable of moving into at least two positions, and for the same incident light, the lever at one position will modify a property of the light different from that when the lever is at another position.

In some embodiments, the lever comprises at least two planes.

In some embodiments, the lever comprises two planes at different heights.

The upper plane can have at least two positions for mounting different optical elements including a through opening. The bottom plane has mounting positions for the optical elements paired with the optical elements on the upper plane in the same vertical axis. By switching between different mounting positions, the optical elements on the upper plane together with the optical elements of bottom plane at the corresponding vertical positions create different functional optical paths in the optical box, for example, bright-field illumination, and fluorescent illumination. In some embodiments, a lever for switching light from an optical path of light from one path to another or for changing a property of light, wherein the lever is inside of a frame comprises:
- (a) one or two planes, wherein all planes move together with the lever; and
- (b) at least two optical elements on each plane;
- wherein the lever is capable of moving into at least two positions, and wherein, for the same incident light, the lever at one position will modify a property of the light different from that when the lever is at another position.

In some embodiments, the planes are not in parallel with each other.

In some embodiments, two of the planes can have an angle of 5, 10, 20, 30, 45, 60, 75, or 90 degrees, including intermediate values or ranges.

In some embodiments, two of the planes can have a preferred angle of 30, 45, or 60 degrees, including intermediate values or ranges.

In some embodiments, the optical elements on one of the planes can include, for example, lenses, prisms, diffusers, mirrors, diffraction gratings, filters, polarizers, optical condensers, light guides, dark surface, or anti-reflection coating.

In some embodiments, the lateral dimension of the optical elements on the plane can be 1 mm, 2 mm, 3 mm, 5 mm, 7 mm, 10 mm, 12 mm, 15 mm, 20 mm, 25 mm, including intermediate values or ranges.

In some embodiments, the lateral dimension of the plane is 5 mm, 8 mm, 10 mm, 12 mm, 15 mm, 20 mm, 25 mm, 30 mm, 40 mm, including intermediate values or ranges.

In some embodiments, the thickness of the plane is 0.2 mm, 0.5 mm, 1 mm, 1.2 mm, 1.5 mm, 2 mm, including intermediate values or ranges.

In some embodiments, the material of the lever is plastic as polystyrene, PETE, polyethylene, PVC, polypropylene, PLA, polycarbonate, POM, Nylon, ABS and others.

In some embodiments, the material of the lever can be metal.

In some embodiments, part of the lever is outside the frame.

In some embodiments, the weight of the lever is 0.5 g, 1 g, 2 g, 3 g, 5 g, 8 g, 10 g, 15 g, 20 g, including intermediate values or ranges.

The term "optical element" refers to any element that can change a property of the light that shines on the element (e.g., reflectors, lenses, filters, absorbers, attenuators, polarizers, and like components), and any element that light can go through (e.g., a hole on a plane of the lever).

EXAMPLES

A1. An optical adaptor, comprising:
i. a holder frame, and
ii. an optical box removably attached to the holder frame, wherein the holder frame is configured to removably fit over a mobile device and align the optical box to a camera and an illumination source integrated in the mobile device;
wherein the optical box comprises sample receptacle slot and illumination optics.

B1. An optical system, comprising:
i. the optical adaptor of embodiment A1; and
ii. a QMAX card, which comprises a first plate and a second, wherein the first plate and the second compresses a liquid sample into a layer of uniform thickness of less than 200 um; and
iii. a slider that configured to accommodate the QMAX card and to be asserted into the optical box.

C1. The adaptor or system of any prior embodiments, wherein the mobile device is a smart phone.

C2. The adaptor or system of any prior embodiments, wherein the holder frame comprises a holder case that is configured to be replaceable with other holder cases having a different size for different mobile devices.

C3. The adaptor or system of any prior embodiments, wherein the holder frame is sized to removably fit the optical adaptor to an upper part of the mobile device.

C4. The adaptor or system of any prior embodiments, wherein the optical box of the optical adaptor comprises:
i. a receptacle slot that is configured to receive and position the QMAX card in a sample slide in the field of view and focal range of the camera;
ii. a bright-field illumination optics that is configured to capture bright-field microscopy images of the sample;
iii. a fluorescent illumination optics that is configured to capture fluorescent microscopy images of a sample; and
iv. a lever that is configured to switch between bright-field illumination optics and fluorescent illumination optics by sliding inward and outward in the optical box.

C5. The adaptor or system of any prior embodiments, wherein the receptor slot comprises a rubber door, which can fully cover the slot to prevent the ambient light getting into the optical box to be collected by the camera.

C6. The adaptor or system of any prior embodiments, wherein the bright-field illumination optics in the adaptor is configured to receive and turn the beam emitted by the light source so as to back-illuminated the sample in normal incidence angle C7. The adaptor or system of any prior embodiments, wherein optical box further comprises a lens mounted in it and aligned with the camera of the mobile device, which magnifies the images captured by the camera.

C8. The adaptor or system of any prior embodiments, wherein the images captured by the camera are further processed by processors of mobile device and outputs the analysis result on a screen of mobile device.

C9. The adaptor or system of any prior embodiments, wherein the level is slidable and is configured to achieve both bright-field illumination and fluorescent illumination optics in the same optical adaptor.

C10. The adaptor or system of any prior embodiments, wherein optical elements of the fluorescent illumination optics are mounted on the lever and when the lever fully slides into the optical box, C11. The adaptor or system of any prior embodiments, wherein the lever with the fluorescent illumination optics elements block the optical path of bright-field illumination optics and switch the illumination optics to fluorescent illumination optics C12. The adaptor or system of any prior embodiments, wherein when the lever slides out, the fluorescent illumination optics elements mounted on the lever move out of the optical path and switch the illumination optics to bright-field illumination optics C13. The adaptor or system of any prior embodiments, wherein the lever comprises two planes at different heights.

C14. The adaptor or system of any prior embodiments, wherein the two planes are joined together with a vertical bar and move together in or out of the optical box.

C15. The adaptor or system of any prior embodiments, wherein the two planes can be separated and each plane can move individually in or out of the optical box.

C16. The adaptor or system of any prior embodiments, wherein the upper lever plane comprises at least one optical element which can be, but not limited to be an optical filter.

C17. The adaptor or system of any prior embodiments, wherein the upper lever plane moves under the light source and the preferred distance between the upper lever plane and the light source is in the range of 0 to 5 mm.

C18. The adaptor or system of any prior embodiments, wherein part of the bottom lever plane is not parallel to the image plane.

C19. The adaptor or system of any prior embodiments, wherein the surface of the non-parallel part of the bottom lever plane has mirror finish with high reflectivity larger than 95%.

C20. The adaptor or system of any prior embodiments, wherein the non-parallel part of the bottom lever plane moves under the light source and deflects the light emitted from the light source to back-illuminate the sample area right under the camera.

C21. The adaptor or system of any prior embodiments, wherein the preferred tilt angle of the non-parallel part of the bottom lever plane is in the range of 45 degree to 65 degree and the tilt angle is defined as the angle between the non-parallel bottom plane and the vertical plane.

C22. The adaptor or system of any prior embodiments, wherein part of the bottom lever plane is parallel to the image plane and is located under and 1 mm to 10 mm away from the sample.

C23. The adaptor or system of any prior embodiments, wherein the surface of the parallel part of the bottom lever plane is highly light absorptive with light absorption larger than 95%.

C24. The adaptor or system of any prior embodiments, wherein the absorptive surface is to eliminate the reflective light back-illuminating on the sample in small incidence angle.

C25. The adaptor or system of any prior embodiments, wherein the lever comprises a stopper configured to stop the lever.

C26. The adaptor or system of any prior embodiments, wherein the stopper comprises a ball plunger and a groove on the lever is used in order to stop the lever at a pre-defined position when being pulled outward from the adaptor.

C27. The adaptor or system of any prior embodiments, wherein the stopper is configured to allow the user to use arbitrary force the pull the lever but make the lever to stop at a fixed position where the optical adaptor's working mode is switched to bright-filed illumination.

C28. The adaptor or system of any prior embodiments, wherein the sample slider is mounted inside the receptacle slot to receive the QMAX device and position the sample in the QMAX device in the field of view and focal range of the smartphone camera.

C29. The adaptor or system of any prior embodiments, wherein the moveable arm switches between the two stop positions by a pressing the QMAX device and the moveable arm together to the end of the track slot and then releasing.

C30. The adaptor or system of any prior embodiments, wherein the moveable arm can indicate if the QMAX device is inserted in correct direction.

C31. The adaptor or system of any prior embodiments, wherein the shape of one corner of the QMAX device is configured to be different from the other three right angle corners.

C31. The adaptor or system of any prior embodiments, wherein the shape of the moveable arm matches the shape of the corner with the special shape so that only in correct direction can QMAX device slide to correct position in the track slot.

C32. The adaptor or system of any prior embodiments, wherein the sample slider comprises a fixed track frame and a moveable arm:

C33. The adaptor or system of any prior embodiments, wherein the frame track is fixedly mounted in the receptacle slot of the optical box; and the track frame has a sliding track slot that fits the width and thickness of the QMAX device so that the QMAX device can slide along the track. The width and height of the track slot is carefully configured to make the QMAX device shift less than 0.5 mm in the direction perpendicular to the sliding direction in the sliding plane and shift less than less than 0.2 mm along the thickness direction of the QMAX device.

C34. The adaptor or system of any prior embodiments, wherein the frame track has an opened window under the field of view of the camera of smartphone to allow the light back-illuminate the sample.

C35. The adaptor or system of any prior embodiments, wherein the moveable arm is pre-built in the sliding track slot of the track frame and moves together with the QMAX device to guide the movement of QMAX device in the track frame.

C36. The adaptor or system of any prior embodiments, wherein the moveable arm equipped with a stopping mechanism with two pre-defined stop positions.

Other Embodiments

An optical adaptor for imaging an sample using a hand-held imaging device that has a light source, a single camera, and a computer processor, comprising:
    an enclosure;
    a cavity within the enclosure; and
    a lever within the cavity,
    wherein the lever comprises at least one optical element and is configured to be moveable between a first position and a second position, wherein (i) in the first position, said imaging device is capable of imaging a sample in a bright field mode, and (ii) in the second position, said imaging device is capable of imaging the sample in a fluorescence excitation mode.

An optical adaptor for imaging an sample using a hand-held imaging device that has a light source, a single camera, and a computer processor, comprising:
    an enclosure;
    a lens arranged to provide a field of view for the camera;
    a cavity within the enclosure for receiving the sample and positioning the sample within the field of view of the camera, wherein the lens is positioned to receive light refracted by or emitted by the sample when in the field of view of the camera; and
    a lever within the cavity,
    wherein the lever comprises at least one optical element and is configured to be moveable between a first position and a second position, wherein (i) in the first position, said imaging device is capable of imaging a sample in a bright field mode, and (ii) in the second position, said imaging device is capable of imaging the sample in a fluorescence excitation mode.

An optical adaptor for imaging an sample using a hand-held imaging device that has a light source, a single camera, and a computer processor, comprising:
    an enclosure;
    a cavity within the enclosure for receiving the sample and positioning the sample within a field of view of the camera; and
    a lever within the cavity,
    wherein the lever comprises at least one optical element and is configured to be moveable between a first position and a second position, wherein (i) in the first position, said imaging device is capable of imaging a sample in a bright field mode, and (ii) in the second position, said imaging device is capable of imaging the sample in a fluorescence excitation mode, and
    wherein the lever comprises a first planar region extending along a first plane and a second planar region laterally displaced along a first direction from the first planar region and extending along a second plane, the first plane being disposed at a different height along a second direction from the second plane, the second direction being orthogonal to the first direction.

An optical adaptor for imaging an sample using a hand-held imaging device that has a light source, a single camera, and a computer processor, comprising:
    an enclosure;
    a cavity within the enclosure for receiving the sample and positioning the sample within a field of view of the camera; and
    a lever within the cavity,
    wherein the lever comprises at least one optical element and is configured to be moveable between a first position and a second position, wherein (i) in the first position, said imaging device is capable of imaging a sample in a bright field mode, and (ii) in the second position, said imaging device is capable of imaging the sample in a fluorescence excitation mode, and
    wherein the lever comprises a first planar region extending along a first plane and a second planar region laterally displaced along a first direction from the first planar region and extending along a second plane, the first plane being disposed at a different height along a second direction from the second plane, the second direction being orthogonal to the first direction, and
    wherein the first planar region comprises at least one optical element, and the second planar region comprises at least one optical element.

An optical adaptor for imaging an sample using a handheld imaging device that has a light source, a single camera, and a computer processor, comprising:
an enclosure;
a cavity within the enclosure; and
a lever within the cavity,
wherein the lever comprises at least one optical element and is configured to be moveable between at least three different positions, wherein (i) in a first position, said imaging device is capable of imaging a sample in a bright field mode, (ii) in a second position, said imaging device is capable of imaging the sample in a fluorescence excitation mode, and (iii) in a third position, said imaging device is capable of measuring optical absorption of the sample.

An optical adaptor for imaging a sample using a handheld imaging device that has a light source, a single camera, and a computer processor, comprising:
an enclosure;
a lens configured to provide a field of view for the camera;
a cavity within the enclosure for receiving the sample and positioning the sample within the field of view of the camera;
an aperture within the enclosure, wherein the aperture is arranged to receive source light from the light source for illuminating the sample; and
a lever within the cavity,
wherein the lever comprises at least one optical element and is configured to be moveable between a first position and a second position, wherein (i) in a first position, said imaging device is capable of imaging a sample in a bright field mode, (ii) in a second position, said imaging device is capable of imaging the sample in a fluorescence excitation mode, wherein in the fluorescence excitation mode, the lens is arranged to receive light emitted by the sample when the sample is illuminated by the source light.

An optical adaptor for imaging a sample using a smart phone that has a light source, a single camera, and a computer processor, comprising:
an enclosure;
a lens configured to provide a field of view for the camera;
a cavity within the enclosure for receiving the sample and positioning the sample within the field of view of the camera; and
a lever within the cavity,
wherein the lever comprises at least one optical element and is configured to be moveable between a first position and a second position, wherein (i) in a first position, said imaging device is capable of imaging a sample in a bright field mode, and (ii) in a second position, said imaging device is capable of imaging the sample in a fluorescence excitation mode.

An optical assembly attachable to a hand-held electronic device having a light source, a camera, and a computer processor, wherein the optical assembly is configured to enable microscopic imaging of a sample by the camera with illumination of the sample by light from the light source, the optical assembly comprising:
an enclosure;
a cavity within the enclosure;
a lens configured to provide a microscopic field of view for the camera; and
moveable arm within the cavity, wherein the moveable arm is configurable to switch between a first position and a second position, wherein when the moveable arm is in the first position, the optical assembly is in a bright field mode, and when the moveable arm is in the second position, the optical assembly is in a fluorescence excitation mode.

The optical assembly of any embodiments, wherein the enclosure comprises:
a sample receptacle region within the cavity; and
a slot on a side of the enclosure, wherein the slot is arranged to receive a sample substrate within the sample receptacle region and position the sample within the field of view of the camera.

The optical assembly of embodiments, further comprising a first set of one or more optical elements arranged to receive light entering from a first aperture in the enclosure corresponding to the light source and to redirect the light entering from the first aperture along a first pathway toward a second aperture in the enclosure corresponding to the camera to provide bright field illumination of the sample when the moveable arm is in the first position.

The optical assembly of embodiments, wherein the first set of one or more optical elements comprises a first right angle mirror and a second right angle mirror, wherein the first right angle mirror and the second right angle mirror are in the first pathway and are arranged to reflect the light from the light source to be normally incident into the camera, The optical assembly of embodiments, wherein the light source is a point source to achieve interference imaging of transparent samples via illuminating the sample by a same wave front.

The optical assembly of embodiments, further comprising a second set of one or more optical elements mechanically coupled to the movable arm and arranged to receive light entering from the first aperture and redirect the light entering from the first aperture along a second pathway to obliquely illuminate the sample to provide fluorescence illumination of the sample when the moveable arm is in the second position, The optical assembly of embodiments, wherein the oblique angle is larger than a collecting angle of the lens configured to provide the field of view of the camera.

The optical assembly of embodiments, wherein the second set of one or more optical elements includes a mirror and an optical absorber, wherein the mirror reflects light to obliquely illuminate the sample and the optical absorber absorbs extraneous light from the first aperture that would otherwise pass through the second aperture of the enclosure and overwhelm the camera in the fluorescence excitation mode.

The optical assembly of embodiments, wherein the absorber absorbs light that is not incident on the mirror after going through the first aperture, wherein the light absorber is a thin-film light absorber.

The optical assembly of embodiments, further comprising a third set of one or more optical elements arranged to receive light entering from the first aperture and redirect the light entering into the second aperture in the movable arm and going along the first pathway toward a light diffuser on the movable arm to illuminate the sample in normal direction to measure the optical absorption of the sample.

The optical assembly of embodiments, wherein the third set of one or more optical elements includes a light diffuser, a first right angle mirror and a second right angle mirror, wherein the first right angle mirror and the second right angle mirror are in the first pathway and are arranged to reflect the light from the light source toward the light diffuser and then to be normally incident into the camera;

The optical assembly of embodiments, wherein the light diffuser is a semi-opaque diffuser with opacity in the range of 10% to 90%.

The optical assembly of embodiments, further comprising a rubber door to cover the sample receptacle to prevent ambient light from entering into the cavity.

The optical assembly of any of the preceding any embodiments, wherein the light source and the camera are positioned on the same side of the hand-held electronic device at a fixed distance to one another.

A system comprising: the optical assembly of any of the preceding any embodiments, and a mobile phone attachment comprising a first side configured to couple to the optical assembly and a second opposite side configured to couple to the hand-held electronic device, wherein the hand-held electronic device is a mobile phone.

The system of any embodiments, wherein the mobile phone attachment is exchangeable to provide attachment to different sized mobile phones.

The system of any embodiments, wherein a size of the mobile phone attachment is adjustable.

More Embodiments for Sizes and Weights

The adapter of any embodiment of the present disclosure can have a dimension (e.g., a length, a height, and/or a width) that is equal to or less than about 20 cm, equal to or less than about 15 cm, equal to or less than about 10 centimeters (cm), equal to or less than about 9 cm, equal to or less than about 8 cm, equal to or less than about 7 cm, equal to or less than about 6 cm, equal to or less than about 5 cm, equal to or less than about 4.5 cm, equal to or less than about 4 cm, equal to or less than about 3.5 cm, equal to or less than about 3 cm, equal to or less than about 2.5 cm, equal to or less than about 2 cm, equal to or less than about 1.5 cm, equal to or less than about 1 cm, or between a range of values thereof. For example, a width of an adapter can be equal to or less than about 4 cm. In another example, a height of the adapter can be equal to about 2 cm. In another example, a width of the adapter is less than about 2.5 cm. In yet another example, a length of the adapter can be between about 3 cm and about 5 cm.

The adapter of any embodiment of the present disclosure can have a volume that is equal to or less than about 400 cubic cm, equal to or less than about 350 cubic cm, equal to or less than about 300 cubic cm, equal to or less than about 250 cubic cm, equal to or less than about 200 cubic cm, equal to or less than about 150 cubic cm, equal to or less than about 125 cubic cm, equal to or less than about 100 cubic cm, equal to or less than about 90 cubic cm, equal to or less than about 80 cubic cm, equal to or less than about 70 cubic cm, equal to or less than about 60 cubic cm, equal to or less than about 50 cubic; cm, equal to or less than about 45 cubic cm, equal to or less than about 40 cubic cm, equal to or less than about 35 cubic cm, equal to or less than about 30 cubic cm, equal to or less than about 25 cubic cm, equal to or less than about 20 cubic cm, equal to or less than about 15 cubic cm, equal to or less than about 10 cubic cm, equal to or less than about 5 cubic cm, or between a range of values thereof. For ex-ample, a volume of an adapter can be equal to or less than about 35 cubic cm. In another example, a volume of the adapter can be equal to or less than about 25 cubic cm. In yet another example, a volume of the adapter can be between about 30 cubic cm and about 40 cubic cm.

The adapter of any embodiment of the present disclosure can have a mass that is equal to or less than about 400 grams, equal to or less than about 350 grams, equal to or less than about 300 grams, equal to or less than about 250 grams, equal to or less than about 200 grams, equal to or less than about 150 grams, equal to or less than about 125 grams, equal to or less than about 100 grams, equal to or less than about 90 grams, equal to or less than about 80 grams, equal to or less than about 70 grams, equal to or less than about 60 grams, equal to or less than about 50 grams, equal to or less than about 45 grams, equal to or less than about 40 grams, equal to or less than about 35 grams, equal to or less than about 30 grams, equal to or less than about 25 grams, equal to or less than about 20 grams, equal to or less than about 15 grams, equal to or less than about 10 grams, equal to or less than about 5 grams, or between a range of values thereof. For example, a mass of an adapter can be equal to or less than about 45 grams. In another example, a mass of the adapter can be equal to or less than about 40 grams. In yet another example, a mass of the adapter can be between about 35 grams and about 45 grams.

An optical assembly for a hand-held mobile electronic device, the optical assembly comprising:
an enclosure;
a cavity within the enclosure;
a plurality of optical elements within the cavity, wherein the plurality of optical elements are arranged to receive light entering from a first aperture in the enclosure and to redirect the light entering from the first aperture along a first pathway toward a second aperture in the enclosure;
a moveable arm configurable in at least two different positions within the enclosure, a moveable arm configurable in at least three different positions within the enclosure,
wherein the moveable arm comprises a light reflector portion to reflect light, wherein the moveable arm comprises a light diffuser to homogenize the light and break the coherence of the light,
wherein the moveable arm comprise an aperture aligned with the entrance aperture in the enclosure,
wherein, when the moveable arm is in a first position within the enclosure, the light reflector portion is positioned between an entrance aperture in the enclosure and the plurality of optical elements such that the light reflector portion blocks the light entering from the first opening from being incident on the plurality of optical elements, and
wherein, when the moveable arm is in a second position within the enclosure, the light entering from the first opening is incident on the plurality of optical elements, and wherein when the moveable arm is in a third position within the enclosure, the light entering from the first opening goes through an aperture on the moveable arm and then is incident on the light diffuser;

The optical assembly of any embodiments, comprising a slot on a side of the enclosure, wherein the slot is arranged to receive a sample substrate such that:
when the sample substrate is fully inserted within the slot and the moveable arm is in the second position within the enclosure, the first pathway intersects the sample substrate; and
when the sample substrate is fully inserted within the slot and moveable arm is in the first position within the enclosure, light reflected by the light reflector portion is redirected to the sample substrate; and
when the sample substrate is fully inserted within the slot and moveable arm is the third position within the enclosure, light goes along the first pathway toward a light diffuser and then illuminate on the sample substrate.

The optical assembly of any embodiments, wherein the moveable arm comprises a light absorber portion to absorb light that is not incident on the mirror after going through the first aperture.

The optical assembly of any embodiments, wherein the moveable arm comprises:
 a first receptacle positioned above the light reflector portion; and
 an optical filter seated in the receptacle; and a second receptacle positioned above the aperture portion; and a optical filter seated in the receptacle.

The optical assembly of any embodiments, wherein, when the moveable arm is in the first position, the optical filter seated in the receptacle is positioned to receive light entering from the first aperture in the enclosure; and when the moveable arm is in the third position, the optical filter seated in the receptacle is positioned to receive light entering from the first aperture in the enclosure.

The optical assembly of any embodiments, wherein, when the moveable arm is in the first position, the optical filter seated in the receptacle overlaps a region in which a portion of the sample substrate is located when the sample substrate is fully inserted within the slot.

A system comprising:
 the optical assembly of any embodiments; and
 a mobile phone attachment comprising a first side configured to couple to the optical assembly and comprising a second opposite side configured to couple to a mobile phone, wherein a size of the mobile phone attachment is adjustable.

An optical assembly attachable to a hand-held electronic device having a light source, a camera, and a computer processor, wherein the optical assembly is configured to enable microscopic imaging of a sample by the camera with illumination of the sample by light from the light source, the optical assembly comprising:
 a lens configured to provide a microscopic field of view for the camera;
 a receptacle for receiving the sample and positioning the sample within the microscopic field of view; and
 an optical fiber configured to receive the light from the light source and to illuminate the receptacle.

The optical assembly of any embodiments wherein, when the optical assembly is attached to the hand-held electronic device, the lens and the camera define an optical axis, and wherein the optical fiber circumscribes the optical axis.

The optical assembly of any embodiments wherein the optical fiber is ring-shaped.

The optical assembly of any embodiments wherein the optical fiber is a side-emitting fiber.

The optical assembly of any embodiments wherein the optical assembly comprises an enclosure defining the receptacle, wherein the ring-shaped fiber sits in a groove of the enclosure, wherein the enclosure comprises an aperture configured to align with the light source and both end faces of the ring-shape fiber to receive light from the light source.

The optical assembly of any embodiments, wherein the light emits from the side of the ring-shape fiber to illuminate the sample area right under the camera in the optical axis.

The optical assembly of any embodiments, wherein the optical assembly comprises an enclosure defining the receptacle, wherein the enclosure comprises a first aperture configured to align with the light source, and a first end face of the optical fiber is positioned in the first aperture to receive light from the light source.

The optical assembly of any embodiments wherein the enclosure comprises a second aperture configured to align with the camera, and wherein the optical fiber comprises a first end positioned in the first aperture and comprises a second end positioned in the second aperture.

The optical assembly of any embodiments wherein at least one of the first end face of the optical fiber and a second end face of the optical fiber is matted.

The optical assembly of any embodiments wherein when the optical assembly is attached to the hand-held electronic device, the optical fiber is tilted with respect to the light source, and
 wherein a second end face of the optical fiber is arranged to illuminate a region of the sample located directly beneath the lens.

The optical assembly of any embodiments wherein the optical assembly comprises an enclosure defining the receptacle, the enclosure comprises a groove, and the optical fiber is arranged in the groove.

An optical assembly attachable to a hand-held electronic device having a light source, a camera, and a computer processor, wherein the optical assembly is configured to enable microscopic fluorescence imaging of a sample by the camera with illumination of the sample by light from the light source, the optical assembly comprising:
 a lens configured to provide a microscopic field of view for the camera;
 a receptacle for receiving the sample and positioning the sample within the microscopic field of view;
 a mirror off-set from an optical axis of the lens and positioned to reflect light from the light source and illuminate the sample over a range of oblique angles with respect to the optical axis; and
 a wavelength filter positioned between the sample and the camera to pass fluorescence emitted by the sample in response to the oblique illumination.

The optical assembly of any embodiments wherein the lens is positioned on a front-side of the sample and the mirror is positioned to obliquely illuminate the sample from a back-side of the sample, wherein the oblique angle is larger than a collecting angle of the lens.

The optical assembly of any embodiments further comprising an optical absorber positioned on the optical axis adjacent the mirror to absorb light from the light source not reflected by the mirror.

The optical assembly of any embodiments wherein the mirror and the optical absorber are mounted on a common structure and tilted with respect to one another.

The optical assembly of any embodiments, further comprising a second wavelength filter positioned in a path of the illumination light between the light source and the mirror to select certain wavelengths for illuminating the sample.

The optical assembly of any of the preceding any embodiments, wherein the sample is supported by a sample holder comprising a planar structure, and wherein the receptacle is configured to position the planar structure to extend partially into a path of illumination light from the light source to couple illumination light into the planar structure.

The optical assembly of any embodiments 6, wherein the receptacle is configured to position the planar structure such that the path of illumination light is incident on an edge of the planar structure, wherein the edge extends along a plane that is normal to a plane comprising the field of view.

The optical assembly of any embodiments wherein the mirror is arranged to reflect the light to partially obliquely illuminate the sample from a back side of the planar structure and to partially illuminate an edge of the planar structure to couple illumination light into the planar structure.

The optical assembly of any embodiments further comprising a rubber door to cover the sample receptacle to prevent ambient light from entering the optical assembly and entering the camera. The optical assembly of any embodiments, wherein the planar structure is configured to waveguide the coupled illumination light to the sample to illuminate the sample and cause the sample to emit fluorescence.

The optical assembly of any embodiments further comprising the sample holder,

The optical assembly of any embodiments 6, wherein the sample is a liquid sample and the sample holder comprises first and second plates sandwiching the liquid sample.

The optical assembly of any of the preceding any embodiments, wherein the lens, the receptacle, the mirror, and the wavelength filter are supported in a common optical box and further comprising an exchangeable holder frame for attaching the optical box to the hand-held electronic device.

The optical assembly of any embodiments, wherein the light source and the camera are positioned on the same side of the hand-held electronic device and at fixed distance to one another.

The optical assembly of any embodiments, wherein the hand-held electronic device is a smart phone.

An apparatus comprising the optical assembly of any of the preceding any embodiments and the hand-held electronic device.

An optical assembly attachable to a hand-held electronic device having a light source, a camera, and a computer processor, the optical assembly configured to enable microscopic fluorescence imaging of a sample by the camera with illumination of the sample by light from the light source, the optical assembly comprising:
  a lens configured to provide a microscopic field of view for the camera;
  a receptacle for receiving the sample and positioning the sample within the microscopic field of view,
  wherein the sample is supported by a sample holder comprising a planar structure, and wherein the receptacle is configured to position the planar structure to extend partially into a path of illumination light from the light source to couple illumination light into the planar structure and cause the sample to emit fluorescence; and
  a wavelength filter positioned between the sample and the camera to pass fluorescence emitted by the sample in response to the illumination.

The optical assembly of any embodiments further comprising a rubber door to cover the sample receptacle to prevent ambient light entering the optical assembly through the receptacle.

The optical assembly of any embodiments wherein the planar structure is configured to waveguide the coupled illumination light to the sample to illuminate the sample and cause the sample to emit the fluorescence.

The optical assembly of any embodiments further comprising the sample holder,

The optical assembly of any embodiments wherein the sample is a liquid sample and the sample holder comprises first and second plates sandwiching the liquid sample.

The optical assembly of any embodiments, further comprising a second wavelength filter positioned in the path of the illumination light between the light source and the portion of the sample holder partially extending into the path of the light.

The optical assembly of any of the preceding any embodiments, wherein the lens, the receptacle, and the wavelength filter are supported in a common optical box and further comprising an exchangeable holder frame for attaching the optical box to the hand-held electronic device.

The optical assembly of any embodiments wherein the light source and the camera are positioned on the same side of the hand-held electronic device at a fixed distance to one another.

The optical assembly of any embodiments, wherein the hand-held electronic device is a smart phone.

An apparatus comprising the optical assembly of any of the preceding any embodiments and the hand-held electronic device.

An optical assembly attachable to a hand-held electronic device having a light source, a first camera module, a second camera module, and a computer processor, wherein the optical assembly is configured to enable microscopic imaging of a sample by the first camera and by the second camera with illumination of the sample by light from the light source, the optical assembly comprising:
  a first assembly lens configured to provide a first microscopic field of view for the first camera module;
  a second assembly lens configured to provide a second microscopic field of view for the second camera module; and
  a receptacle for receiving the sample and positioning the sample within the first microscopic field of view and within the second microscopic field of view.

The optical assembly of any embodiments, wherein the first camera module comprises a first internal lens and the second camera module comprises a second internal lens, wherein a first optical magnification provided by the first assembly lens and the first internal lens is the same as a second optical magnification provided by the second assembly lens and the second internal lens.

The optical assembly of any embodiments, wherein a first ratio of a focal length of the first assembly lens to a focal length of the first internal lens is equal to a second ratio of a focal length of the second assembly lens to a focal length of the second internal lens.

The optical assembly of any embodiments, wherein a first image resolution provided by the first camera module and the first assembly lens is the same as a second image resolution provided by the second camera module and the second assembly lens.

The optical assembly of any embodiments, wherein the first camera module comprises a first internal lens and the second camera module comprises a second internal lens, wherein a first optical magnification provided by the first assembly lens and the first internal lens is different from a second optical magnification provided by the second assembly lens and the second internal lens.

The optical assembly of any embodiments, wherein a first ratio of a focal length of the first assembly lens to a focal length of the first internal lens is less than a second ratio of a focal length of the second assembly lens to a focal length of the second internal lens.

The optical assembly of any embodiments, wherein a first image resolution provided by the first camera module and the first assembly lens is less than a second image resolution provided by the second camera module and the second assembly lens.

The optical assembly of any of the preceding any embodiments, wherein the first microscopic field of view overlaps with the second microscopic field of view.

The optical assembly of any embodiments, wherein an amount of overlap of the first microscopic field of view with the second microscopic field of view is between 1% and 90%.

The optical assembly of any of any embodiments, wherein the first microscopic field of view does not overlap with the second microscopic field of view.

The optical assembly of any of the preceding any embodiments, wherein each of the first assembly lens and the second assembly lens is arranged to receive light scattered by or emitted by the sample.

The optical assembly of any of the preceding any embodiments, wherein the first microscopic field of view is less than the second microscopic field of view.

The optical assembly of any of the preceding any embodiments, wherein an angular field of view of the first assembly lens is less than an angular field of view of the second assembly lens.

The optical assembly of any embodiments, wherein a ratio of the angular field of view of the first assembly lens to the angular field of the second assembly lens is between 1.1 and 1000.

The optical assembly of any of the preceding any embodiments, comprising:
  a first optical filter arranged in a first illumination path to or from the first assembly lens; and
  a second optical filter arranged in a second illumination path to or from the second assembly lens.

The optical assembly of any embodiments, wherein the first optical filter is configured to filter a first range of wavelengths, the second optical filter is configured to filter a second range of wavelengths, and the first range of wavelengths is different from the second range of wavelengths.

The optical assembly of any of the preceding any embodiments, comprising:
  a first polarizer arranged in a first illumination path to or from the first assembly lens; and
  a second polarizer arranged in a second illumination path to or from the second assembly lens.

The optical assembly of any embodiments, wherein the first polarizer and the second polarizer have different polarization dependent light transmission and blocking properties.

An apparatus comprising the optical assembly of any of the preceding any embodiments and the hand-held electronic device.

The apparatus of any embodiments, wherein the hand-held electronic device is a smart phone.

The apparatus of any embodiments, wherein the hand-held electronic device is configured to computationally merge a first image obtained from the first camera module with a second image obtained from the second camera module.

An imaging method comprising:
  compressing a sample between two plates, wherein the two plates are separated from one another by an array of spacers, at least one of which has a reference mark;
  acquiring multiple images of the sample using an imaging system comprising a camera and at least one lens, wherein each image corresponds to a different object plane within a thickness of the sample;
  computationally analyzing each image to determine information about the corresponding object plane based on one or more of the reference marks; and
  computationally constructing a three-dimensional image of the sample based on the multiple images and the information about the corresponding object planes.

The imaging method of any embodiments, wherein the determined information about the corresponding object plane comprises a depth of the object plane relative to imaging system.

The imaging method of any embodiments of any embodiments 2, wherein at least some of the spacers each have a reference mark.

The imaging method of any embodiments, wherein the determined information about the corresponding object plane comprises a depth and an orientation of the object plane relative to imaging system.

The imaging method of any of the preceding any embodiments, where the computational analyzing of each image comprises determining a degree of defocus of one or more of the reference marks.

The imaging method of any embodiments, where the computational analyzing of each image comprises determining a depth for each of multiple ones of the reference marks based on a degree of defocus for each such reference mark and determining a depth and an orientation of the corresponding object plane relative to the imaging system based on the determined depths of the reference marks.

The imaging method of any of the preceding any embodiments, wherein the references marks are not rotationally symmetric with respect to an axis perpendicular to at least one of the plates.

The imaging method of any embodiments, wherein the computational analyzing of each image comprises determining a rotational orientation of one or more of the reference marks about the axis relative to the imaging system.

The imaging method of any of the preceding any embodiments, wherein the computational analyzing of each image comprising comparing image information about the reference marks to a priori knowledge about the reference marks.

The imaging method of any embodiments, wherein the a priori knowledge about the reference marks is based on one or more of a shape of each reference mark and a location of each reference mark relative to the plates.

The imaging method of any of the preceding any embodiments, wherein the spacers are pillars.

The imaging method of any of the preceding any embodiments, wherein the acquiring of the multiple images comprises moving one or more components of the imaging system relative to the plates sandwiching the sample.

The imaging method of any of the preceding any embodiments, wherein the computational constructing of the three-dimensional image comprises processing each acquired image to remove out-of-focus features.

The imaging method of any embodiments, wherein the processing of each acquired image to remove out-of-focus features comprises using a band-pass filter.

The imaging method of any of the preceding any embodiments, where the acquired images correspond to interference images formed by combining light from the sample with reference light not directed to the sample on the camera.

An imaging apparatus comprising:
  an imaging system comprising a camera and at least one lens;
  a sample holder for supporting a sample cartridge relative to the imaging system, the sample cartridge comprising two plates are separated from one another by an array of spacers, at least one of which has a reference mark, wherein a sample to be imaged is configured to be compressed between the two plates; and a processing and control system coupled to the sample holder and the camera and configured to acquire multiple images of the sample using the imaging system, wherein each image corresponds to a different object plane within a thickness of the sample, and wherein the processing and control system is further configured to:

computationally analyze each image to determine information about the corresponding object plane based on one or more of the reference marks; and computationally construct a three-dimensional image of the sample based on the multiple images and the information about the corresponding object planes.

The imaging apparatus of any embodiments, wherein the determined information about the corresponding object plane comprises a depth of the object plane relative to imaging system.

The imaging apparatus of any embodiments or, wherein at least some of the spacers each have a reference mark.

The imaging apparatus of any embodiments, wherein the determined information about the corresponding object plane comprises a depth and an orientation of the object plane relative to imaging system.

The apparatus of any of the preceding any embodiments, where the computational analyzing of each image comprises determining a degree of defocus of one or more of the reference marks.

The apparatus of any embodiments 20, wherein the computational analyzing of each image comprises determining a depth for each of multiple ones of the reference marks based on a degree of defocus for each such reference mark and determining a depth and an orientation of the corresponding object plane relative to the imaging system based on the determined depths of the reference marks.

The apparatus of any of the preceding any embodiments, wherein the references marks are not rotationally symmetric with respect to an axis perpendicular to at least one of the plates.

The apparatus of any of embodiments, wherein the computational analyzing of each image comprises determining a rotational orientation of one or more of the reference marks about the axis relative to the imaging system.

The apparatus of any of the preceding any embodiments, wherein the computational analyzing of each image comprising comparing image information about the reference marks to a priori knowledge about the reference marks.

The apparatus of any embodiments, wherein the a priori knowledge about the reference marks is based on one or more of a shape of each reference mark and a location of each reference mark relative to the plates.

The apparatus of any of the preceding any embodiments, wherein the spacers are pillars.

The apparatus of any of the preceding any embodiments, wherein the control system is configured to move one or more components of the imaging system relative to the plates sandwiching the sample to acquire the multiple images.

The apparatus of any of the preceding any embodiments, wherein the computational constructing of the three-dimensional image comprises processing each acquired image to remove out-of-focus features.

The apparatus of any embodiments wherein the processing of each acquired image to remove out-of-focus features comprises using a band-pass filter.

The apparatus of any of the preceding any embodiments, wherein where the acquired images correspond to interference images formed by combining light from the sample with reference light not directed to the sample on the camera.

IV. Textured Surfaces

A. QMAX Colorimetric Assay with Textures Reflective Scattering Surfaces

In an assay involving a detection of light signal, such as colorimetric assay or fluorescence assay, a small container to hold a liquid sample and passes a light beam though the sample to measure the light or the color of the sample. When the sample is very thin, the light or color becomes faint and difficult measure.

The present invention provides, among other thing, solution to get a stronger optical signal in a thin sample.

One novelty of the present invention is to use QMAX card (that has two movable plates) to make a sample into a very uniform thin layer (less than 200 um).

Another novelty of the present invention is to use a textured reflective surface on a surface of one of the two plates to enhance an optical signal, particularly for colorimetric assay and/or fluorescence assay.

In the present invention, we observed that the color signal of a colorimetric assay can be significantly increased by using a reflective textured surface as one of the wall of the chamber can significantly increase the color signal.

According the present invention, a device uses to plates to sandwich a sample into a thin layer, wherein one of the plate is transparent and the other plate has a textured reflective surface on its sample contact area. The probing light enters the sample from the transparent plate, goes through the sample, and diffusively reflected by the textured surface back to the transparent plate. We have observed that such arrangement can significantly increase the color signal even the sample as thin as 30 um or less.

Furthermore, according to the present invention, the device further comprise a dry reagent coated on one of the plate, so that a liquid sample can dropped on one or both of the plate, close the plates, and then measurement. The sample thickness can be 150 um or less, making the dry regent mixed with the sample in a short time, to speed up the total measurement time.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF) that regulate the spacing between the plates. The term "X-plate" refers to one of the two plates in a CROF card, wherein the spacers are fixed to this plate. More descriptions of the COF Card, CROF Card, and X-plate are described in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

Figure 7A:
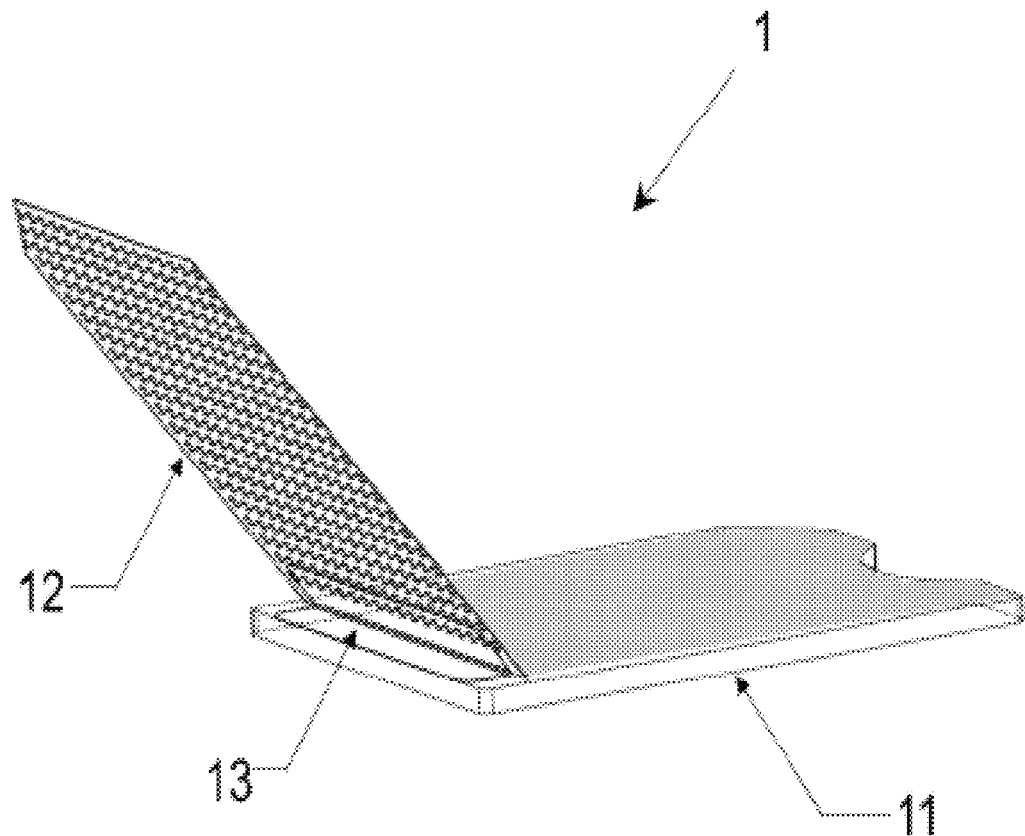
FIG. 7A illustrates an example of opened assembled sample handling device for assaying a sampling consisting of first plate, second plate and hinge according to one embodiment of the present invention.

FIG. 7A illustrates an example of opened assembled sample handling device 1 for assaying a sampling consisting of first plate 12, second plate 11 and hinge 13.

Figure 7B:
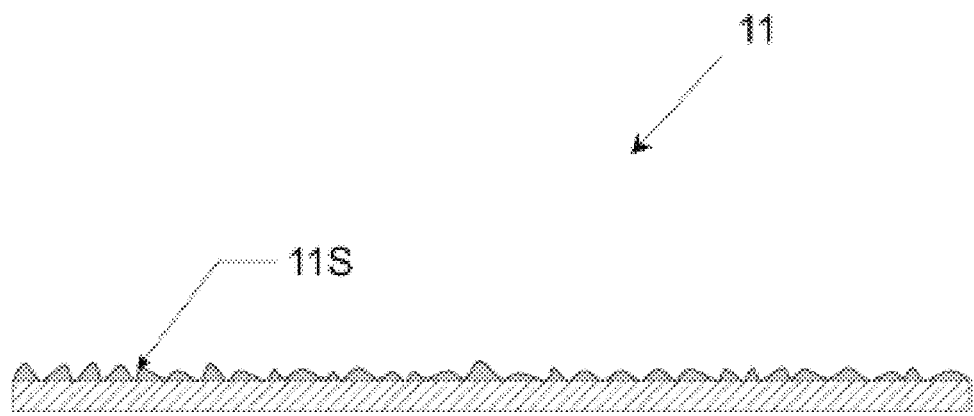
FIG. 7B illustrate an example of the second plate of the sample handling device having textured microstructures on top surface according to one embodiment of the present invention.

FIG. 7B illustrate an example of the second plate of the sample handling device having textured microstructures on top surface, in accordance with an embodiment of the present invention.

N1. In some embodiments, according to the present invention, a device for assaying a sample using optical signal, comprising:

a first plate, a second plate, spacers, and a textured surface, wherein:
  i. the first and second plates are movable relative to each other into different configurations;
  ii. one or both plates are flexible;
  iii. the second plate has, on its inner surface, have textured structures for scattering the light illuminated on the surface;
  iv. the textured surface can be, but is not limited to a bumpy, wavy roughly surface;
  v. the textured surface is periodic or aperiodic;
  vi. the textured surface's average roughness range is 0.5 um, 1 um, 2 um, 3 um, 5 um, 10 um, 15 um, 20 um, 25 um, 30 um, 50 um or within a range of any two of these values;
  vii. the textured surface's average roughness range is preferred to be, but is not limited to 1 um to 5 um;
  viii. the average roughness of textured surface is in the range of 1 μm to 120 μm.
  ix. the spacers are fixed to the inner surface of the first plate and have a predetermined uniform height;
  x. the preferred height of spacers is larger than the average roughness of the textured surface and smaller than 100 um;

wherein on of the configuration is an open configuration, in which: two plates are partially or entirely separated apart, the spacing between the plates is not regulated by the spacers, and the sample is deposited on one or both of the plates;

wherein on of the configuration is a closed configuration, which is configured after the sample deposition in the open configuration, and in the closed configuration: at least part of the deposited sample is compressed by the two plates into a continuous layer;

wherein the sample is in liquid form.

The textured surface of embodiments, wherein the dimensions of the textured surface can be described by the average roughness height ($R_a$), average lateral feature size ($b_a$) and average period ($p_a$) which are calculated based on a few parameters and explained as below:

1. Sampling length ($L_s$): It is the sampling length.
2. Actual profile ($A_f$): It is the profile of the actual surface measured on the textured surface.
3. Mean Profile ($M_f$): It is the profile, within $L_s$ such that the sum of the material-filled areas enclosed above it by the actual profile is equal to the sum of the material void area enclosed below it by the profile.
4. Lateral feature size ($b_i$): It is the lateral dimension of one profile pocket above or below the mean profile.
5. Period ($p_i$): It is the distance between two closest peaks between which there is at least one valley below the mean profile.

Definition of average roughness height ($R_a$), average lateral feature size ($b_a$) and average period ($p_a$):

1. Average roughness height ($R_a$): It is the arithmetic mean of the absolute value of the highest $h_i$ between the actual and mean profile, defined by the following formula:

$$R_a = \frac{\int_0^{L_s} |h_i| dx}{L_s}$$

2. Average lateral feature size ($b_a$): It is the average lateral dimension of all profile pockets above or below the mean profile within $L_s$, defined by the following formula:

$$b_a = \frac{\sum_1^n b_i}{n}$$

where n is the total number of profile pockets within $L_s$.

3. Average period ($p_a$): Within $L_s$, it is the average distance between two closest peaks between which there is at least one valley, defined by the following formula:

$$p_a = \frac{\sum_1^n p_i}{n}$$

where n is the total number of periods within $L_s$.

The textured surface of embodiments, wherein the average roughness height ($R_a$) need to be at least 20% of the wavelength of the illumination light and can be up to 5-fold of the spacing between the first plate and second plate, or in range between these two values.

The textured surface of embodiments, wherein the average lateral feature size ($b_a$) need to be at least 20% and up to 10-fold of the wavelength of the illumination light, or in range between these two values.

The textured surface of embodiments, wherein the average period ($b_a$) need to be at least 50% and up to 1000-fold of the wavelength of the illumination light, or in range between these two values.

Device_C1 (for Colorimetric Signal)

A sample handling device for enhancing optical signal (Q-card), comprising: A first plate, a second plate, spacers and textured surface, wherein:
  i. the plates are movable relative to each other into different configurations;
  ii. one or both plates are flexible;
  iii. the second plate has, on its inner surface, have textured structures for scattering the light illuminated on the surface;
  iv. the textured surface can be, but is not limited to a bumpy, wavy roughly surface;
  v. the textured surface can be periodic or aperiodic;
  vi. the textured surface's average roughness range is 0.5 um, 1 um, 2 um, 3 um, 5 um, 10 um, 15 um, 20 um, 25 um, 30 um, 50 um or within a range of any two of these values;

vii. the textured surface's average roughness range is preferred to be, but is not limited to 1 um to 5 um;
viii. the average roughness of textured surface is in the range of 1 μm to 120 μm.
ix. the spacers are fixed to the inner surface of the first plate and have a predetermined uniform height;
x. the preferred height of spacers is larger than the average roughness of the textured surface and smaller than 100 um;

wherein on of the configuration is an open configuration, in which: two plates are partially or entirely separated apart, the spacing between the plates is not regulated by the spacers, and the sample is deposited on one or both of the plates;
wherein on of the configuration is a closed configuration, which is configured after the sample deposition in the open configuration, and in the closed configuration: at least part of the deposited sample is compressed by the two plates into a continuous layer;
wherein the sample is in liquid form.

In some embodiments, the textured surface is made of opaque white material.

Device_C2 (for Colorimetric Signal)

A sample handling device for enhancing optical signal (Q-card), comprising:

A first plate, a second plate, spacers and textured surface, wherein:

i. the plates are movable relative to each other into different configurations;
ii. one or both plates are flexible;
iii. the second plate has, on its inner surface, have textured structures for scattering the light illuminated on the surface;
iv. the textured surface can be, but is not limited to a bumpy, wavy roughly surface;
v. the textured surface can be periodic or aperiodic;
vi. the textured surface's average roughness range is 0.5 um, 1 um, 2 um, 3 um, 5 um, 10 um, 15 um, 20 um, 25 um, 30 um, 50 um or within a range of any two of these values;
vii. the textured surface's average roughness range is preferred to be, but is not limited to 1 um to 5 um;
viii. the average roughness of textured surface is in the range of 1 μm to 120 μm.
ix. the spacers are fixed to the inner surface of the first plate and have a predetermined uniform height;
x. the preferred height of spacers is larger than the average roughness of the textured surface and smaller than 100 um;

wherein on of the configuration is an open configuration, in which: two plates are partially or entirely separated apart, the spacing between the plates is not regulated by the spacers, and the sample is deposited on one or both of the plates;
wherein on of the configuration is a closed configuration, which is configured after the sample deposition in the open configuration, and in the closed configuration: at least part of the deposited sample is compressed by the two plates into a continuous layer;
wherein the sample is liquid form.

In some embodiments, the textured surface is made of semi-opaque white material, and the transmissivity is 10%~30%.

Device F (for Fluorescent Signal)

A sample handling device for enhancing optical signal (Q-card), comprising:

A first plate, a second plate, spacers and textured surface, wherein:

i. the plates are movable relative to each other into different configurations;
ii. one or both plates are flexible;
iii. the second plate has, on its inner surface, have textured structures for scattering the light illuminated on the surface;
iv. the textured surface can be, but is not limited to a bumpy, wavy roughly surface;
v. the textured surface can be periodic or aperiodic;
vi. the textured surface's average roughness range is 0.5 um, 1 um, 2 um, 3 um, 5 um, 10 um, 15 um, 20 um, 25 um, 30 um, 50 um or within a range of any two of these values;
vii. the textured surface's average roughness range is preferred to be, but is not limited to 1 um to 5 um;
viii. the average roughness of textured surface is in the range of 1 μm to 120 μm.
ix. the spacers are fixed to the inner surface of the first plate and have a predetermined uniform height;
x. the preferred height of spacers is larger than the average roughness of the textured surface and smaller than 100 um;

wherein on of the configuration is an open configuration, in which: two plates are partially or entirely separated apart, the spacing between the plates is not regulated by the spacers, and the sample is deposited on one or both of the plates;
wherein on of the configuration is a closed configuration, which is configured after the sample deposition in the open configuration, and in the closed configuration: at least part of the deposited sample is compressed by the two plates into a continuous layer;
wherein the sample is in liquid form.

In some embodiments, the textured surface is made of opaque white material or coated with reflective metal film, the metal film can be, but is not limited to aluminum, silver and gold. The preferred thickness range of the metal film is preferred to be, but not limited to be 10 nm about 100 nm.

Figure 8A:
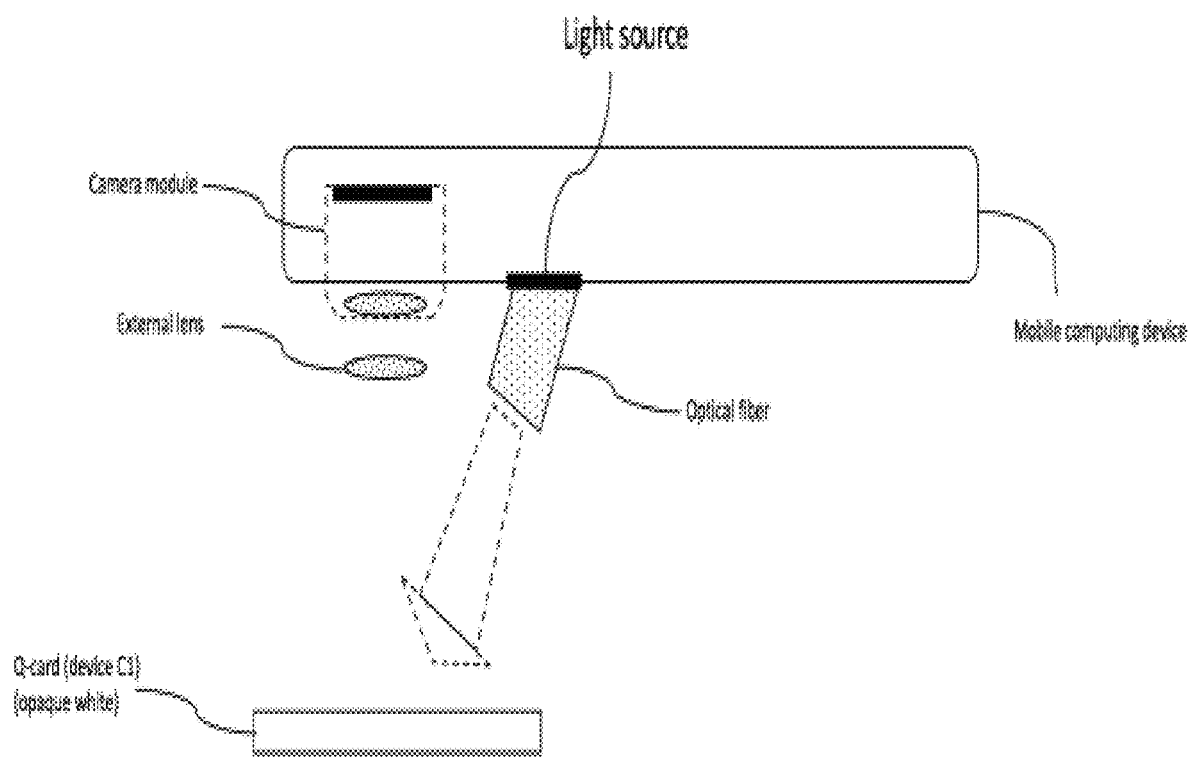
FIG. 8A illustrates the optical configuration of apparatus A1 for reading colorimetric signal of Device_C1.

FIG. 8A illustrates the optical configuration of apparatus A1 for reading colorimetric signal of Device_C1.

Figure 8B:
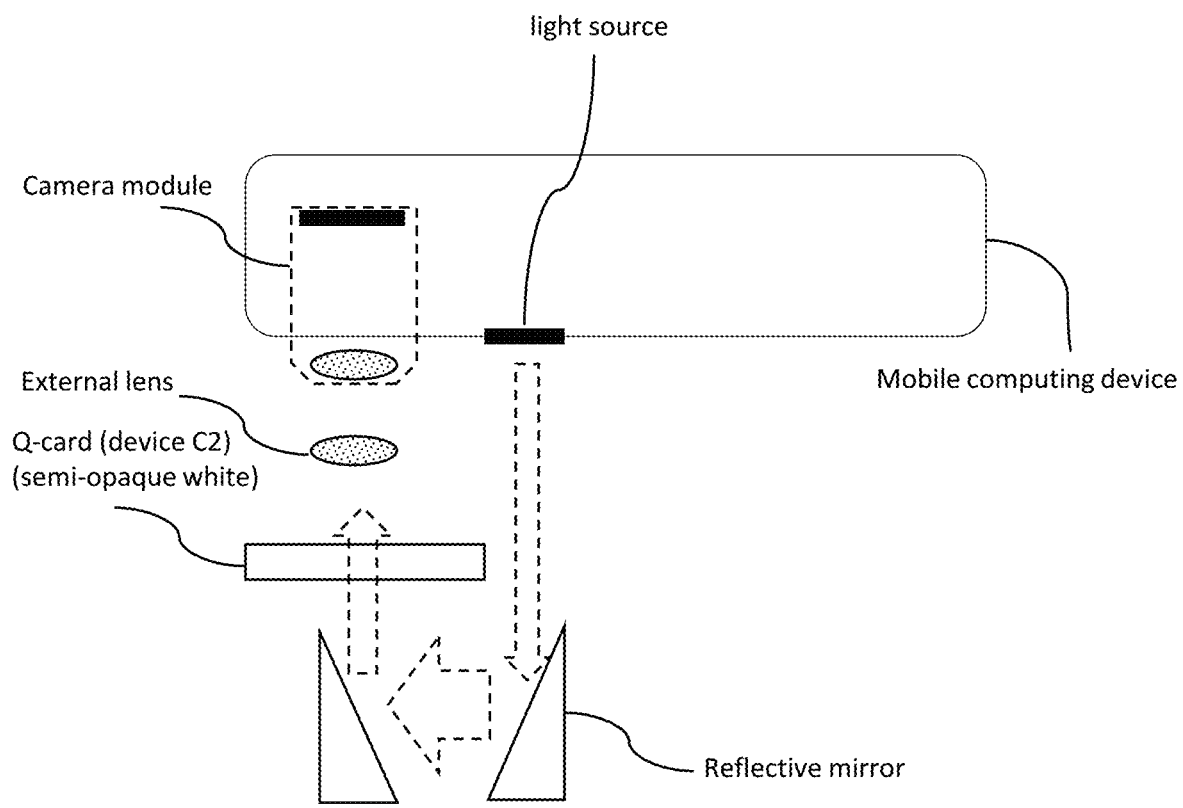
FIG. 8B illustrates the optical configuration of apparatus A2 for reading colorimetric signal of Device_C2.

FIG. 8B illustrates the optical configuration of apparatus A2 for reading colorimetric signal of Device_C2.

Figure 8C:
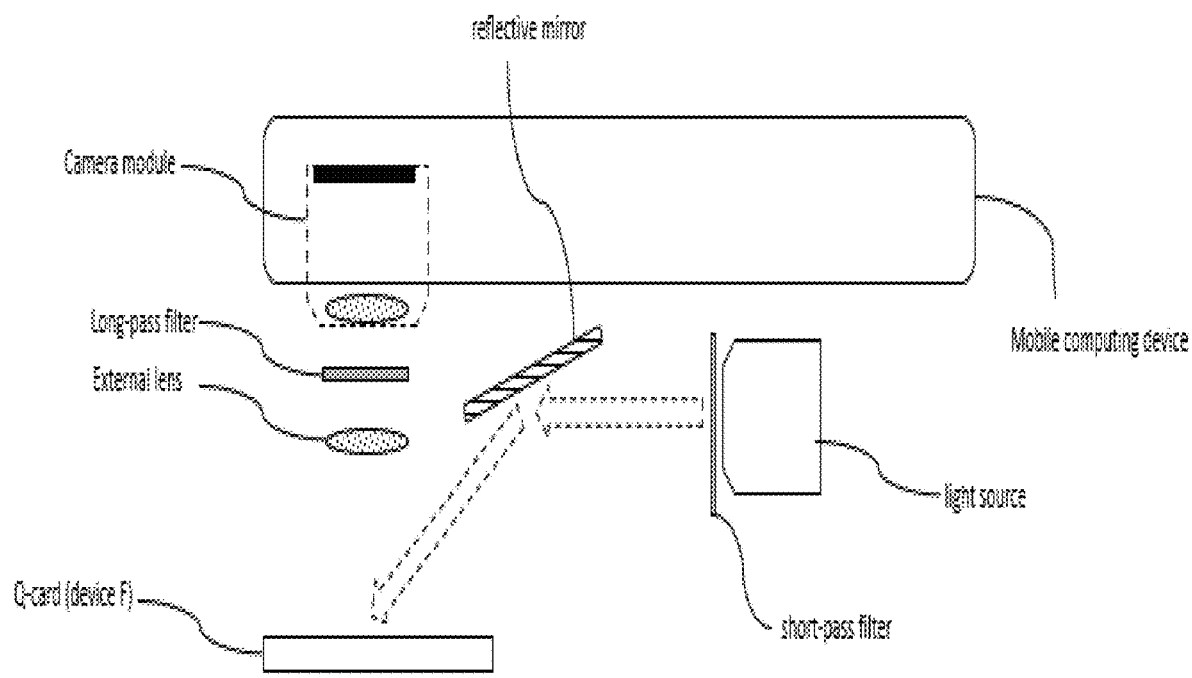
FIG. 8C illustrates the optical configuration of apparatus A3 for reading fluorescence signal of Device_F.

FIG. 8C illustrates the optical configuration of apparatus A3 for reading fluorescence signal of Device F.

Apparatus (for Colorimetric Signal).A1

A testing apparatus, comprising:
a) a sample handling device for enhancing optical signal (Device_C1), according to the above device claim;
b) a mobile computing device having a camera module and a light source;
c) an Illumination optics, comprising a tilted optical fiber;
d) an external lens;
wherein the light source emits white light;
wherein the light source and camera module are on the same face of the mobile computing device;
wherein the Q-card is put right under camera module, the preferred distance between them is 15 mm~20 mm;
wherein the external lens is put between the Q-card and camera module so that the sample in Q-card is in the working distance of camera module, and the preferred focal length of external lens is 12~18 mm, and the distance between lens and camera module is preferred to be as small as possible and no larger than 3 mm;

wherein the optical fiber guide the light emitted from the light source to illuminate on the sample area right under the camera module;

wherein one end face of the optical fiber is put under the aperture of the light source, and the distance between them is preferred to be as small as possible and no larger than 3 mm;

wherein the diameter of the optical fiber is configured to be equal to the diameter of the light source aperture;

wherein the tilt angle in which the optical fiber is mounted is set to make the center light beam emitted out from the fiber illuminate on the sample area right under the camera module.

Apparatus (for Colorimetric Signal).A2

A testing apparatus, comprising:
a) a sample handling device for enhancing optical signal (Device_C2), according to the above device claim;
b) a mobile computing device having a camera module and a light source;
c) an Illumination optics, comprising a pair of reflective mirrors;
d) an external lens;

wherein the light source emits white light;

wherein the light source and camera module are on the same face of the mobile computing device;

wherein the Q-card is put right under camera module, the preferred distance between them is 5~10 mm;

wherein the external lens is put between the Q-card and camera module so that the sample in Q-card is in the working distance of camera module, and the preferred focal length of external lens is 4~8 mm, and the preferred distance between lens and camera module is preferred to be as small as possible and no larger than 3 mm;

wherein the illumination optics turns the light emitted from the light source to back-illuminate the sample on Q-card, and each mirror turns the light by 90 degree;

wherein the mirrors are mounted under the Q-card, and one mirror is in a line with the light source, and another one is in a line with the camera module, and the preferred distance between the Q-card and mirrors is 5 mm~10 mm.

a) a mobile computing device having a camera module;
b) a separate light source;
c) an external lens;

Optical Signals

According the present invention, the optical signal that can by enhanced by the textured surfaces of the device of any prior embodiment, is selected from a group of colors in the sample, fluorescence, luminescence (electrical, chemical, photo, or electrical-chemical), and/or other light from emitters.

Apparatus for Fluorescent Signal).A3

A testing apparatus, comprising:
a) a sample handling device for enhancing optical signal (Device_F), according to the above device claim;
b) a mobile computing device having a camera module;
c) a separate light source;
d) an Illumination optics, comprising tilted reflective mirror;
e) filters, comprising a long pass filter and a short pass filter;
f) an external lens;

wherein the light source is a laser diode;

wherein the tilt mirror turns the light emitted from the light source to illuminate on the sample area right under the camera module;

wherein the light illuminates on the sample in an oblique angle, preferred angle is >60 degree;

wherein the Q-card is put right under camera module, the preferred distance between them is 15 mm~20 mm;

wherein the external lens is put between the Q-card and camera module so that the sample in Q-card is in the working distance of camera module, and the preferred focal length of external lens is 12 mm~18 mm, and the preferred distance between lens and camera module is preferred to be as small as possible and no larger than 3 mm;

wherein the short pass filter is put in front of the aperture of the light source;

wherein the long pass filter is put between the external lens and camera module.

Method

A method for analyzing the optical signal of sample, comprising the steps of:
a) collecting a sample liquid;
b) obtaining a device of any prior embodiment;
c) depositing the sample on one or both of the plates of the device when the plates are in an open configuration;
d) bringing the two plates together and pressing the plates into the closed configuration so that the sample forms a liquid layer between the two plates;
e) inserting the device into the testing apparatus;
f) turning on the light source of the testing apparatus;
g) using camera module capture an image of the sample; and
h) the mobile computing device process the image to analyze colorimetric or fluorescent signal of the image to get some property of the sample.

Application

The Q-card device, testing apparatus and the method above can be applied to detect presence and level of the analyte of interest in the following fields:

1) Food science and safety: testing pH, ammonia, nitrite, nitrate, heavy metal, bacteria level, etc. in drinking water; testing bacteria, lactose, additive, particular protein level, etc. in milk;
2) Personal health monitoring: glucose, alcohol, etc. in saliva, urine and breath.
3)

In some embodiments, a device for enhancing an optical signal in assaying comprises: a first plate, a second plate, spacers, and a light scattering layer, wherein:

i. the first and second plates are movable relative to each other into different configurations, and have, on its respective inner surface, a sample contact area for contacting a sample that contains an analyte;
ii. one or both of the plates are flexible;
iii. the first plate is transparent to the light, and
iv. the second plate substantially reflect light and comprises an inner surface a light scattering layer that has a rough topology;

wherein one of the configurations is an open configuration, in which the average spacing between the inner surfaces of the two plates is at least 200 um, and the sample is deposited on one or both of the plates;

wherein another of the configurations is a close configuration, which is configured after the sample deposition in the open configuration, and in the closed configuration: at least part of the sample is between the two plates and the average spacing between the inner surfaces of the plates is less than 200 um; and wherein in the closed configuration, the light scattering layer enhances trapping a probe light between the inner surface of the two plates.

In some embodiments, in the device, the light scattering surface of the second plate comprises:
  i. the textured surface can be, but is not limited to a bumpy, wavy roughly surface;
  ii. the textured surface can be periodic or aperiodic;
  iii. the textured surface's average roughness range is 0.5 um, 1 um, 2 um, 3 um, 5 um, 10 um, 15 um, 20 um, 25 um, 30 um, 50 um or within a range of any two of these values;
  iv. the textured surface's average roughness range is preferred to be, but is not limited to 1 um to 5 um; or
  v. the spacers are fixed to the inner surface of the first plate and have a predetermined uniform height; and
  vi. a combination of thereof.

C1. The device or system of any prior embodiments, wherein the light scattering layer can be made of highly reflectively opaque white material with reflectivity at least 50%, 60%, 70%, 80%, 90%, 100%, or in a range between any of the two values.

C2. The device or system of any prior embodiments, wherein the reflection spectrum of the light scattering surface is within the range of 300 nm to 1000 nm.

C3. The device or system of any prior embodiments, wherein the light scattering layer can be made of semi-opaque white material, and the transmissivity is 10%~30%.

C4. The device or system of any prior embodiments, wherein the light scattering layer can be made of reflective metal film, wherein the light scattering layer can be made of opaque white dielectric film.

C5. The device or system of any prior embodiments, wherein the light scattering layer has textured surfaces with $R_a$ (arithmetic average roughness) of 0.5 um~200 um, $R_{sm}$ (mean spacing of the asperities) of >0.5 um and $R\Delta_a$ (average slop of the profile)>0.1

C6. The device or system of any prior embodiments, wherein the textured surface can be periodic or aperiodic, wherein the shape of a single feature on the textured surface can be but not limited to square, triangle, sharp corner.

C7. The device or system of any prior embodiments, wherein the height of spacers is larger than the average roughness of the textured surface and smaller than 200 um.

The device or system of any prior embodiments, the average roughness height ($R_a$) of the textured reflective need to be at least 20% of the wavelength of the illumination light and can be up to 5-fold of the spacing between the first plate and second plate, or in range between these two values;

The device or system of any prior embodiments, the average lateral feature size ($b_a$) need to be at least 20% and up to 10-fold of the wavelength of the illumination light, or in range between these two values;

The device or system of any prior embodiments, the average period ($b_a$) need to be at least 50% and up to 1000-fold of the wavelength of the illumination light, or in range between these two values.

The height of the random scattering structures is from 1 nm to 200 nm, from 1 nm to 300 nm, and from 1 nm to 5000 nm.

In some embodiments, the reflection surface can be done by random nanoparticles of the same size or different size.

In some embodiments, the reflective range from 50% to 100%, from 30% to 100% and from 50% to 80%. They are either wide band or narrow band in spectrum.

1. Samples

The devices, apparatus, systems, and methods herein disclosed can be used for samples such as but not limited to diagnostic samples, clinical samples, environmental samples and foodstuff samples. The types of sample include but are not limited to the samples listed, described and/or summarized in PCT Application (designating U.S.) Nos. PCT/US2016/045437 and PCT/US0216/051775, which were respectively filed on Aug. 10, 2016 and Sep. 14, 2016, and are hereby incorporated by reference by their entireties.

For example, in some embodiments, the devices, apparatus, systems, and methods herein disclosed are used for a sample that includes cells, tissues, bodily fluids and/or a mixture thereof. In some embodiments, the sample comprises a human body fluid. In some embodiments, the sample comprises at least one of cells, tissues, bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, and exhaled breath condensate.

In some embodiments, the devices, apparatus, systems, and methods herein disclosed are used for an environmental sample that is obtained from any suitable source, such as but not limited to: river, lake, pond, ocean, glaciers, icebergs, rain, snow, sewage, reservoirs, tap water, drinking water, etc.; solid samples from soil, compost, sand, rocks, concrete, wood, brick, sewage, etc.; and gaseous samples from the air, underwater heat vents, industrial exhaust, vehicular exhaust, etc. In certain embodiments, the environmental sample is fresh from the source; in certain embodiments, the environmental sample is processed. For example, samples that are not in liquid form are converted to liquid form before the subject devices, apparatus, systems, and methods are applied.

In some embodiments, the devices, apparatus, systems, and methods herein disclosed are used for a foodstuff sample, which is suitable or has the potential to become suitable for animal consumption, e.g., human consumption. In some embodiments, a foodstuff sample includes raw ingredients, cooked or processed food, plant and animal sources of food, preprocessed food as well as partially or fully processed food, etc. In certain embodiments, samples that are not in liquid form are converted to liquid form before the subject devices, apparatus, systems, and methods are applied.

The subject devices, apparatus, systems, and methods can be used to analyze any volume of the sample. Examples of the volumes include, but are not limited to, about 10 mL or less, 5 mL or less, 3 mL or less, 1 microliter (μL, also "uL" herein) or less, 500 μL or less, 300 μL or less, 250 μL or less, 200 μL or less, 170 μL or less, 150 μL or less, 125 μL or less, 100 μL or less, 75 μL or less, 50 μL or less, 25 μL or less, 20 μL or less, 15 μL or less, 10 μL or less, 5 μL or less, 3 μL or less, 1 μL or less, 0.5 μL or less, 0.1 μL or less, 0.05 μL or less, 0.001 μL or less, 0.0005 μL or less, 0.0001 μL or less, 10 μL or less, 1 μL or less, or a range between any two of the values.

In some embodiments, the volume of the sample includes, but is not limited to, about 100 μL or less, 75 μL or less, 50 μL or less, 25 μL or less, 20 μL or less, 15 μL or less, 10 μL or less, 5 μL or less, 3 μL or less, 1 μL or less, 0.5 μL or less, 0.1 μL or less, 0.05 μL or less, 0.001 μL or less, 0.0005 μL or less, 0.0001 μL or less, 10 μL or less, 1 μL or less, or a range between any two of the values. In some embodiments, the volume of the sample includes, but is not limited to, about 10 µL or less, 5 µL or less, 3 µL or less, 1 µL or less, 0.5 µL or less, 0.1 µL or less, 0.05 µL or less, 0.001 µL or less, 0.0005 µL or less, 0.0001 µL or less, 10 µL or less, 1 µL or less, or a range between any two of the values.

In some embodiments, the amount of the sample is about a drop of liquid. In certain embodiments, the amount of sample is the amount collected from a pricked finger or fingerstick. In certain embodiments, the amount of sample is the amount collected from a microneedle, micropipette or a venous draw.

In certain embodiments, the sample holder is configured to hold a fluidic sample. In certain embodiments, the sample holder is configured to compress at least part of the fluidic sample into a thin layer. In certain embodiments, the sample holder comprises structures that are configured to heat and/or cool the sample. In certain embodiments, the heating source provides electromagnetic waves that can be absorbed by certain structures in the sample holder to change the temperature of the sample. In certain embodiments, the signal sensor is configured to detect and/or measure a signal from the sample. In certain embodiments, the signal sensor is configured to detect and/or measure an analyte in the sample. In certain embodiments, the heat sink is configured to absorb heat from the sample holder and/or the heating source. In certain embodiments, the heat sink comprises a chamber that at least partly enclose the sample holder.

2. Applications

The devices, apparatus, systems, and methods herein disclosed can be used in various types of biological/chemical sampling, sensing, assays and applications, which include the applications listed, described and/or summarized in PCT Application (designating U.S.) No. PCT/US2016/045437, which was filed on Aug. 10, 2016, and is hereby incorporated by reference by its entirety.

In some embodiments, the devices, apparatus, systems, and methods herein disclosed are used in a variety of different application in various field, wherein determination of the presence or absence, quantification, and/or amplification of one or more analytes in a sample are desired. For example, in certain embodiments the subject devices, apparatus, systems, and methods are used in the detection of proteins, peptides, nucleic acids, synthetic compounds, inorganic compounds, organic compounds, bacteria, virus, cells, tissues, nanoparticles, and other molecules, compounds, mixtures and substances thereof. The various fields in which the subject devices, apparatus, systems, and methods can be used include, but are not limited to: diagnostics, management, and/or prevention of human diseases and conditions, diagnostics, management, and/or prevention of veterinary diseases and conditions, diagnostics, management, and/or prevention of plant diseases and conditions, agricultural uses, veterinary uses, food testing, environments testing and decontamination, drug testing and prevention, and others.

The applications of the present invention include, but are not limited to: (a) the detection, purification, quantification, and/or amplification of chemical compounds or biomolecules that correlates with certain diseases, or certain stages of the diseases, e.g., infectious and parasitic disease, injuries, cardiovascular disease, cancer, mental disorders, neuropsychiatric disorders and organic diseases, e.g., pulmonary diseases, renal diseases, (b) the detection, purification, quantification, and/or amplification of cells and/or microorganism, e.g., virus, fungus and bacteria from the environment, e.g., water, soil, or biological samples, e.g., tissues, bodily fluids, (c) the detection, quantification of chemical compounds or biological samples that pose hazard to food safety, human health, or national security, e.g. toxic waste, anthrax, (d) the detection and quantification of vital parameters in medical or physiological monitor, e.g., glucose, blood oxygen level, total blood count, (e) the detection and quantification of specific DNA or RNA from biological samples, e.g., cells, viruses, bodily fluids, (f) the sequencing and comparing of genetic sequences in DNA in the chromosomes and mitochondria for genome analysis or (g) the detection and quantification of reaction products, e.g., during synthesis or purification of pharmaceuticals.

In some embodiments, the subject devices, apparatus, systems, and methods are used in the detection of nucleic acids, proteins, or other molecules or compounds in a sample. In certain embodiments, the devices, apparatus, systems, and methods are used in the rapid, clinical detection and/or quantification of one or more, two or more, or three or more disease biomarkers in a biological sample, e.g., as being employed in the diagnosis, prevention, and/or management of a disease condition in a subject. In certain embodiments, the devices, apparatus, systems, and methods are used in the detection and/or quantification of one or more, two or more, or three or more environmental markers in an environmental sample, e.g. sample obtained from a river, ocean, lake, rain, snow, sewage, sewage processing runoff, agricultural runoff, industrial runoff, tap water or drinking water. In certain embodiments, the devices, apparatus, systems, and methods are used in the detection and/or quantification of one or more, two or more, or three or more foodstuff marks from a food sample obtained from tap water, drinking water, prepared food, processed food or raw food.

In some embodiments, the subject device is part of a microfluidic device. In some embodiments, the subject devices, apparatus, systems, and methods are used to detect a fluorescence or luminescence signal. In some embodiments, the subject devices, apparatus, systems, and methods include, or are used together with, a communication device, such as but not limited to: mobile phones, tablet computers and laptop computers. In some embodiments, the subject devices, apparatus, systems, and methods include, or are used together with, an identifier, such as but not limited to an optical barcode, a radio frequency ID tag, or combinations thereof.

In some embodiments, the sample is a diagnostic sample obtained from a subject, the analyte is a biomarker, and the measured amount of the analyte in the sample is diagnostic of a disease or a condition. In some embodiments, the subject devices, systems and methods further include receiving or providing to the subject a report that indicates the measured amount of the biomarker and a range of measured values for the biomarker in an individual free of or at low risk of having the disease or condition, wherein the measured amount of the biomarker relative to the range of measured values is diagnostic of a disease or condition.

In some embodiments, the sample is an environmental sample, and wherein the analyte is an environmental marker. In some embodiments, the subject devices, systems and methods includes receiving or providing a report that indicates the safety or harmfulness for a subject to be exposed to the environment from which the sample was obtained. In some embodiments, the subject devices, systems and methods include sending data containing the measured amount of the environmental marker to a remote location and receiving a report that indicates the safety or harmfulness for a subject to be exposed to the environment from which the sample was obtained.

In some embodiments, the sample is a foodstuff sample, wherein the analyte is a foodstuff marker, and wherein the amount of the foodstuff marker in the sample correlate with safety of the foodstuff for consumption. In some embodiments, the subject devices, systems and methods include receiving or providing a report that indicates the safety or harmfulness for a subject to consume the foodstuff from which the sample is obtained. In some embodiments, the subject devices, systems and methods include sending data containing the measured amount of the foodstuff marker to a remote location and receiving a report that indicates the safety or harmfulness for a subject to consume the foodstuff from which the sample is obtained.

3. Analytes, Biomarkers, and Diseases

The devices, apparatus, systems, and methods herein disclosed can be used for the detection, purification and/or quantification of various analytes. In some embodiments, the analytes are biomarkers that associated with various diseases. In some embodiments, the analytes and/or biomarkers are indicative of the presence, severity, and/or stage of the diseases. The analytes, biomarkers, and/or diseases that can be detected and/or measured with the devices, apparatus, systems, and/or method of the present invention include the analytes, biomarkers, and/or diseases listed, described and/or summarized in PCT Application (designating U.S.) Nos. PCT/US2016/045437 filed on Aug. 10, 2016, and PCT Application No. PCT/US2016/054025 filed on Sep. 27, 2016, and U.S. Provisional Application Nos. 62/234,538 filed on Sep. 29, 2015, 62/233,885 filed on Sep. 28, 2015, 62/293,188 filed on Feb. 9, 2016, and 62/305,123 filed on Mar. 8, 2016, which are all hereby incorporated by reference by their entireties. For example, the devices, apparatus, systems, and methods herein disclosed can be used in (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals.

In some embodiments, the analyte can be a biomarker, an environmental marker, or a foodstuff marker. The sample in some instances is a liquid sample, and can be a diagnostic sample (such as saliva, serum, blood, sputum, urine, sweat, lacrima, semen, or mucus); an environmental sample obtained from a river, ocean, lake, rain, snow, sewage, sewage processing runoff, agricultural runoff, industrial runoff, tap water or drinking water; or a foodstuff sample obtained from tap water, drinking water, prepared food, processed food or raw food.

In any embodiment, the sample can be a diagnostic sample obtained from a subject, the analyte can be a biomarker, and the measured the amount of the analyte in the sample can be diagnostic of a disease or a condition.

In any embodiment, the devices, apparatus, systems, and methods in the present invention can further include diagnosing the subject based on information including the measured amount of the biomarker in the sample. In some cases, the diagnosing step includes sending data containing the measured amount of the biomarker to a remote location and receiving a diagnosis based on information including the measurement from the remote location.

In any embodiment, the biomarker can be selected from Tables B1, 2, 3 or 7 as disclosed in U.S. Provisional Application Nos. 62/234,538, 62/293,188, and/or 62/305,123, and/or PCT Application No. PCT/US2016/054,025, which are all incorporated in their entireties for all purposes. In some instances, the biomarker is a protein selected from Tables B1, 2, or 3. In some instances, the biomarker is a nucleic acid selected from Tables B2, 3 or 7. In some instances, the biomarker is an infectious agent-derived biomarker selected from Table B2. In some instances, the biomarker is a microRNA (miRNA) selected from Table B7.

In any embodiment, the applying step b) can include isolating miRNA from the sample to generate an isolated miRNA sample, and applying the isolated miRNA sample to the disk-coupled dots-on-pillar antenna (QMAX device) array.

In any embodiment, the QMAX device can contain a plurality of capture agents that each bind to a biomarker selected from Tables B1, B2, B3 and/or B7, wherein the reading step d) includes obtaining a measure of the amount of the plurality of biomarkers in the sample, and wherein the amount of the plurality of biomarkers in the sample is diagnostic of a disease or condition.

In any embodiment, the capture agent can be an antibody epitope and the biomarker can be an antibody that binds to the antibody epitope. In some embodiments, the antibody epitope includes a biomolecule, or a fragment thereof, selected from Tables B4, B5 or B6. In some embodiments, the antibody epitope includes an allergen, or a fragment thereof, selected from Table B5. In some embodiments, the antibody epitope includes an infectious agent-derived biomolecule, or a fragment thereof, selected from Table B6.

In any embodiment, the QMAX device can contain a plurality of antibody epitopes selected from Tables B4, B5 and/or B6, wherein the reading step d) includes obtaining a measure of the amount of a plurality of epitope-binding antibodies in the sample, and wherein the amount of the plurality of epitope-binding antibodies in the sample is diagnostic of a disease or condition.

In any embodiment, the sample can be an environmental sample, and wherein the analyte can be an environmental marker. In some embodiments, the environmental marker is selected from Table B8 in U.S. Provisional Application No. 62/234,538 and/or PCT Application No. PCT/US2016/054025.

In any embodiment, the method can include receiving or providing a report that indicates the safety or harmfulness for a subject to be exposed to the environment from which the sample was obtained.

In any embodiment, the method can include sending data containing the measured amount of the environmental marker to a remote location and receiving a report that indicates the safety or harmfulness for a subject to be exposed to the environment from which the sample was obtained.

In any embodiment, the QMAX device array can include a plurality of capture agents that each binds to an environmental marker selected from Table B8, and wherein the reading step d) can include obtaining a measure of the amount of the plurality of environmental markers in the sample.

In any embodiment, the sample can be a foodstuff sample, wherein the analyte can be a foodstuff marker, and wherein the amount of the foodstuff marker in the sample can correlate with safety of the foodstuff for consumption. In some embodiments, the foodstuff marker is selected from Table B9.

In any embodiment, the method can include receiving or providing a report that indicates the safety or harmfulness for a subject to consume the foodstuff from which the sample is obtained.

In any embodiment, the method can include sending data containing the measured amount of the foodstuff marker to a remote location and receiving a report that indicates the safety or harmfulness for a subject to consume the foodstuff from which the sample is obtained.

In any embodiment, the devices, apparatus, systems, and methods herein disclosed can include a plurality of capture agents that each binds to a foodstuff marker selected from Table B9 from in U.S. Provisional Application No. 62/234,538 and PCT Application No. PCT/US2016/054025, wherein the obtaining can include obtaining a measure of the amount of the plurality of foodstuff markers in the sample, and wherein the amount of the plurality of foodstuff marker in the sample can correlate with safety of the foodstuff for consumption.

Also provided herein are kits that find use in practicing the devices, systems and methods in the present invention.

The amount of sample can be about a drop of a sample. The amount of sample can be the amount collected from a pricked finger or fingerstick. The amount of sample can be the amount collected from a microneedle or a venous draw.

A sample can be used without further processing after obtaining it from the source, or can be processed, e.g., to enrich for an analyte of interest, remove large particulate matter, dissolve or resuspend a solid sample, etc.

Any suitable method of applying a sample to the QMAX device can be employed. Suitable methods can include using a pipette, dropper, syringe, etc. In certain embodiments, when the QMAX device is located on a support in a dipstick format, as described below, the sample can be applied to the QMAX device by dipping a sample-receiving area of the dipstick into the sample.

A sample can be collected at one time, or at a plurality of times. Samples collected over time can be aggregated and/or processed (by applying to a QMAX device and obtaining a measurement of the amount of analyte in the sample, as described herein) individually. In some instances, measurements obtained over time can be aggregated and can be useful for longitudinal analysis over time to facilitate screening, diagnosis, treatment, and/or disease prevention.

Washing the QMAX device to remove unbound sample components can be done in any convenient manner, as described above. In certain embodiments, the surface of the QMAX device is washed using binding buffer to remove unbound sample components.

Detectable labeling of the analyte can be done by any convenient method. The analyte can be labeled directly or indirectly. In direct labeling, the analyte in the sample is labeled before the sample is applied to the QMAX device. In indirect labeling, an unlabeled analyte in a sample is labeled after the sample is applied to the QMAX device to capture the unlabeled analyte, as described below.

4. Labels

The devices, apparatus, systems, and methods herein disclosed can be used with various types of labels, which include the labels disclosed, described and/or summarized in PCT Application (designating U.S.) No. PCT/US2016/045437, which was filed on Aug. 10, 2016, and is hereby incorporated by reference by its entirety.

In some embodiments, the label is optically detectable, such as but not limited to a fluorescence label. In some embodiments, the labels include, but are not limited to, IRDye800CW, Alexa 790, Dylight 800, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoylcarbocyanine iodide), tetrabromorhodamine 123, rhodamine 6G, TMRM (tetramethyl rhodamine methyl ester), TMRE (tetramethyl rhodamine ethyl ester), tetramethylrosamine, rhodamine B and 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2'disulfonic acid; acridine and derivatives, such as acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; cascade blue; Brilliant Yellow; coumarin and derivatives: coumarin, 7-amino-4-methylcoumarin (AMC, Coumarin 120),7-amino-4-trifluoromethylcoumarin (Coumarin 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM),5-(4,6-dichlorotriazin-2-yl)amino-fluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Ciba-cron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl hodamine isothiocyanate (TRITC); riboflavin; 5-(2'-aminoethyl) aminonaphthalene-1-sulfonic acid (EDANS), 4-(4'-dimethylaminophenylazo)benzoic acid (DABCYL); rosolic acid; CAL Fluor Orange 560; terbium chelate derivatives; Cy 3; Cy 5; Cy 5.5; Cy 7; IRD 700; IRD 800; La Jolla Blue; phthalo cyanine;

and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, fluorescent europium and terbium complexes; combinations thereof, and the like. Suitable fluorescent proteins and chromogenic proteins include, but are not limited to, a green fluorescent protein (GFP), including, but not limited to, a GFP derived from *Aequoria victoria* or a derivative thereof, e.g., a "humanized" derivative such as Enhanced GFP; a GFP from another species such as *Renilla reniformis, Renilla mulleri*, or *Ptilosarcus guernyi*; "humanized" recombinant GFP (hrGFP); any of a variety of fluorescent and colored proteins from *Anthozoan* species; combinations thereof; and the like.

5. QMAX Device

The devices, apparatus, systems, and methods herein disclosed can include or use a QMAX device ((Q: quantification; M: magnifying; A: adding reagents; X: acceleration; also known as Q-card in some embodiments or compressed regulated open flow (CROF) device), which include the QMAX device listed, described and/or summarized in PCT Application (designating U.S.) Nos. PCT/US2016/045437 filed on Aug. 10, 2016, and U.S. Provisional Application Nos. 62,431,639 filed on Dec. 9, 2016 and 62/456,287 filed on Feb. 8, 2017, which are all hereby incorporated by reference by their entireties.

As used here, the terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF) that regulate the spacing between the plates. The term "X-plate" refers to one of the two plates in a CROF card, wherein the spacers are fixed to this plate. More descriptions of the COF Card, CROF Card, and X-plate are described in the provisional application Ser. No. 62/456,065, filed on Feb. 7, 2017, which is incorporated herein in its entirety for all purposes.

The term "compressed open flow (COF)" refers to a method that changes the shape of a flowable sample deposited on a plate by (i) placing other plate on top of at least a part of the sample and (ii) then compressing the sample between the two plates by pushing the two plates towards each other; wherein the compression reduces a thickness of at least a part of the sample and makes the sample flow into open spaces between the plates. The term "compressed regulated open flow" or "CROF" (or "self-calibrated compressed open flow" or "SCOF" or "SCCOF") (also known as QMAX) refers to a particular type of COF, wherein the final thickness of a part or entire sample after the compression is "regulated" by spacers, wherein the spacers are placed between the two plates. Here the CROF device is used interchangeably with the QMAX card.

The term "open configuration" of the two plates in a QMAX process means a configuration in which the two plates are either partially or completely separated apart and the spacing between the plates is not regulated by the spacers The term "closed configuration" of the two plates in a QMAX process means a configuration in which the plates are facing each other, the spacers and a relevant volume of the sample are between the plates, the relevant spacing between the plates, and thus the thickness of the relevant volume of the sample, is regulated by the plates and the spacers, wherein the relevant volume is at least a portion of an entire volume of the sample.

The term "a sample thickness is regulated by the plate and the spacers" in a QMAX process means that for a give condition of the plates, the sample, the spacer, and the plate compressing method, the thickness of at least a port of the sample at the closed configuration of the plates can be predetermined from the properties of the spacers and the plate.

The term "inner surface" or "sample surface" of a plate in a QMAX card refers to the surface of the plate that touches the sample, while the other surface (that does not touch the sample) of the plate is termed "outer surface".

The term "height" or "thickness" of an object in a QMAX process refers to, unless specifically stated, the dimension of the object that is in the direction normal to a surface of the plate. For example, spacer height is the dimension of the spacer in the direction normal to a surface of the plate, and the spacer height and the spacer thickness means the same thing.

The term "area" of an object in a QMAX process refers to, unless specifically stated, the area of the object that is parallel to a surface of the plate. For example, spacer area is the area of the spacer that is parallel to a surface of the plate.

The term of QMAX card refers the device that perform a QMAX (e.g. CROF) process on a sample, and have or not have a hinge that connect the two plates.

The term "QMAX card with a hinge and "QMAX card" are interchangeable.

The term "angle self-maintain", "angle self-maintaining", or "rotation angle self-maintaining" refers to the property of the hinge, which substantially maintains an angle between the two plates, after an external force that moves the plates from an initial angle into the angle is removed from the plates.

In using QMAX card, the two plates need to be open first for sample deposition. However, in some embodiments, the QMAX card from a package has the two plates are in contact each other (e.g. a close position), and to separate them is challenges, since one or both plates are very thing. To facilitate an opening of the QMAX card, opening notch or notches are created at the edges or corners of the first plate or both places, and, at the close position of the plates, a part of the second plate placed over the opening notch, hence in the notch of the first plate, the second plate can be lifted open without a blocking of the first plate.

In the QMAX assay platform, a QMAX card uses two plates to manipulate the shape of a sample into a thin layer (e.g. by compressing). In certain embodiments, the plate manipulation needs to change the relative position (termed: plate configuration) of the two plates several times by human hands or other external forces. There is a need to design the QMAX card to make the hand operation easy and fast.

In QMAX assays, one of the plate configurations is an open configuration, wherein the two plates are completely or partially separated (the spacing between the plates is not controlled by spacers) and a sample can be deposited. Another configuration is a closed configuration, wherein at least part of the sample deposited in the open configuration is compressed by the two plates into a layer of highly uniform thickness, the uniform thickness of the layer is confined by the inner surfaces of the plates and is regulated by the plates and the spacers. In some embodiments, the average spacing between the two plates is more than 300 um.

In a QMAX assay operation, an operator needs to first make the two plates to be in an open configuration ready for sample deposition, then deposit a sample on one or both of the plates, and finally close the plates into a close position. In certain embodiments, the two plates of a QMAX card are initially on top of each other and need to be separated to get into an open configuration for sample deposition. When one of the plate is a thin plastic film (175 um thick PMA), such separation can be difficult to perform by hand. The present invention intends to provide the devices and methods that make the operation of certain assays, such as the QMAX card assay, easy and fast.

In some embodiments, the QMAX device comprises a hinge that connect two or more plates together, so that the plates can open and close in a similar fashion as a book. In some embodiments, the material of the hinge is such that the hinge can self-maintain the angle between the plates after adjustment. In some embodiments, the hinge is configured to maintain the QMAX card in the closed configuration, such that the entire QMAX card can be slide in and slide out a card slot without causing accidental separation of the two plates. In some embodiments, the QMAX device comprises one or more hinges that can control the rotation of more than two plates.

In some embodiments, the hinge is made from a metallic material that is selected from a group consisting of gold, silver, copper, aluminum, iron, tin, platinum, nickel, cobalt, alloys, or any combination of thereof. In some embodiments, the hinge comprises a single layer, which is made from a polymer material, such as but not limited to plastics. The polymer material is selected from the group consisting of acrylate polymers, vinyl polymers, olefin polymers, cellulosic polymers, noncellulosic polymers, polyester polymers, Nylon, cyclic olefin copolymer (COC), poly(methyl methacrylate) (PMMB), polycarbonate (PC), cyclic olefin polymer (COP), liquid crystalline polymer (LCP), polyamide (PB), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFB), polydimethylsiloxane (PDMS), rubbers, or any combinations of thereof. In some embodiments, the polymer material is selected from polystyrene, PMMB, PC, COC, COP, other plastic, or any combination of thereof.

In some embodiments, the QMAX device comprises opening mechanisms such as but not limited to notches on plate edges or strips attached to the plates, making is easier for a user to manipulate the positioning of the plates, such as but not limited to separating the plates of by hand.

In some embodiments, the QMAX device comprises trenches on one or both of the plates. In certain embodiments, the trenches limit the flow of the sample on the plate.

6. Spacers

The devices, apparatus, systems, and methods herein disclosed can include or use a device (e.g. a QMAX device), which comprises spacers that are listed, described and/or summarized in PCT Application (designating U.S.) No. PCT/US2016/045437 filed on Aug. 10, 2016, and U.S. Provisional Application Nos. 62,431,639 filed on Dec. 9, 2016 and 62/456,287 filed on Feb. 8, 2017, which are all hereby incorporated by reference by their entireties.

In essence, the term "spacers" or "stoppers" refers to, unless stated otherwise, the mechanical objects that set, when being placed between two plates, a limit on the minimum spacing between the two plates that can be reached when compressing the two plates together. Namely, in the compressing, the spacers will stop the relative movement of the two plates to prevent the plate spacing becoming less than a preset (i.e. predetermined) value.

The term "a spacer has a predetermined height" and "spacers have a predetermined inter-spacer distance" means, respectively, that the value of the spacer height and the inter spacer distance is known prior to a QMAX process. It is not predetermined, if the value of the spacer height and the inter-spacer distance is not known prior to a QMAX process. For example, in the case that beads are sprayed on a plate as spacers, where beads are landed at random locations of the plate, the inter-spacer distance is not predetermined. Another example of not predetermined inter spacer distance is that the spacers moves during a QMAX processes.

The term "a spacer is fixed on its respective plate" in a QMAX process means that the spacer is attached to a location of a plate and the attachment to that location is maintained during a QMAX (i.e. the location of the spacer on respective plate does not change) process. An example of "a spacer is fixed with its respective plate" is that a spacer is monolithically made of one piece of material of the plate, and the location of the spacer relative to the plate surface does not change during the QMAX process. An example of "a spacer is not fixed with its respective plate" is that a spacer is glued to a plate by an adhesive, but during a use of the plate, during the QMAX process, the adhesive cannot hold the spacer at its original location on the plate surface and the spacer moves away from its original location on the plate surface.

7. Adaptor

The devices, apparatus, systems, and methods herein disclosed can be used with an adaptor, which is configured to accommodate the device and connect the device to a reader, such as but not limited to a smartphone. In some embodiments, the Q-cards are used together with sliders that allow the card to be inserted into the adaptor so that the card can be read by a smartphone detection system. The structure, material, function, variation, dimension and connection of the Q-card, the sliders, and the adaptor are disclosed, listed, described, and/or summarized in PCT Application (designating U.S.) Nos. PCT/US2016/045437 filed on Aug. 10, 2016 and PCT/US0216/051775 filed on Sep. 14, 2016, US Provisional Application Nos. 62/456,590 filed on Feb. 8, 2017, 62/459,554 filed on Feb. 15, 2017, and 62/460,075 filed on Feb. 8, 2017, all of which applications are incorporated herein in their entireties for all purposes.

In some embodiments, the adaptor comprises a receptacle slot, which is configured to accommodate the QMAX device when the device is in a closed configuration. In certain embodiments, the QMAX device has a sample deposited therein and the adaptor can be connected to a mobile device (e.g. a smartphone) so that the sample can be read by the mobile device. In certain embodiments, the mobile device can detect and/or analyze a signal from the sample. In certain embodiments, the mobile device can capture images of the sample when the sample is in the QMAX device and positioned in the field of view (FOV) of a camera, which in certain embodiments, is part of the mobile device.

In some embodiments, the adaptor comprises optical components, which are configured to enhance, magnify, and/or optimize the production of the signal from the sample. In some embodiments, the optical components include parts that are configured to enhance, magnify, and/or optimize illumination provided to the sample. In certain embodiments, the illumination is provided by a light source that is part of the mobile device. In some embodiments, the optical components include parts that are configured to enhance, magnify, and/or optimize a signal from the sample. The structures, functions, and configurations of the optical components in some embodiments can be found in PCT Application (designating U.S.) Nos. PCT/US2016/045437 filed on Aug. 10, 2016 and PCT/US0216/051775 filed on Sep. 14, 2016, US Provisional Application Nos. 62/456,590 filed on Feb. 8, 2017, 62/459,554 filed on Feb. 15, 2017, and 62/460,075 filed on Feb. 8, 2017, all of which applications are incorporated herein in their entireties for all purposes.

8. Dimensions

The devices, apparatus, systems, and methods herein disclosed can include or use a QMAX device, which can comprise plates and spacers. In some embodiments, the dimension of the individual components of the QMAX device and its adaptor are listed, described and/or summarized in PCT Application (designating U.S.) No. PCT/US2016/045437 filed on Aug. 10, 2016, and U.S. Provisional Application Nos. 62,431,639 filed on Dec. 9, 2016 and 62/456,287 filed on Feb. 8, 2017, which are all hereby incorporated by reference by their entireties.

In some embodiments, the dimensions are listed in the Tables below:

Plates:

| Parameters | Embodiments | Preferred Embodiments |
|---|---|---|
| Shape | round, ellipse, rectangle, triangle, polygonal, ring-shaped, or any superposition of these shapes; the two (or more) plates of the QMAX card can have the same size and/or shape, or different size and/or shape; | at least one of the two (or more) plates of the QMAX card has round corners for user safety concerns, wherein the round corners have a diameter of 100 um or less, 200 um or less, 500 um or less, 1 mm or less, 2 mm or less, 5 mm or less, 10 mm or less, 50 mm or less, or in a range between any two of the values. |
| Thickness | the average thickness for at least one of the plates is 2 nm or less, 10 nm or less, 100 nm or less, 200 nm or less, 500 nm or less, 1000 nm or less, 2 μm (micron) or less, 5 μm or less, 10 μm or less, 20 μm or less, 50 μm or less, 100 μm or less, 150 μm or less, 200 μm or less, 300 μm or less, 500 μm or less, 800 μm or less, 1 mm (millimeter) or less, 2 mm or less, 3 mm or less, 5 mm or less, 10 mm or less, 20 mm or less, 50 mm or less, 100 mm or less, 500 mm or less, or in a range between any two of these values | For at least one of the plates is in the range of 0.5 to 1.5 mm; around 1 mm; in the range of 0.15 to 0.2 mm; or around 0.175 mm |
| Lateral Area | For at least one of the plate is 1 mm2 (square millimeter) or less, 10 mm2 or less, 25 mm2 or less, 50 mm2 or less, 75 mm2 or less, 1 cm2 (square centimeter) or less, 2 cm2 or less, 3 cm2 or less, 4 cm2 or less, 5 cm2 or less, 10 cm2 or less, 100 cm2 or less, 500 cm2 or less, 1000 cm2 or less, 5000 cm2 or less, 10,000 cm2 or less, 10,000 cm2 or less, or in a range between any two of these values | For at least one plate of the QMAX card is in the range of 500 to 1000 $mm^2$; or around 750 $mm^2$. |
| Lateral Linear Dimension (width, length, or diameter, etc.) | For at least one of the plates of the QMAX card is 1 mm or less, 5 mm or less, 10 mm or less, 15 mm or less, 20 mm or less, 25 mm or less, 30 mm or less, 35 mm or less, 40 mm or less, 45 mm or less, 50 mm or less, 100 mm or less, 200 mm or less, 500 mm or less, 1000 mm or less, 5000 mm or less, or in a range between any two of these values | For at least one plate of the QMAX card is in the range of 20 to 30 mm; or around 24 mm |
| Recess width | 1 um or less, 10 um or less, 20 um or less, 30 um or less, 40 um or less, 50 um or less, 100 um or less, 200 um or less, 300 um or less, 400 um or less, 500 um or less, 7500 um or less, 1 mm or less, 5 mm or less, 10 mm or less, 100 mm or less, or 1000 mm or less, or in a range between any two of these values. | In the range of 1 mm to 10 mm; Or About 5 mm |

Hinge:

| Parameters | Embodiments | Preferred Embodiments |
|---|---|---|
| Number | 1, 2, 3, 4, 5, or more | 1 or 2 |
| Length of Hinge Joint | 1 mm or less, 2 mm or less, 3 mm or less, 4 mm or less, 5 mm or less, 10 mm or less, 15 mm or less, 20 mm or less, 25 mm or less, 30 mm or less, 40 mm or less, 50 mm or less, 100 mm or less, 200 mm or less, or 500 mm or less, or in a range between any two of these values | In the range of 5 mm to 30 mm. |
| Ratio (hinge joint length vs. aligning plate edge length | 1.5 or less, 1 or less, 0.9 or less, 0.8 or less, 0.7 or less, 0.6 or less, 0.5 or less, 0.4 or less, 0.3 or less, 0.2 or less, 0.1 or less, 0.05 or less or in a range between any two of these values. | In the range of 0.2 to 1; or about 1 |
| Area | 1 mm$^2$ or less, 5 mm$^2$ or less, 10 mm$^2$ or less, 20 mm$^2$ or less, 30 mm$^2$ or less, 40 mm$^2$ or less, 50 mm$^2$ or less, 100 mm$^2$ or less, 200 mm$^2$ or less, 500 mm$^2$ or less, or in a range between any of the two values | In the range of 20 to 200 mm$^2$; or about 120 mm$^2$ |
| Ratio (hinge area vs. plate area) | 1 or less, 0.9 or less, 0.8 or less, 0.7 or less, 0.6 or less, 0.5 or less, 0.4 or less, 0.3 or less, 0.2 or less, 0.1 or less, 0.05 or less, 0.01 or less or in a range between any two of these values | In the range of 0.05 to 0.2, around 0.15 |
| Max. Open Degree | 15 or less, 30 or less, 45 or less, 60 or less, 75 or less, 90 or less, 105 or less, 120 or less, 135 or less, 150 or less, 165 or less, 180 or less, 195 or less, 210 or less, 225 or less, 240 or less, 255 or less, 270 or less, 285 or less, 300 or less, 315 or less, 330 or less, 345 or less or 360 or less degrees, or in a range between any two of these values | In the range of 90 to 180 degrees |
| No. of Layers | 1, 2, 3, 4, 5, or more | 1 or 2 |
| Layer thickness | 0.1 um or less, 1 um or less, 2 um or less, 3 um or less, 5 um or less, 10 um or less, 20 um or less, 30 um or less, 50 um or less, 100 um or less, 200 um or less, 300 um or less, 500 um or less, 1 mm or less, 2 mm or less, and a range between any two of these values | In the range of 20 um to 1 mm; or Around 50 um |
| Angle-maintaining | Limiting the angle adjustment with no more than ±90, ±45, ±30, ±25, ±20, ±15, ±10, ±8, ±6, ±5, ±4, ±3, ±2, or ±1, or in a range between any two of these values | No more than ±2 |

Notch:

| Parameters | Embodiments | Preferred Embodiments |
|---|---|---|
| Number | 1, 2, 3, 4, 5, or more | 1 or 2 |
| Shape | round, ellipse, rectangle, triangle, polygon, ring-shaped, or any superposition or portion of these shapes. | Part of a circle |
| Positioning | Any location along any edge except the hinge edge, or any corner joint by non-hinge edges | |
| Lateral Linear Dimension (Length along the edge, radius, etc.) | 1 mm or less, 2.5 mm or less, 5 mm or less, 10 mm or less, 15 mm or less, 20 mm or less, 25 mm or less, 30 mm or less, 40 mm or less, 50 mm or less, or in a range between any two of these values | In the range of 5 mm to 15 mm; or about 10 mm |
| Area | 1 mm$^2$ (square millimeter) or less, 10 mm$^2$ or less, 25 mm$^2$ or less, 50 mm$^2$ or less, 75 mm$^2$ or less or in a range between any two of these values. | In the range of 10 to 150 mm$^2$; or about 50 mm$^2$ |

Trench:

| Parameters | Embodiments | Preferred Embodiments |
|---|---|---|
| Number | 1, 2, 3, 4, 5, or more | 1 or 2 |
| Shape | Closed (round, ellipse, rectangle, triangle, polygon, ring-shaped, or any superposition or portion of these shapes) or open-ended (straight line, curved line, arc, branched tree, or any other shape with open endings); | |
| Length | 0.001 mm or less, 0.005 mm or less, 0.01 mm or less, 0.05 mm or less, 0.1 mm or less, 0.5 mm or less, 1 mm or less, 2 mm or less, 5 mm or less, 10 mm or less, 20 mm or less, 50 mm or less, 100 mm or less, or in a range between any two of these values | |
| Cross-sectional Area | 0.001 mm$^2$ or less, 0.005 mm$^2$ or less, 0.01 mm$^2$ or less, 0.05 mm$^2$ or less, 0.1 mm$^2$ or less, 0.5 mm$^2$ or less, 1 mm$^2$ or less, 2 mm$^2$ or less, 5 mm$^2$ or less, 10 mm$^2$ or less, 20 mm$^2$ or less, or in a range between any two of these values. | |
| Volume | 0.1 uL or more, 0.5 uL or more, 1 uL or more, 2 uL or more, 5 uL or more, 10 uL or more, 30 uL or more, 50 uL or more, 100 uL or more, 500 uL or more, 1 mL or more, or in a range between any two of these values | In the range of 1 uL to 20 uL; or About 5 uL |

Receptacle Slot

| Parameters | Embodiments | Preferred Embodiments |
|---|---|---|
| Shape of receiving area | round, ellipse, rectangle, triangle, polygon, ring-shaped, or any superposition of these shapes; | |
| Difference between sliding track gap size and card thickness | 100 nm, 500 nm, 1 um, 2 um, 5 um, 10 um, 50 um, 100 um, 300 um, 500 um, 1 mm, 2 mm, 5 mm, 1 cm, or in a range between any two of the values. | In the range of 50 to 300 um; or about 75 um |
| Difference between receiving area and card area | 1 mm$^2$ (square millimeter) or less, 10 mm$^2$ or less, 25 mm$^2$ or less, 50 mm$^2$ or less, 75 mm$^2$ or less, 1 cm$^2$ (square centimeter) or less, 2 cm$^2$ or less, 3 cm$^2$ or less, 4 cm$^2$ or less, 5 cm$^2$ or less, 10 cm$^2$ or less, 100 cm$^2$ or less, or in a range between any of the two values. | |

Certain Conditions for achieving uniform thickness using QMAX card.

In some embodiments, the inter-spacer distance is in the range of 1 μm to 120 μm.

In some embodiments, wherein the plates have a thickness in the range of 20 um to 250 um and Young's modulus in the range 0.1 to 5 GPa.

In some embodiments, for a flexible plate, the thickness of the flexible plate times the Young's modulus of the flexible plate is in the range 60 to 750 GPa-um.

In some embodiments, the layer of uniform thickness sample is uniform over a lateral area that is at least 1 mm$^2$.

In some embodiments, the layer of highly uniform thickness sample has a thickness uniformity of up to +/−5%.

In some embodiments, the spacers are pillars with a cross-sectional shape selected from round, polygonal, circular, square, rectangular, oval, elliptical, or any combination of the same.

In some embodiments, the spacers have pillar shape, have a substantially flat top surface, and have substantially uniform cross-section, wherein, for each spacer, the ratio of the lateral dimension of the spacer to its height is at least 1.

In some embodiments, the spacers are configured in a periodic array form.

In some embodiments, the spacers have a filling factor of 1% or higher, wherein the filling factor is the ratio of the spacer contact area to the total plate area.

In some embodiments, the Young's modulus of the spacers times the filling factor of the spacers is equal or larger than 20 MPa, wherein the filling factor is the ratio of the spacer contact area to the total plate area.

In some embodiments, the spacing between the two plates at the closed configuration is less than 200 um.

In some embodiments, the spacing between the two plates at the closed configuration is a value between 1.8 um and 3.5 um.

In some embodiments, the spacers are fixed on a plate by directly embossing the plate or injection molding of the plate.

In some embodiments, the materials of the plate and the spacers are selected from polystyrene, PMMA, PC, COC, COP, or another plastic.

In some embodiments, the spacers have a pillar shape, and the sidewall corners of the spacers have a round shape with a radius of curvature at least 1 μm.

In some embodiments, the pressing is by human hand.

In some embodiments, at least a portion of the inner surface of one plate or both plates is hydrophilic.

In some embodiments, the sample is a deposition directly from a subject to the plate without using any transferring devices.

In some embodiments, after the sample deformation at a closed configuration, the sample maintains the same final sample thickness, when some or all of the compressing forces are removed.

In some embodiments, the spacers have pillar shape and nearly uniform cross-section.

In some embodiments, the inter-spacer distance (SD) is equal or less than about 120 um (micrometer).

In some embodiments, the inter-spacer distance (SD) is equal or less than about 100 um (micrometer).

In some embodiments, the fourth power of the inter-spacer-distance (ISD) divided by the thickness (h) and the Young's modulus (E) of the flexible plate (ISD$^4$/(hE)) is $5\times10^6$ um$^3$/GPa or less.

In some embodiments, the fourth power of the inter-spacer-distance (ISD) divided by the thickness (h) and the Young's modulus (E) of the flexible plate (ISD$^4$/(hE)) is $5\times10^5$ um$^3$/GPa or less.

In some embodiments, the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one).

In some embodiments, the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one), wherein the fourth power of the inter-spacer-distance (ISD) divided by the thickness (h) and the Young's modulus (E) of the flexible plate (ISD$^4$/(hE)) is $5\times10^6$ um$^3$/GPa or less.

In some embodiments, the ratio of the inter-spacing distance of the spacers to the average width of the spacer is 2 or larger, and the filling factor of the spacers multiplied by the Young's modulus of the spacers is 2 MPa or larger.

In some embodiments, the analytes are the analyte in 5 detection of proteins, peptides, nucleic acids, synthetic compounds, and inorganic compounds.

In some embodiments, the sample is a biological sample selected from amniotic fluid, aqueous humour, vitreous humour, blood whole blood, fractionated blood, plasma, serum, breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, prostatic fluid, nipple aspirate fluid, lachrymal fluid, perspiration, cheek swabs, cell lysate, gastrointestinal fluid, biopsy tissue and urine.

In some embodiments, the spacers have a shape of pillars and a ratio of the width to the height of the pillar is equal or larger than one.

In some embodiments, the sample that is deposited on one or both of the plates has an unknown volume.

In some embodiments, the spacers have a shape of pillar, and the pillar has substantially uniform cross-section.

In some embodiments, the sample is for the detection, purification and quantification of chemical compounds or biomolecules that correlates with the stage of certain diseases.

In some embodiments, the sample is related to infectious and parasitic disease, injuries, cardiovascular disease, cancer, mental disorders, neuropsychiatric disorders, pulmonary diseases, renal diseases, and other and organic diseases.

In some embodiments, the sample is related to the detection, purification and quantification of microorganism.

In some embodiments, the sample is related to virus, fungus and bacteria from environment, water, soil, or biological samples.

In some embodiments, the sample is related to the detection, quantification of chemical compounds or biological samples that pose hazard to food safety, national security, toxic waste, or anthrax.

In some embodiments, the sample is related to quantification of vital parameters in medical or physiological monitor.

In some embodiments, the sample is related to glucose, blood, oxygen level, total blood count.

In some embodiments, the sample is related to the detection and quantification of specific DNA or RNA from biosamples.

In some embodiments, the sample is related to the sequencing and comparing of genetic sequences in DNA in the chromosomes and mitochondria for genome analysis.

In some embodiments, the sample is related to detect reaction products, e.g., during synthesis or purification of pharmaceuticals.

In some embodiments, the sample is cells, tissues, bodily fluids, and stool.

In some embodiments, the sample is the sample in the detection of proteins, peptides, nucleic acids, synthetic compounds, inorganic compounds.

In some embodiments, the sample is the sample in the fields of human, veterinary, agriculture, foods, environments, and drug testing.

In some embodiments, the sample is a biological sample selected from the group consisting of blood, serum, plasma, a nasal swab, a nasopharyngeal wash, saliva, urine, gastric fluid, spinal fluid, tears, stool, mucus, sweat, earwax, oil, a glandular secretion, cerebral spinal fluid, tissue, semen, vaginal fluid, interstitial fluids derived from tumorous tissue, ocular fluids, spinal fluid, a throat swab, breath, hair, finger nails, skin, biopsy, placental fluid, amniotic fluid, cord blood, lymphatic fluids, cavity fluids, sputum, pus, microbiota, meconium, breast milk, exhaled condensate nasopharyngeal wash, nasal swab, throat swab, stool samples, hair, finger nail, ear wax, breath, connective tissue, muscle tissue, nervous tissue, epithelial tissue, cartilage, cancerous sample, and bone.

In some embodiments, the QMAX card includes:
a plurality of scale marks, an imager, and a processing device, wherein:
  (i) at least a portion of the plurality of scale marks comprises the spacers that are periodically arranged;
  (ii) the imager images the scale marks and the device; and
  (iii) the processing device processes one or more images imaged by the imager.

In some embodiments, the processing device comprises a non-transitory computer-readable medium having instructions that, when executed by the processing device, processes the one or more images using one or more image processing algorithms selected from the group consisting of a particle count algorithm, a look up table (LUT) filter, a particle filter, a pattern recognition algorithm, a morphological determination algorithm, a histogram, a line profile, a topographical representation, a binary conversion, a color matching profile, and any combination thereof.

In some embodiments, the QMAX card includes:
i. an imager for imaging the device; and
ii. a processing device for processing one or more images from the imager, wherein the processing device processes the one or more images using an image processing algorithm, and wherein the image processing algorithm includes one or more selected from the group consisting of a particle count algorithm, a look up table (LUT) filter, a particle filter, a pattern recognition algorithm, a morphological determination algorithm, a histogram, a line profile, a topographical representation, a binary conversion, a color matching profile.

In some embodiments, the spacers are in a periodic array.

In some embodiments, the QMAX card includes:
i. an imager for imaging the device;
ii. a processing device for processing one or more images from the imager; and
iii. a non-transitory computer-readable medium comprising machine-executable code that, upon execution by the processing device, implement a method comprising one or more selected from the group consisting of an image acquisition algorithm, an image processing algorithm, a user interface method that (i) facilitates interaction between a user and a computational device and (ii) serves as means for data collection, data transmission and analysis, a communication protocol, and a data processing algorithm.

In some embodiments, the QMAX card includes:
i. an imager for imaging the device;
ii. a processing device for processing one or more images from the imager; and
iii. a non-transitory computer-readable medium comprising machine-executable code that, upon execution by the processing device, implement a method comprising one or more selected from the group consisting of detecting a signal from the sample, correcting raw data based on at least one of:
  a. mathematical manipulation,
  b. mathematical correction, and
  c. one or more calibrations specific for the device or reagents used to examine the sample, including calculating a value, calculating a concentration value, comparing with a baseline, comparing with a threshold, comparing with a standard curve, comparing with historical data, determining the accuracy of a test, determining outlying values or results, determining values or results above or below a normal or acceptable range, determining values or results indicative of an abnormal condition, determining two or more results which, together, indicate the presence of an abnormal condition, curve-fitting, using data as the basis of mathematical or analytical reasoning selected from the group consisting of deductive reasoning, inductive reasoning, Bayesian reasoning.

In some embodiments, the non-transitory computer-readable medium comprises machine-executable code that, upon execution by the processing device, implements a method comprising comparing data with a database to retrieve instructions for a course of action to be performed by the subject.

In some embodiments, the database is stored on the device.

In some embodiments, the QMAX card includes:
i. an imager for imaging the device to generate data; and
ii. a processing device for processing the data from the imager, wherein the processing comprises at least one selected from the group consisting of binning data, transforming data, transforming time domain data by Fourier Transform to frequency domain, and combining the data with additional data.

In some embodiments, the QMAX card includes:
i. an imager for imaging the device to generate data; and
ii. a processing device for processing the data from the imager; and
iii. a non-transitory computer-readable medium comprising machine-executable code that, upon execution by the processing device, implement a method comprising one or more selected from the group consisting of detecting a signal from the sample, correcting raw data based on at least one of:

a. mathematical manipulation,
b. mathematical correction, and
c. one or more calibrations specific for the device or reagents used to examine the sample, including calculating a value, calculating a concentration value, comparing with a baseline, comparing with a threshold, comparing with a standard curve, comparing with historical data, determining the accuracy of a test, determining outlying values or results, determining values or results above or below a normal or acceptable range, determining values or results indicative of an abnormal condition, determining two or more results which, together, indicate the presence of an abnormal condition, curve-fitting, using data as the basis of mathematical or analytical reasoning selected from the group consisting of deductive reasoning, inductive reasoning, Bayesian reasoning.

In some embodiments, the processing may involve comparing the processed data with a database stored in the device to retrieve instructions for a course of action to be performed by the subject.

In some embodiments, the QMAX card includes:
i. an imager for imaging the device to generate data; and
ii. a processing device for processing the data from the imager, wherein the processing comprises determining an accuracy of a test.

In some embodiments, the QMAX card includes:
i. an imager for imaging the device; and
ii. a scanner configured to image different areas of the device,
wherein the spacers comprise a periodic array of spacers.

In some embodiments, the QMAX card includes:
i. an imager for imaging the device; and
ii. a scanner configured to image different areas of the device.

In some embodiments, the analyte is a protein, peptides, DNA, RNA, nucleic acid, molecules, cells, tissues, viruses, nanoparticles with different shapes, or a combination thereof.

In some embodiments, the analyte comprises a stained cell.

In some embodiments, the analyte comprises a stained cell comprising neutrophils, lymphocytes, monocytes, eosinophils or basophils.

In some embodiments, the analyte comprises a stained analyte, wherein the stain comprising acridine Orange dye.

In some embodiments, the QMAX card includes an imager and a processing device, wherein
(i) the imager images the device; and
(ii) the processing device processes one or more images imaged by the imager and analyzes an analyte.

In some embodiments, the QMAX card includes an imager and a processing device, wherein
(i) the imager images the device; and
(ii) the processing device processes one or more images imaged by the imager, analyzes an analyte and counts a concentration of the analyte.

In some embodiments, the QMAX card includes a measurement device, wherein the measurement device detects and/or quantifies the analyte by measuring a signal related to the analyte, wherein the signal is an optical signal, electrical signal, mechanical signal, chemi-physical signal, or any combination of thereof.

In some embodiments, the QMAX card includes a measurement device, wherein the measurement device detects and/or quantifies the analyte by measuring an optical signal related to the analyte, wherein the optical signal comprising light reflection, scattering, transmission, absorption, spectrum, color, emission, intensity, wavelength, location, polarization, luminescence, fluorescence, electroluminescence, chemoluminescence, electrochemoluminescence, or any combination of thereof.

In some embodiments, the QMAX card includes a measurement device, wherein the measurement device detects and/or quantifies the analyte by measuring an electric signal related to the analyte, wherein the electrical signal comprising charge, current, impedance, capacitance, resistance, or any combination of thereof.

In some embodiments, the QMAX card includes a measurement device, wherein the measurement device detects and/or quantifies the analyte by measuring a mechanical signal related to the analyte, wherein the mechanical signal comprising mechanical wave, sound wave, shock wave, or vibration.

In some embodiments, the QMAX card includes a measurement device, wherein the measurement device detects and/or quantifies the analyte by measuring a chemi-physical signal related to the analyte, wherein the chemi-physical signal includes, but not limited to, PH value, ions, heat, gas bubbles, color change, that are generated in a reaction.

In some embodiments, the QMAX card includes a dry reagent coated on one or both plates.

In some embodiments, the spacer height is approximately the average thickness of RBCs.

In some embodiments, the spacer has a height of 5 um (micron) or less.

In some embodiments, the spacer has a height of 10 um (micron) or less.

In some embodiments, the spacer has a height of 30 um (micron) or less.

In some embodiments, the spacer has a height of 10 um (micron) or less, 20 um (micron) or less, 30 um (micron) or less, 50 um (micron) or less, or a range between any two of the values.

In some embodiments, the analyte comprises the cells comprising red blood cells, while blood cells, or platelets.

In some embodiments, the analyte comprises cancer cells, viruses, or bacteria in the blood.

In some embodiments, the spacers are in a periodic array.

In some embodiments, the periodic array comprises a lattice.

In some embodiments, the lattice comprises spacers having a cross-sectional shape selected from the group consisting of a square, a rectangle, a triangle, a hexagon, a polygon, and any combination thereof.

In some embodiments, the lattice comprises two or more spacers having a different cross-sectional shape selected from the group consisting of a square, a rectangle, a triangle, a hexagon, a polygon, and any combination thereof.

In some embodiments, the lattice comprises two or more regions comprising spacers, and the cross-sectional shape of the spacers in each of the two or more regions is independently selected from the group consisting of a square, a rectangle, a triangle, a hexagon, a polygon, and any combination thereof.

In some embodiments, the lattice comprises two or more regions comprising spacers, and the period between each spacer in a first region of the two or more regions is different than the period between each spacer in a second region of the two or more regions.

In some embodiments, the QMAX card includes a plurality of scale marker that are spacers.

In some embodiments, the QMAX card includes one or more scale marks.

In some embodiments, the one or more scale marks are etched, deposited, or printed onto at least one of the first plate and the second plate.

In some embodiments, the one or more scale marks absorb light, reflect light, scatter light, interfere with light, diffract light, emit light, or any combination of thereof.

In some embodiments, the QMAX card includes a plurality of scale marks, wherein at least two of the plurality of scale marks are separated by a known distance as measured in a direction that is parallel to a plane of a lateral area of a relevant volume of the sample.

In some embodiments, the QMAX card includes one or more scale marks, wherein at least one of the one or more scale marks is a spacer.

In some embodiments, the QMAX card includes one or more location marks.

In some embodiments, the one or more location marks are spacers.

In some embodiments, the QMAX card includes an imager, wherein the imager images the spacers are used to assist the quantification of a relevant volume of the sample.

In some embodiments, the analyte is selected from the group consisting of a cell, a blood cell, a red blood cell, a white blood cell, a granulocyte, a neutrophil, an eosinophil, a basophil, a lymphocyte, a monocyte, a platelet, a cancer cell, a virus, a bacteria, a fungus, a protein, a nucleic acid, a DNA molecule, an RNA molecule, an miRNA molecule, an mRNA molecule, a hemocyte, a peptide, a polypeptide, a tissue, a nanoparticle, a drug metabolite, a lipid, a carbohydrate, a hormone, a vitamin, a combination thereof, a fragment thereof, and a derivative thereof.

In some embodiments, the uniform thickness of the sample layer in a closed configuration deviates from the spacer height by less than +/−5%.

In some embodiments, the sample deposited on the plate in an open configuration is deposited directly from a subject to the plate without using any transferring devices.

In some embodiments, the sample deposited on the plate in an open configuration has an amount of the sample that is unknown.

In some embodiments, the uniform thickness of the sample layer in a closed configuration is used to calculate a volume of a sample that is regulated by the plates and the spacers of the device.

In some embodiments, the QMAX card includes one or a plurality of binding sites that on one or both plate sample contact surfaces of the device, and wherein each of the binding sites selectively binds and immobilizes an analyte or analytes that is in or is suspected in a sample.

In some embodiments, the QMAX card includes one or a plurality of storage sites on one or both plate sample contact surfaces, wherein each of the storage sites stores a reagent or reagents, wherein the reagent(s) dissolve and diffuse in a sample when the device is in a closed configuration.

In some embodiments, the QMAX card includes one or a plurality of amplification sites on one or both of the sample contact surfaces of the device, wherein each of the amplification sites is capable of amplifying a signal from an analyte in a sample or a label of the analyte when the analyte or the label is within 500 nm from an amplification site.

In some embodiments, the QMAX card includes a first assay site on the sample contact area for assessing a first analyte, and in and assaying a second analyte in the second predetermined assay site.

In some embodiments, the QMAX card includes a pair of electrodes on the sample contact area, wherein an analyte assay area is between the electrodes.

In some embodiments, the spacer is a height that is configured to make a reaction of the analyte with a reagent to be saturated in less than 60 seconds.

In some embodiments, one or both of the plate further comprises, on its surface, a plurality of assay sites, wherein the distance between the edges of neighboring assay sites is substantially larger than the thickness of the uniform thickness layer when the plates are in the closed position, wherein at least a part of the uniform thickness layer is over the assay sites, and wherein the sample has one or a plurality of analytes that are capable of diffusing in the sample.

In some embodiments, the first plate has, on its surface, at least two neighboring analyte assay sites that are not separated by a distance that is substantially larger than the thickness of the uniform thickness layer when the plates are in the closed position, wherein at least a part of the uniform thickness layer is over the assay sites, and wherein the sample has one or a plurality of analytes that are capable of diffusing in the sample.

In some embodiments, one or both of the plate further comprises, on its surface, a plurality of assay sites, wherein the distance between the edges of neighboring assay sites is configured that in a time of 30 mins or less, the reaction at each site occurs independently, without a fluidic barrier to fluidically separate a sample into different isolation liquid pockets.

In some embodiments, the QMAX card includes a mobile communication device that communicates with the remote location via a Wi-Fi or cellular network.

In some embodiments, the QMAX card includes a mobile communication device that is a mobile phone.

In some embodiments, the QMAX card includes a mobile communication device that receives a prescription, diagnosis or a recommendation from a medical professional at a remote location.

In some embodiments, the analyte is measured by using an label that is selected from the group consisting of a light-emitting label, a fluorescent label, a dye, a quantum dot, a luminescent label, electro-luminescent label, a chemi-luminescent label, a bead, an electromagnetic radiation emitter, an optical label, an electric label, enzymes that can be used to generate an optical or electrical signal, a nanoparticle, a colorimetric label, an enzyme-linked reagent, a multicolor reagent, and an avidin-streptavidin associated detection reagent.

In some embodiments, the analyte is measured by using an label comprising a fluorescent label that is selected from the group consisting of IRDye800CW, Alexa 790, Dylight 800, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514, Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoyl-carbocyanine iodide), tetrabromorhodamine 123, rhodamine 6G, TMRM (tetramethyl rhodamine methyl ester), TMRE (tetramethyl rhodamine ethyl ester), tetramethylrosamine, rhodamine B, 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2'disulfonic acid, acridine, acridine isothiocyanate, 5-(2'-aminoethyl)aminonaphthalene-1-sulfonic acid (EDANS), 4-amino-N-[3-vinylsulfonyl)phenyl]naphth-alimide-3,5 disulfonate, N-(4-anilino-1-naphthyl)maleimide, anthranilamide, 4,4-difluoro-5-(2-thienyl)-4-bora-3a,4a diaza-5-indacene-3-propioni-c acid BODIPY, cascade blue, Brilliant Yellow, coumarin, 7-amino-4-methylcoumarin (AMC, Coumarin 120),7-amino-4-trifluoromethylcoumarin (Coumarin 151), cyanine dyes, cyanosine, 4',6-diaminidino-2-phenylindole (DAPI), 5',5"-dibromopyrogallol-sulfonaphthalein (Bromopyrogallol Red), 7-diethylamino-3-(4'-isothiocyanato-phenyl)-4-methylcoumarin, diethylenetriaamine pentaacetate, 4,4'-diisothiocyanatodihydro-stilbene-2-,2'-disulfonic acid, 4,4'-diisothiocyanatostilbene-2,2'-disulfonic acid, 5-(dimethylamino]naphthalene-1-sulfonyl chloride (DNS, dansylchloride), 4-dimethylaminophenylazophenyl-4'-isothiocyanate (DABITC), eosin, eosin isothiocyanate, erythrosin, erythrosin B, isothiocyanate, ethidium, fluorescein, 5-carboxyfluorescein (FAM),5-(4,6-dichlorotriazin-2-yl) amino-fluorescein (DTAF), 2',7'dimethoxy-4'5'-dichloro-6-carboxyfluorescein (JOE), fluorescein isothiocyanate, QFITC, (XRITC), fluorescamine, IR144, IR1446, Malachite Green isothiocyanate, 4-methylumbelli-feroneortho cresolphthalein, nitrotyrosine, pararosaniline, Phenol Red, B-phycoerythrin, o-phthaldialdehyde, pyrene, pyrene butyrate, succinimidyl 1-pyrene, butyrate quantum dots, Reactive Red 4 (Cibacron™ Brilliant Red 3B-A) rhodamine, 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, tetramethyl hodamine isothiocyanate (TRITC), riboflavin, 5-(2'-aminoethyl) aminonaphthalene-1-sulfonic acid (EDANS), 4-(4'-dimethylaminophenylazo)benzoic acid (DABCYL), rosolic acid, CAL Fluor Orange 560, terbium chelate derivatives, Cy 3, Cy 5, Cy 5.5, Cy 7, IRD 700, IRD 800, La Jolla Blue, phthalo cyanine, naphthalo cyanine, coumarin, xanthene dyes such as rhodols, resorufins, bimanes, acridines, isoindoles, dansyl dyes, aminophthalic hydrazides such as luminol, isoluminol derivatives, aminophthalimides, aminonaphthalimides, aminobenzofurans, aminoquinolines, dicyanohydroquinones, fluorescent europium, terbium complexes, a green fluorescent protein (GFP), a GFP derived from *Aequoria victoria*, a "humanized" derivative such as Enhanced GFP, a GFP from *Renilla reniformis, Renilla mulleri, Ptilosarcus guernyi*, "humanized" recombinant GFP (hrGFP), a combination thereof, a fragment thereof, and a derivative thereof.

In some embodiments, the sample is blood, and the analyte is one or more selected from the group consisting of white blood cells, red blood cells, and platelets.

In some embodiments, the QMAX card includes scale marks, wherein the scale marks comprise spacers that are periodically arranged.

In some embodiments, the spacers are arranged in a periodic array, and wherein the periodic array has a rectangular lattice.

In some embodiments, the spacers are arranged in a periodic array, and wherein the periodic array has a triangular lattice, square lattice, diamond lattice, pentagonal lattice, hexagonal lattice, heptagonal lattice, octagonal lattice, nonagonal lattice, or a decagonal lattice.

9. Hand Pressing

For the devices, apparatus, systems, and methods herein disclosed, human hands can be used for manipulating or handling or the plates and/or samples. In some embodiments, human hands can be used to press the plates into a closed configuration; In some embodiments, human hands can be used to press the sample into a thin layer. The manners in which hand pressing is employed are described and/or summarized in PCT Application (designating U.S.) Nos. PCT/US2016/045437 filed on Aug. 10, 2016 and PCT/US0216/051775 filed on Sep. 14, 2016, and in US Provisional Application Nos. 62/431,639 filed on Dec. 9, 2016, 62/456,287 filed on Feb. 8, 2017, 62/456,065 filed on Feb. 7, 2017, 62/456,504 filed on Feb. 8, 2017, and 62/460, 062 filed on Feb. 16, 2017, which are all hereby incorporated by reference by their entireties.

In some embodiments, human hand can be used to manipulate or handle the plates of the QMAX device. In certain embodiments, the human hand can be used to apply an imprecise force to compress the plates from an open configuration to a closed configuration. In certain embodiments, the human hand can be used to apply an imprecise force to achieve high level of uniformity in the thickness of the sample (e.g. less than 5%, 10%, 15%, or 20% variability).

10. Smartphone

The devices, apparatus, systems, and methods herein disclosed can be used with a mobile device, such as but not limited to a smartphone. The smartphone detection technology is herein disclosed, or listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments, the smartphone comprises a camera, which can be used to capture images or the sample when the sample is positioned in the field of view of the camera (e.g. by an adaptor). In certain embodiments, the camera includes one set of lenses (e.g. as in iPhone™ 6). In certain embodiments, the camera includes at least two sets of lenses (e.g. as in iPhone™ 7). In some embodiments, the smartphone comprises a camera, but the camera is not used for image capturing.

In some embodiments, the smartphone comprises a light source such as but not limited to LED (light emitting diode). In certain embodiments, the light source is used to provide illumination to the sample when the sample is positioned in the field of view of the camera (e.g. by an adaptor). In some embodiments, the light from the light source is enhanced, magnified, altered, and/or optimized by optical components of the adaptor.

In some embodiments, the smartphone comprises a processor that is configured to process the information from the sample. The smartphone includes software instructions that, when executed by the processor, can enhance, magnify, and/or optimize the signals (e.g. images) from the sample. The processor can include one or more hardware components, such as a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction-set computer (RISC), a microprocessor, or the like, or any combination thereof.

In some embodiments, the smartphone comprises a communication unit, which is configured and/or used to transmit data and/or images related to the sample to another device. Merely by way of example, the communication unit can use a cable network, a wireline network, an optical fiber network, a telecommunications network, an intranet, the Internet, a local area network (LAN), a wide area network (WAN), a wireless local area network (WLAN), a metropolitan area network (MAN), a wide area network (WAN), a public telephone switched network (PSTN), a Bluetooth network, a ZigBee network, a near field communication (NFC) network, or the like, or any combination thereof.

In some embodiments, the smartphone is an iPhone™, an Android™ phone, or a Windows™ phone.

11. Cloud

The devices, apparatus, systems, and methods herein disclosed can be used with cloud storage and computing technologies. The related cloud technologies are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments, the cloud storage and computing technologies can involve a cloud database. Merely by way of example, the cloud platform can include a private cloud, a public cloud, a hybrid cloud, a community cloud, a distributed cloud, an inter-cloud, a multi-cloud, or the like, or any combination thereof. In some embodiments, the mobile device (e.g. smartphone) can be connected to the cloud through any type of network, including a local area network (LAN) or a wide area network (WAN).

In some embodiments, the data (e.g. images of the sample) related to the sample is sent to the cloud without processing by the mobile device and further analysis can be conducted remotely. In some embodiments, the data related to the sample is processed by the mobile device and the results are sent to the cloud. In some embodiments, both the raw data and the results are transmitted to the cloud.

The invention claimed is:

1. A method of assaying an analyte in a sample comprising:
   (i) having a sample holder with a sample contact area for contacting a sample containing or suspected of containing an analyte;
   (ii) having a plurality of calibration structures in the sample contact area of the sample holder, wherein the calibration structures have definite and predetermined geometry, and each of the calibration structures has an average lateral dimension of 100 μm or less;
   (iii) imaging a part of the sample contact area that has the calibration structures with an imager to obtain an image; and
   (iv) using an algorithm that comprises (a) the image in (iii), (b) the calibration structures in the image, and (c) machine learning to (1) identify the analyte, or (2) determine the analyte concentration, or (3) both (1) and (2).

2. The method of claim 1, wherein the definite and predetermined geometry of the calibration structures is the predetermined inter-distance between two neighboring calibration structures.

3. The method of claim 1, wherein the machine learning uses the calibration structures for analyte detection.

4. The method of claim 1, further comprising (a) an optical box of claim 1 and (b) a step inserting the sample holder into an optical box.

5. The method of claim 1, further comprising taking images with a bright-field illumination optics and a fluorescent illumination optics.

6. The method of claim 1, further comprising reconstructing the multiple images into a three-dimensional volume.

7. The method of claim 1, wherein a training database of the machine learning uses the micro/nano optical calibration structures.

8. The method of claim 1, wherein the analyte detection uses a mage transformation comprising GAN (Generative and Adversarial Network) based machine learning model.

9. The method of claim 1, wherein the sample holder comprises: a first plate, a second plate, and spacers, wherein:
   (i) the plates are movable relative to each other into different configurations;
   (ii) one or both plates are flexible;
   (iii) each of the plates has, on its respective inner surface, a sample contact area for contacting a deformable sample;
   (iv) one or both of the plates comprise the spacers that are fixed with a respective plate;
   (v) the spacers have a predetermined substantially uniform height and a predetermined inter-spacer-distance; and
   (vi) at least one of the spacers is inside the sample contact area;
   wherein in an open configuration the two plates are separated apart, the spacing between the plates is not regulated by the spacers, and the sample is deposited on one or both of the plates; and
   wherein in a closed configuration, configured after the sample deposition in the open configuration, at least part of the sample is compressed by the two plates into a layer of uniform thickness, and the uniform thickness of the layer is confined by the inner surfaces of the two plates and is regulated by the plates and the spacers.

10. The method of claim 1, wherein the analysis comprises tomography.

11. The method of claim 1, wherein the analyte comprises cell, virus, bacterium, nanoparticle, or molecule.

12. The method of claim 1, wherein the sample comprises at least one of cells, tissues, bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, and exhaled breath condensate.

13. The method of claim 1, wherein the calibration structures are spacers.

14. A system of assaying an analyte in a sample comprising:
   (i) a sample holder with a sample contact area for contacting a sample containing or suspected of containing an analyte;
   (ii) a plurality of calibration structures on the sample contact area of the sample holder, wherein the calibration structures have predetermined inter-distance between two neighboring calibration structures and each of the calibration structures has a lateral dimension of an average 100 μm or less;
(iii) an imager that images a part of the sample contact area that has the calibration structures; and
(iv) a non-transitory computer-readable medium comprising an algorithm that comprises (a) the image in (iii), (b) the calibration structures in the image, and (c) machine learning, to (1) identify the analyte, or (2) determine the analyte concentration or both (1) and (2).

15. The system of claim 14, further comprising a processing device that processes one or more images imaged by the imager,
and the processing device comprises a non-transitory computer-readable medium having instructions that, when executed by the processing device, processes the one or more images using one or more image processing algorithms selected from the group consisting of a particle count algorithm, a look up table (LUT) filter, a particle filter, a pattern recognition algorithm, a morphological determination algorithm, a histogram, a line profile, a topographical representation, a binary conversion, a color matching profile, and any combination thereof.

16. The system of claim 14, wherein the definite and predetermined geometry of the calibration structures is the predetermined inter-distance between two neighboring calibration structures.

17. The system of claim 16, wherein the predetermined inter-distance between two neighboring calibration structures is periodic of a periodicity of 150 μm or less.

18. The system of claim 16, wherein the predetermined inter-distance between two neighboring calibration structures is periodic of a periodicity of 400 μm or less.

19. The system of claim 14, wherein the calibration structures have a predetermined optical property.

20. The system of claim 14, wherein the calibration structures are periodic.

21. The system of claim 14, further comprising an adaptor, wherein the adaptor comprises
(i) a holder frame, and
(ii) an optical box removably attached to the holder frame, wherein the holder frame is configured to removably fit over a mobile device and align the optical box to a camera and an illumination source integrated in the mobile device.

22. The system of claim 21, wherein the mobile device is a smartphone.

23. The system of claim 14, wherein the further comprising an optical box that comprises:
(i) a receptacle slot configured to receive and position the sample holder in a sample slide in the field of view and focal range of the imager;
(ii) a bright-field illumination optics configured to capture bright-field microscopy images of the sample;
(iii) a fluorescent illumination optics configured to capture fluorescent microscopy images of a sample; and
(iv) a lever configured to switch between the bright-field illumination optics and the fluorescent illumination optics by sliding inward and outward in the optical box.

24. The system of claim 14, wherein the machine learning uses the calibration structures for analyte detection.

25. The system of claim 14, wherein the algorithm identifies the analyte and determines the analyte concentration.

26. The system of claim 14, wherein the algorithm identifies the analyte.

27. The system of claim 14, further comprising a side-emitting optical fiber ring in which light is emitted out from a side wall of the optical fiber to illuminate the sample in the sample holder.

28. The system of claim 14, wherein a training database of the machine learning uses the micro/nano optical calibration structures.

29. The system of claim 14, wherein the analyte detection uses a mage transformation comprising GAN (Generative and Adversarial Network) based machine learning model.

30. The system of claim 14, wherein the sample holder comprises: a first plate, a second plate, and spacers, wherein:
(i) the plates are movable relative to each other into different configurations;
(ii) one or both plates are flexible;
(iii) each of the plates has, on its respective inner surface, a sample contact area for contacting a deformable sample;
(iv) one or both of the plates comprise the spacers that are fixed with a respective plate;
(v) the spacers have a predetermined substantially uniform height and a predetermined inter-spacer-distance; and
(vi) at least one of the spacers is inside the sample contact area;
wherein in an open configuration the two plates are separated apart, the spacing between the plates is not regulated by the spacers, and the sample is deposited on one or both of the plates; and
wherein in a closed configuration, configured after the sample deposition in the open configuration, at least part of the sample is compressed by the two plates into a layer of uniform thickness, and the uniform thickness of the layer is confined by the inner surfaces of the two plates and is regulated by the plates and the spacers.

31. The system of claim 30, wherein the spacer has a height of 30 μm or less.

32. An optical adaptor for assaying an analyte in a sample, comprising:
a sample holder frame and an imager, wherein:
(i) the sample holder frame has a sample holder and at least one plate with a sample contact area for contacting a sample containing or suspected of containing an analyte; and
(ii) the sample holder on the sample contact area has a plurality of calibration structures that have predetermined and known inter-distance between two neighboring calibration structures, and wherein the optical calibration structures are imaged by an imager and are used by an algorithm that comprises (a) the image from the imager, (b) the calibration structures in the image, and (c) machine learning, to (1) identify the analyte, or (2) determine the analyte concentration, or both (1) and (2).

* * * * *